US012024555B2

(12) United States Patent
Crowe, Jr.

(10) Patent No.: US 12,024,555 B2
(45) Date of Patent: Jul. 2, 2024

(54) HUMAN WEST NILE VIRUS ANTIBODIES AND METHODS OF USE THEREFOR

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 917 days.

(21) Appl. No.: 17/041,790

(22) PCT Filed: Mar. 26, 2019

(86) PCT No.: PCT/US2019/024019
§ 371 (c)(1),
(2) Date: Sep. 25, 2020

(87) PCT Pub. No.: WO2019/191057
PCT Pub. Date: Oct. 3, 2019

(65) Prior Publication Data
US 2021/0115115 A1 Apr. 22, 2021

Related U.S. Application Data

(60) Provisional application No. 62/648,673, filed on Mar. 27, 2018.

(51) Int. Cl.
*C07K 16/10* (2006.01)
(52) U.S. Cl.
CPC .... *C07K 16/1081* (2013.01); *C07K 2317/565* (2013.01); *C07K 2317/76* (2013.01)
(58) Field of Classification Search
None
See application file for complete search history.

(56) References Cited

U.S. PATENT DOCUMENTS

2004/0031072 A1 2/2004 Rosa et al.

OTHER PUBLICATIONS

Gould et al., NEJM, May 4, 2023, 388(18):1633-1636. (Year: 2023).*
Barba-Spaeth et al., Structural basis of potent Zika-dengue virus antibody cross-neutralization, *Nature* 536, 48-53, doi:10.1038/nature18938, 2016.
Beasley, D. W. & Barrett, A. D., Identification of neutralizing epitopes within structural domain III of the West Nile virus envelope protein, *J Virol* 76, 13097-13100, 2002.
Cherrier et al., Structural basis for the preferential recognition of immature flaviviruses by a fusion-loop antibody, *EMBO J* 28, 3269-3276, doi:10.1038/emboj.2009.245; 2009.
Crill, W. D. & Chang, G. J., Localization and characterization of flavivirus envelope glycoprotein cross-reactive epitopes, *J Virol* 78, 13975-13986, doi:10.1128/JVI.78.24.13975-13986.2004, 2004.

De Alwis et al., Identification of human neutralizing antibodies that bind to complex epitopes on dengue virions, *Proc Natl Acad Sci U S A* 109, 7439-7444, doi:10.1073/pnas.1200566109, 2012.
Dejnirattisai et al., A new class of highly potent, broadly neutralizing antibodies isolated from viremic patients infected with dengue virus, *Nat Immunol* 16, 170-177, doi:10.1038/ni.3058, 2015.
Fibriansah et al., A highly potent human antibody neutralizes dengue virus serotype 3 by binding across three surface proteins, *Nat Commun* 6, 6341, doi:10.1038/ncomms7341, 2015.
Fibriansah et al., Dengue Virus. Cryo-EM structure of an antibody that neutralizes dengue virus type 2 by locking E protein dimers, *Science* 349, 88-91, doi:10.1126/science.aaa8651, 2015.
Goncalvez et al., Epitope determinants of a chimpanzee Fab antibody that efficiently cross-neutralizes dengue type 1 and type 2 viruses map to inside and in close proximity to fusion loop of the dengue type 2 virus envelope glycoprotein, *J Virol* 78, 12919-12928, doi:10.1128/JVI.78.23.12919-12928.2004, 2004.
Gould et al., Protective and Therapeutic Capacity of Human Single-Chain Fv-Fc Fusion Proteins against West Nile Virus, *J Virol* 79, 14606-14613, doi:10.1128/JVI.79.23.14606-14613.2005, 2005.
Guirakhoo et al., The Murray Valley encephalitis virus prM protein confers acid resistance to virus particles and alters the expression of epitopes within the R2 domain of E glycoprotein, *Virology* 191, 921-931, 1992.
Hasan et al., A human antibody against Zika virus crosslinks the E protein to prevent infection, *Nat Commun* 8, 14722, doi:10.1038/ncomms14722, 2017.
Heinz et al., Structural changes and functional control of the tick-borne encephalitis virus glycoprotein E by the heterodimeric association with protein prM, *Virology* 198, 109-117, doi:10.1006/viro.1994.1013, 1994.
International Preliminary Report on Patentability issued in corresponding PCT Application No. PCT/US2019/024019, dated Oct. 8, 2020.
International Search Report and Written Opinion issued in corresponding PCT Application No. PCT/US2019/024019, dated Aug. 21, 2019.
Kaufmann et al., Neutralization of West Nile virus by cross-linking of its surface proteins with Fab fragments of the human monoclonal antibody CR4354, *Proc Natl Acad Sci U S A* 107, 18950-18955, doi:10.1073/pnas.1011036107, 2010.
Lai et al., Antibodies to envelope glycoprotein of dengue virus during the natural course of infection are predominantly cross-reactive and recognize epitopes containing highly conserved residues at the fusion loop of domain II, *J Virol* 82, 6631-6643, doi:10.1128/JVI.00316-08, 2008.

Li et al., Differential expression of domain III neutralizing epitopes on the envelope proteins of West Nile virus strains, *Virology* 335, 99-105, doi:10.1016/j.virol.2005.02.011, 2005.

Nelson et al., Maturation of West Nile Virus Modulates Sensitivity to Antibody-Mediated Neutralization, *PLoS Pathog* 4, e1000060, doi:10.1371/journal.ppat.1000060, 2008.

(Continued)

*Primary Examiner* — Stacy B Chen
(74) *Attorney, Agent, or Firm* — Parker Highlander PLLC

(57) ABSTRACT

The present disclosure is directed to antibodies binding to and neutralizing West Nile virus and methods for use thereof.

20 Claims, 30 Drawing Sheets

Specification includes a Sequence Listing.

(56) References Cited

OTHER PUBLICATIONS

Nybakken et al., Structural basis of West Nile virus neutralization by a therapeutic antibody, *Nature* 437, 764-769, doi:10.1038/nature03956, 2005.

Oliphant et al., Development of a humanized monoclonal antibody with therapeutic potential against West Nile virus, *Nat Med* 11, 522-530, doi:10.1038/nm1240, 2005.

Oliphant et al., Antibody recognition and neutralization determinants on domains I and II of West Nile Virus envelope protein, *J Virol* 80, 12149-12159, doi:10.1128/JVI.01732-06; 2006.

Oliphant et al., Induction of epitope-specific neutralizing antibodies against West Nile virus, *J Virol* 81, 11828-11839, doi:10.1128/JVI.00643-07, 2007.

Pierson et al., The stoichiometry of antibody-mediated neutralization and enhancement of West Nile virus infection, *Cell Host Microbe* 1, 135-145, doi:10.1016/j.chom.2007.03.002, 2007.

Sanchez et al., Characterization of neutralizing antibodies to West Nile virus, *Virology* 336, 70-82, doi:10.1016/j.virol.2005.02.020, 2005.

Sapparapu et al., Neutralizing human antibodies prevent Zika virus replication and fetal disease in mice, *Nature* 540, 443-447, doi:10.1038/nature20564, 2016.

Smith et al., The potent and broadly neutralizing human dengue virus-specific monoclonal antibody 1C19 reveals a unique cross-reactive epitope on the bc loop of domain II of the envelope protein, *MBio* 4, e00873-00813, doi:10.1128/mBio.00873-13, 2013.

Teoh et al., The structural basis for serotype-specific neutralization of dengue virus by a human antibody, *Sci Transl Med* 4, 139ra183, doi:10.1126/scitranslmed.3003888, 2012.

Throsby et al., Isolation and Characterization of Human Monoclonal Antibodies from Individuals Infected with West Nile Virus, *J Virol* 80, 6982-6992, doi:10.1128/JVI.00551-06, 2006.

Tsioris et al., "Neutralizing antibodies against West Nile virus identified directly from human B cells by single-cell analysis and next generation sequencing." *Integr Biol (Camb)*, 7(12): 1587-97, 2015.

VanBlargan et al., Deconstructing the Antiviral Neutralizing-Antibody Response: Implications for Vaccine Development and Immunity, *Microbiol Mol Biol Rev* 80, 989-1010, doi:10.1128/MMBR.00024-15, 2016.

Zhang et al., Neutralization mechanism of a highly potent antibody against Zika virus, *Nat Commun* 7, 13679, doi:10.1038/ncomms13679, 2016.

\* cited by examiner

Serum neutralization of WNV (RVPs)

FIG. 1A

Serum neutralization of WNV (RVPs)

FIG. 1B mAb neutralization of WNV (RVPs)

FIG. 1E mAb neutralization of WNV (fully infectious)

FIG. 1F

WNV-62

FIG. 2E

WNV-86

FIG. 2F

Media vs WNV WT

FIG. 3B

WNV-86 vs WNV WT

FIG. 3C

WNV Passage 3

— ■ — WNV-86 #1
— △ — WNV-86 #2
···○··· Media #1
···●··· Media #2

*FIG. 3D*

| Untreated | PNGase F |
| WT   T64N | WT   T64N |

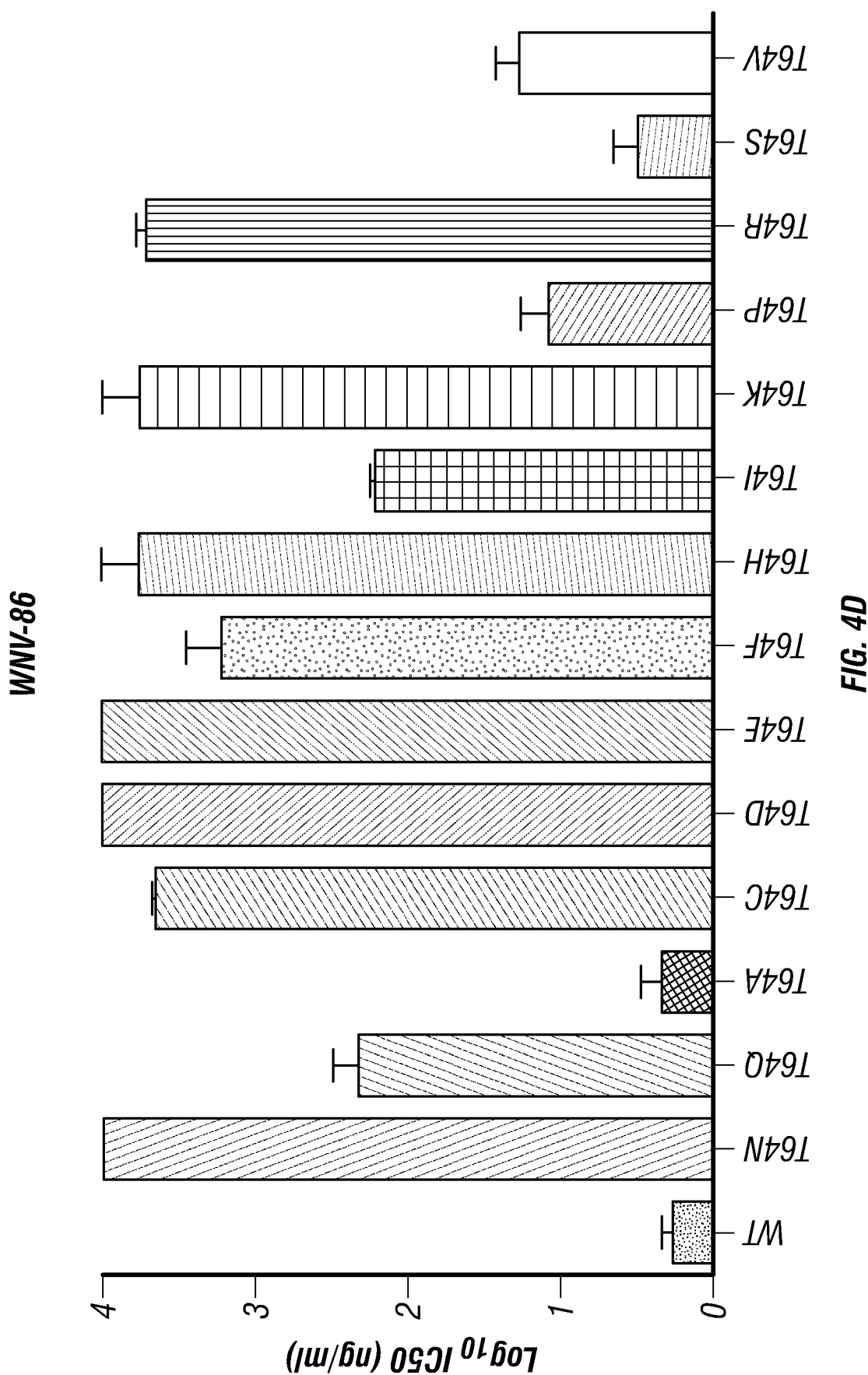

WNV-86 vs WNV T64Q

*FIG. 5A*

Media vs WNV T64Q

*FIG. 5B*

WNV Passage 2

- WNV-86 #1
- WNV-86 #2
- Media #1
- Media #2

FIG. 5C

WNV-86

WNV infection of C57BL/6J mice

— WNV-10
----- WNV-86
······ hE16
--- hCHK152

$P < 0.0001$

% Survival vs Days Post Infection

FIG. 6

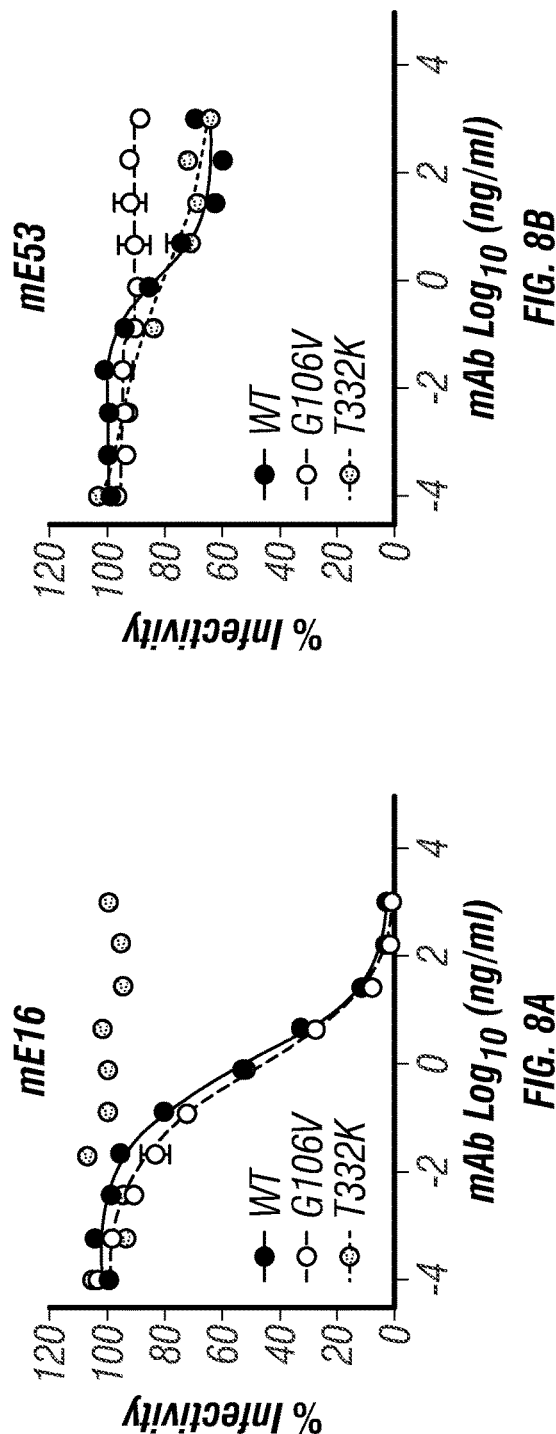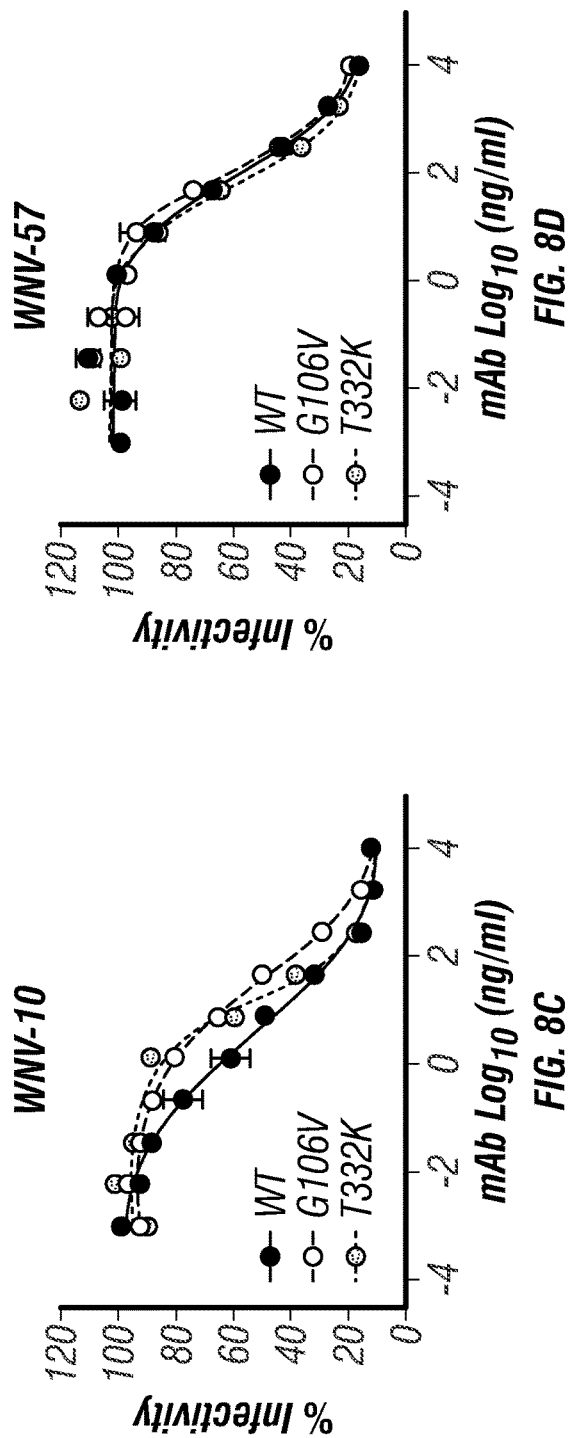

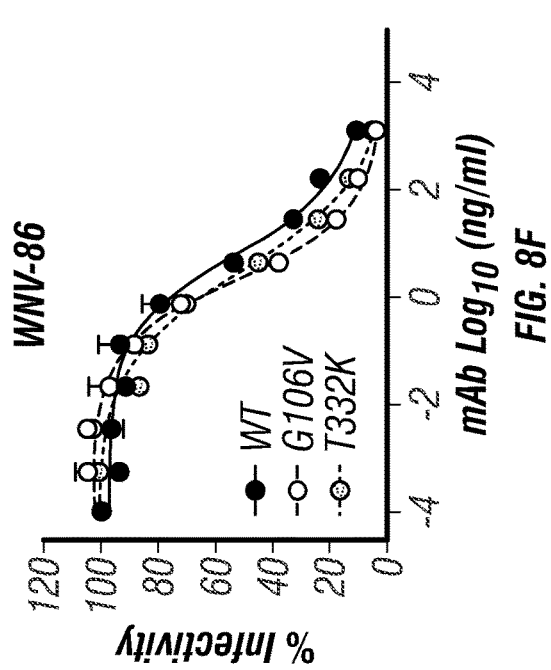
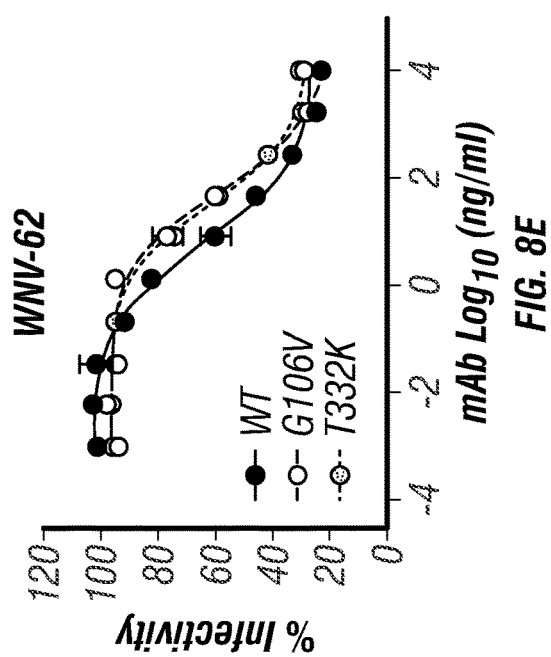
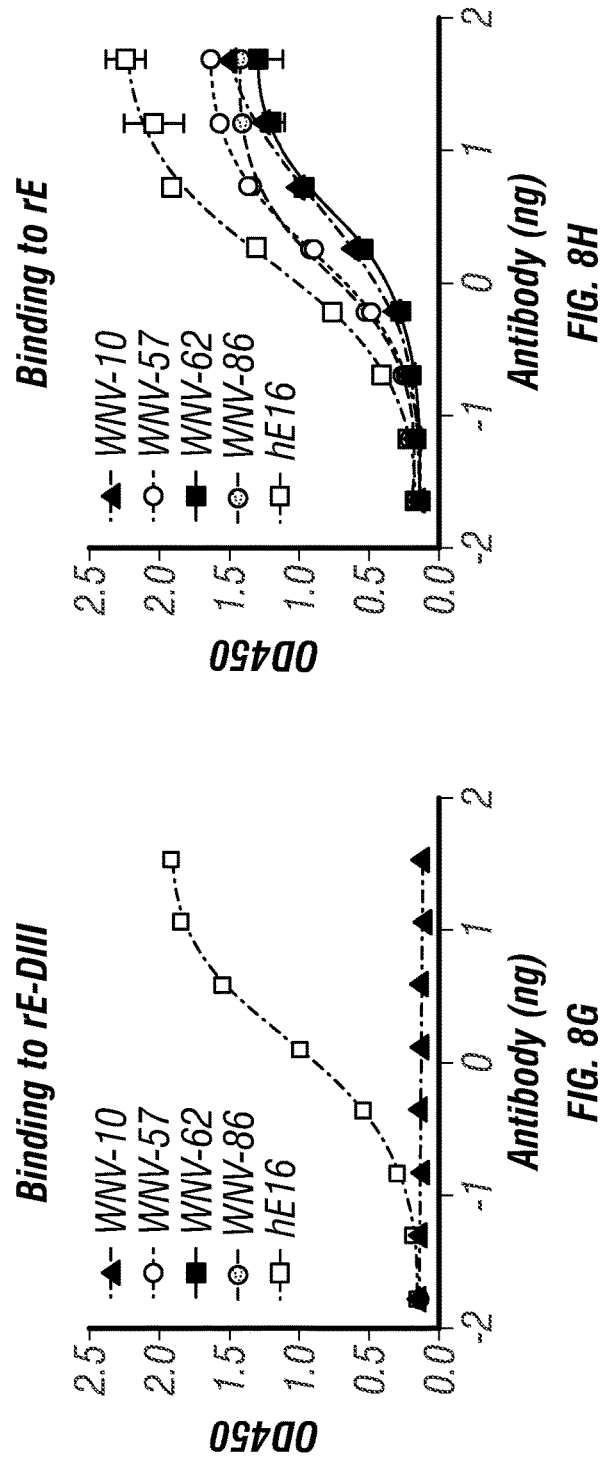

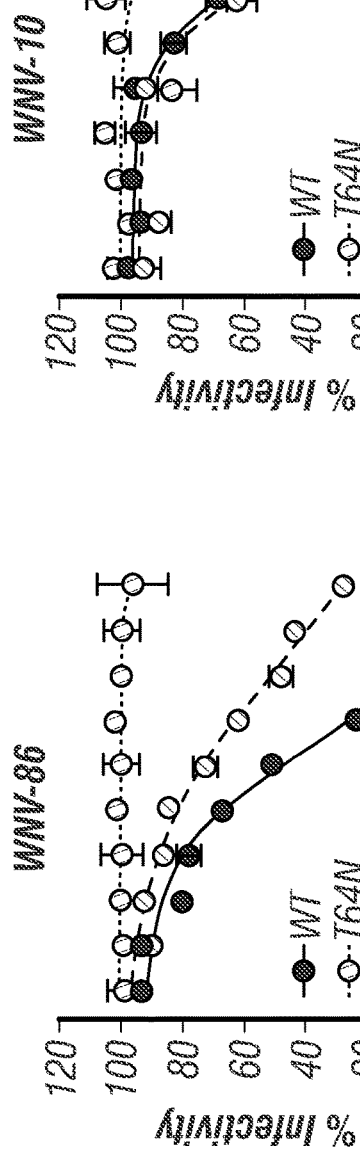
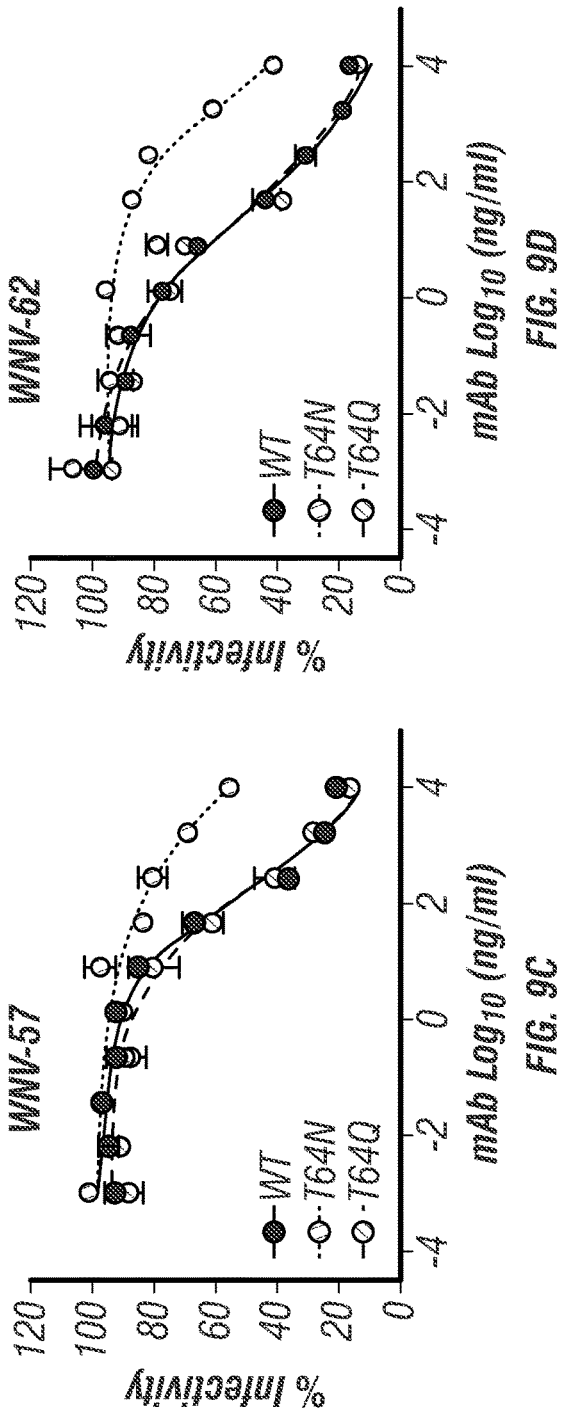

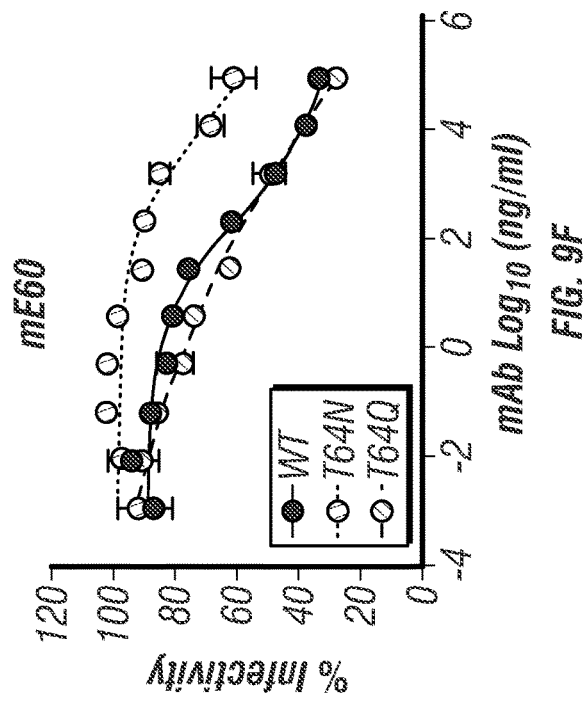
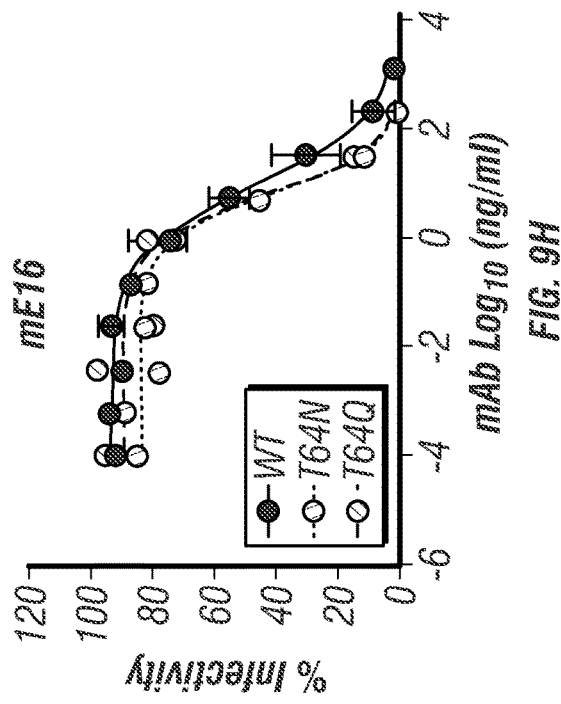
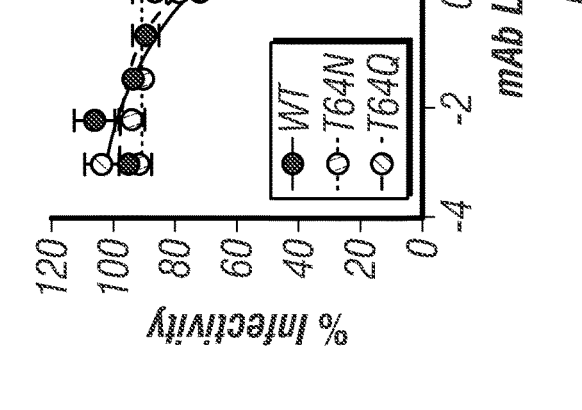
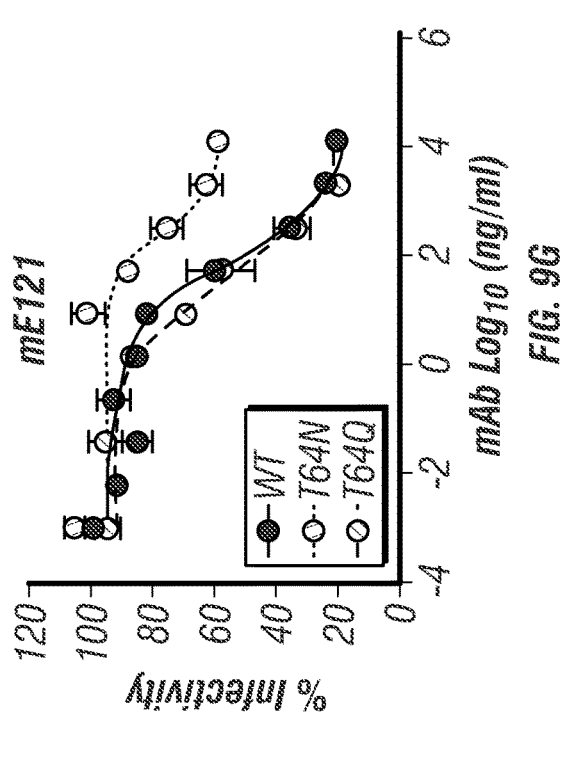

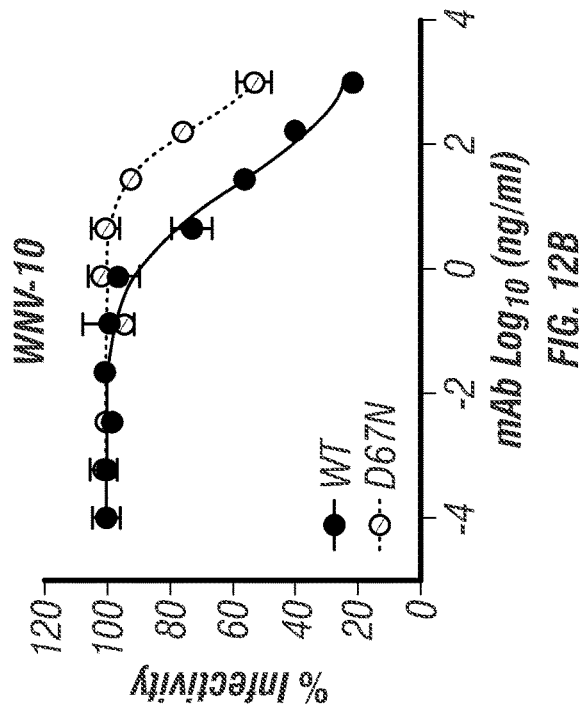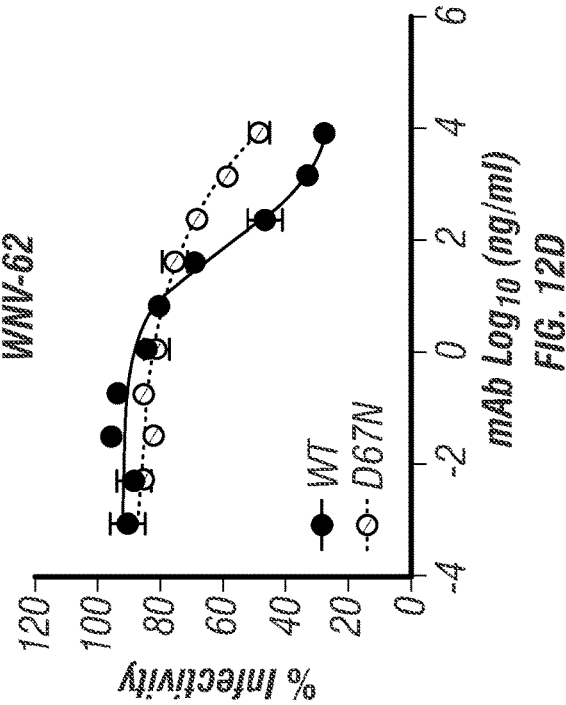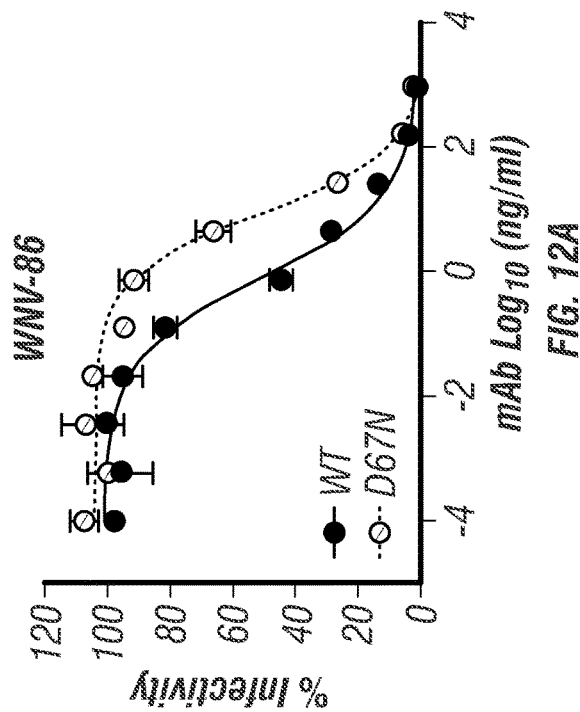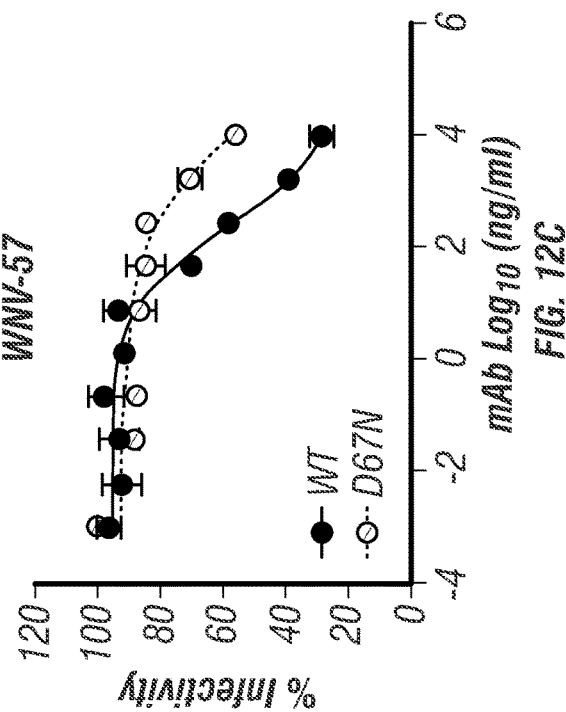

HUMAN WEST NILE VIRUS ANTIBODIES AND METHODS OF USE THEREFOR

PRIORITY CLAIM

This application is a national phase application under 35 U.S.C. § 371 of International Application No. PCT/US2019/024019, filed Mar. 26, 2019, which claims benefit of priority to U.S. Provisional Application Ser. No. 62/648,673, filed Mar. 27, 2018, the entire contents of each of which are incorporated by reference herein.

BACKGROUND

1. Field of the Disclosure

The present disclosure relates generally to the fields of medicine, infectious disease, and immunology. More particular, the disclosure relates to human antibodies binding to West Nile virus (WNV).

2. Background

Flaviviruses are a group of arthropod-borne, enveloped, positive-stranded RNA viruses that include pathogens of global health significance such as WNV, dengue virus (DENV), yellow fever virus (YFV), and Zika virus (ZIKV). For some flaviviruses, including YFV, Japanese encephalitis virus (JEV), tick-borne encephalitis virus (TBEV), and DENV, licensed vaccines are available. The development of neutralizing antibodies (NAbs) in vitro is a correlate of protection for most (Roehrig et al., 2001; Belmusto-Worn et al., 2005; Markhoff, 2000), but not all (Capeding et al., 2014; Villar et al., 2015) of these vaccines. For other emerging flaviviruses such as WNV and ZIKV, licensed vaccines or therapeutic agents for use in humans are lacking.

The main target of flavivirus NAbs is the E protein, which mediates entry into host cells, and consists of three structural domains (DI, DII, DIII), a helical stem, and two antiparallel transmembrane helices. Although cryo-electron microscopic reconstructions of mature flavivirus particles reveal a smooth surface densely covered with 90 E dimers that lie flat against the viral membrane (Kuhn et al., 2002; Zhang et al., 2013; Sirohi et al., 2016; Kostyuchenko et al., 2016; Mukhopadhyay et al., 2003), flaviviruses display structural heterogeneity, owing in part to an inefficient maturation process (Pierson and Diamond, 2012) that results in incomplete cleavage of a chaperone protein, prM, from the virion surface. Unlike the smooth surface of mature particles, the surfaces of immature particles are composed of prM-E heterotrimeric spikes, while partially mature particles contain structural features of both immature and mature particles (Pierson & Diamond, 2012). The maturation state of flaviviruses impacts antibody recognition: compared to mature virions that contain little or no prM, virions that retain prM are generally more sensitive to neutralization by mAbs or polyclonal antibodies in sera (Guirakhoo et al., 1992; Heinz et al., 1994; Nelson et al., 2008). This finding is perhaps observed because the heterotrimeric arrangement of E proteins in association with prM on incompletely mature particles improves overall accessibility of epitopes relative to that of mature particles lacking prM, on which E protein homodimers are assembled into a dense herringbone structure (Pierson & Diamond, 2012).

Following infection or vaccination, the majority of both mouse and human flavivirus antibodies target epitopes that include the fusion loop at the distal end of DII (DII-FL) and possess low neutralizing activity (Throsby et al., 2006; Oliphant et al., 2007; Lai et al., 2008; Dejnirattisai et al., 2015; Sapparupu et al., 2016), although some antibodies targeting epitopes overlapping DII-FL strongly neutralizing potently (Dejnirattisai et al., 2015; Goncalvez et al., 2004; Smith et al., 2013). Although most potently neutralizing mouse antibodies target DIII, DIII is not a major target of human NAbs (reviewed in VanBlargan et al., 2016). Instead, most potent human NAbs target quaternary epitopes that span multiple E proteins within or between dimers (Dejnirattisai et al., 2015; Kaufmann et al., 2010; de Alwis et al., 2012; Teoh et al., 2012; Fibriansah et al., 2015a; 2015b; Barba-Spaeth et al., 2016; Zhang et al., 2016; Hasan et al., 2017). These antibodies often bind to E proteins arranged on the virion surface, but not to soluble forms of E proteins (Dejnirattisai et al., 2015; Kaufmann et al., 2010; de Alwis et al., 2012).

Because of the importance of antibodies in WNV immunity (Diamond et al., 2003; Ben-Nathan et al., 2003; Engle & Diamond, 2003), several groups have investigated the therapeutic potential of humanized or human mAbs (Throsby et al., 2006; Oliphant et al., 2005) and antibody fragments (Gould et al., 2005). An example is the strongly neutralizing mouse mAb E16 (Pierson et al., 2007), which demonstrated therapeutic efficacy even when administered 5 days post-infection (Oliphant et al., 2005). E16 recognises a highly accessible epitope in the lateral ridge of E DIII (Nybakken et al., 2005), a common target of potently neutralizing mouse mAbs (Oliphant et al., 2005; Sanchez et al., 2005; Choi et al., 2007; Beasley & Barrett, 2002).

SUMMARY

Thus, in accordance with the present disclosure, there is provided method of detecting a West Nile virus infection in a subject comprising (a) contacting a sample from said subject with an antibody or antibody fragment having clone-paired heavy and light chain CDR sequences from Tables 3 and 4, respectively; and (b) detecting West Nile virus in said sample by binding of said antibody or antibody fragment to a West Nile virus antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in West Nile virus antigen levels as compared to the first assay.

The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another embodiment, there is provided a method of treating a subject infected with West Nile virus, or reducing the likelihood of infection of a subject at risk of contracting West Nile virus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to eliminate FcR interactions, such as a LALA or N297 mutation, or mutated to extend antibody in vivo half-life, such as a YTE, LS or DHS mutation. The antibody may be a chimeric antibody or a bispecific antibody. The antibody or antibody fragment may further comprise a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to eliminate FcR interactions, such as a LALA or N297 mutation, or mutated to extend antibody in vivo half-life, such as a YTE, LS or DHS mutation. The antibody may be a chimeric antibody or a bispecific antibody. The antibody or antibody fragment may further comprise a cell penetrating peptide and/or is an intrabody.

Also provided is a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to eliminate FcR interactions, such as a LALA or N297 mutation, or mutated to extend antibody in vivo half-life, such as a YTE, LS or DHS mutation. The antibody may be a chimeric antibody or a bispecific antibody. The antibody or antibody fragment may further comprise a cell penetrating peptide and/or is an intrabody.

In still a further embodiment, there is provided a vaccine formulation comprising one or more antibodies or antibody fragments characterized by clone-paired heavy and light chain CDR sequences from Tables 3 and 4, respectively. At least one of said antibodies or antibody fragments may be encoded by light and heavy chain variable sequences according to clone-paired sequences from Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. At least one of said antibodies or antibody fragments may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The at least one antibody fragment may be a recombinant scFv (single chain fragment variable) antibody, Fab fragment, F(ab')$_2$ fragment, or Fv fragment. The at least one antibody may be an IgG, or a recombinant IgG antibody or antibody fragment comprising an Fc portion mutated to eliminate FcR interactions, such as a LALA or N297 mutation, or mutated to extend antibody in vivo half-life, such as a YTE, LS or DHS mutation. The at least one antibody may be a chimeric antibody or a bispecific antibody. The at least one antibody or antibody fragment may further comprise a cell penetrating peptide and/or is an intrabody.

In still another embodiment, there is provided a vaccine formulation comprising an antibody or antibody fragment that binds to West Nile virus E protein and (a) does not bind to epitopes DII-FL or DIII; (b) preferentially neutralizes mature virus particles lacking prM; and/or (c) does not cross-neutralize dengue virus serotype 1 or Zika virus H/PF/2013 strain. The antibody or antibody fragment may not bind to epitopes DII-FL or DIII and preferentially neutralizes mature virus particles lacking prM. The antibody or antibody fragment may preferentially neutralize mature virus particles lacking prM and does not cross-neutralize dengue virus serotype 1 or Zika virus H/PF/2013 strain. The antibody or antibody fragment may not cross-neutralize dengue virus serotype 1 or Zika virus H/PF/2013 strain and does not bind to epitopes DII-FL or DIII.

Also provided is a method of protecting the health of a placenta and/or fetus of a pregnant a subject infected with or at risk of infection with West Nile virus comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to eliminate FcR interactions, such as a LALA or N297 mutation, or mutated to extend antibody in vivo half-life, such as a YTE, LS or DHS mutation. The antibody may be a chimeric antibody or a bispecific antibody. The antibody or antibody fragment may further comprise a cell penetrating peptide and/or is an intrabody. The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In still yet a further embodiment, there is provided a method of determining the antigenic integrity of an antigen comprising (a) contacting a sample comprising said antigen with a first antibody or antibody fragment having clone-paired heavy and light chain CDR sequences from Tables 3 and 4, respectively; and (b) determining antigenic integrity of said antigen by detectable binding of said first antibody or antibody fragment to said antigen. The sample may comprise recombinantly produced antigen. The sample may comprise a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

There is also provided a human monoclonal antibody or antibody fragment, or hybridoma or engineered cell producing the same, wherein said antibody beings to West Nile virus E protein and (a)does not bind to epitopes DII-FL or DIII; (b) preferentially neutralizes mature virus particles lacking prM; and/or (c) does not cross-neutralize dengue virus serotype 1 or Zika virus H/PF/2013 strain.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-F. WNV neutralization by human serum samples or mAbs. (FIG. 1A) Representative dose-response neutralization curves of WNV RVPs for 13 WNV convalescent human serum samples. Infectivity levels were normalized to those observed in the absence of antibody. Error bars indicate the range of duplicate infections. (FIG. 1B) Mean values of the reciprocal serum dilution required to inhibit infection by 50% ($NT_{50}$) obtained from five independent experiments, as indicated by circles. Error bars represent the standard error of the mean. The dotted horizontal line shows the lowest serum dilution tested. PBMCs from donors 865, 866, and 870 were selected for EBV transformation and B cell hybridoma formation. Representative dose-response neutralization curves of (FIG. 1C) WNV RVPs or (FIG. 1D) fully infectious WNV for mAbs isolated from donors 866, 865, and 870. Infectivity levels were normalized to those observed in the absence of antibody. Error bars indicate the range of duplicate infections. Mean values of mAb concentration required to inhibit infectivity by 50% ($IC_{50}$) for (FIG. 1E) WNV RVPs and (FIG. 1F) fully infectious WNV were calculated from 3 to 10 independent experiments, as indicated by circles. Error bars represent the standard error of the mean. Hashed bars indicate that neutralization was not observed at the highest mAb concentration tested (10 μg/mL). The donor from whom mAbs were isolated is indicated below the x-axis in FIGS. 1C-D.

FIGS. 2A-G. Effect of virion maturation state on mAb neutralization. WNV RVPs prepared in the presence of overexpressed furin or ammonium chloride to increase (prM−) or decrease (prM+) the efficiency of virion maturation, respectively, were tested for sensitivity to neutralization by mouse mAbs (FIG. 2A) mE16 or (FIG. 2B) mE53; or human mAbs (FIG. 2C) WNV-10, (FIG. 2D) WNV-57, (FIG. 2E) WNV-62, or (FIG. 2F) WNV-86. Representative dose-response curves are shown with infectivity normalized to levels observed in the absence of antibody. Error bars indicate the range of duplicate infections. (FIG. 2G) Mean $IC_{50}$ values for each mAb were obtained from three independent experiments. Error bars indicate the standard error of the mean. The P-values indicated were obtained from paired t-tests.

FIGS. 3A-D. In vitro selection of WNV-86 escape variant viruses. (FIG. 3A) Vero cell monolayer cultures were inoculated with WNV in duplicate at a MOI of 0.1 in the presence of mAb WNV-86 or medium only. Continuous viral replication was maintained by serial passaging of virus supernatant diluted 1:10 in medium with or without mAb WNV-86 on fresh Vero cell monolayers. At each passage, an aliquot of viral supernatant from (FIG. 3B) medium only or (FIG. 3C) mAb WNV-86 selection was diluted serially and used to inoculate Raji-DCSIGNR in the presence or absence of WNV-86 to monitor the growth of escape variant viruses. Viral infectivity was determined by measuring the percentage of GFP-positive cells by flow cytometry. The number of serial passages is indicated on the x-axis. (FIG. 3D) Passage 3 virus supernatant obtained from duplicate wells of WNV-86 or medium only selection was tested for neutralization sensitivity against WNV-86. Error bars indicate the range of duplicate infections.

FIGS. 4A-E. Characteristics of WNV E T64 RVP variants. (FIG. 4A) The E protein glycan occupancy of standard preparations of WNV WT or T64N RVPs was assessed by SDS-PAGE followed by western blotting of virus lysates that were either untreated or treated with PNGaseF. E protein was detected using mouse mAb 4G2. WT WNV RVPs or variants containing a mutation at E residue 64 were tested for sensitivity to neutralization by (FIG. 4B) human mAb WNV-86 or (FIG. 4C) murine mAb E16. Representative dose-response curves are shown. Infectivity was normalized to levels observed in the absence of antibody. Error bars indicate the range of duplicate infections. Average $IC_{50}$ values of (FIG. 4D) WNV-86 or (FIG. 4E) mE16 against WNV E T64 RVP variants were obtained from three independent experiments. Error bars represent the standard error of the mean. Hashed bars indicate that an $IC_{50}$ value that could not be calculated accurately due to limited neutralization sensitivity.

FIGS. 5A-G. Epitope mapping of mAb WNV-86. WNV T64Q was passaged on Vero cell monolayer cultures in the presence of WNV-86 using a strategy similar to that described in FIGS. 3A-D. At each passage, an aliquot of viral supernatant from (FIG. 5A) mAb WNV-86 or (FIG. 5B) medium only selection was diluted serially and used to inoculate Raji-DCSIGNR in the presence or absence of WNV-86 to monitor the growth of escape variant viruses. Viral infectivity was determined by measuring the percentage of GFP-positive cells by flow cytometry. The number of serial passages is indicated on the x-axis. (FIG. 5C) Passage 2 virus supernatant obtained from duplicate wells of WNV-86 or medium only selection was tested for neutralization sensitivity against WNV-86. Error bars indicate the range of duplicate infections. (FIG. 5D) Representative dose-response neutralization curves of WNV WT, T64Q, T208K, or T64Q_T208K RVPs for WNV-86. Error bars indicate the range of duplicate infections. (FIG. 5E) Crystal structure of the WNV E protein monomer (PDB 2HG0) with DI, DII, DIII, and DII-FL indicated above the structure. Gray spheres indicate mutated residues selected for epitope mapping studies. Differentially shaded spheres indicate mutations at residues that reduce WNV-86 neutralization potency by >4-fold relative to WT. The orange and cyan arrows indicate the location of mutation at residues T64 and T208, respectively, identified by in vitro selection experiments. (FIG. 5F) Neutralization profile of WNV RVPs containing mutations that reduce WNV-86 neutralization potency by >4-fold for murine mAb E16. Error bars indicate the range of duplicate infections. Curves shown are representative of at least two independent experiments. (FIG. 5G) Fold change in WNV-86 $IC_{50}$ values against WNV E variants indicated in FIG. 5E relative to WT. Colored bars correspond to residues on the crystal structure in FIG. 5E.

FIG. 6. Therapeutic efficacy of mAbs. Five-week old C576J/BL6 mice were inoculated with 100 FFU of WNV, passively immunized with 100 μg of mAbs WNV-10 or WNV-86 two days following infection and monitored for survival. Mice immunized with WNV-specific hE16 or CHIKV-specific humanized mAb CHK152 (hCHK152) were used as positive or negative controls, respectively. The indicated P-value was obtained from a log-rank test.

FIGS. 8A-H. Effect of DII-FL and DIII-LR mutations on mAb neutralization. Standard preparations of wild type (WT) WNV RVPs or variants containing a mutation that abrogates binding by many antibodies targeting epitopes within DII-FL (G106V) or DIII-LR (T332K) were tested for sensitivity to neutralization by murine mAbs (FIG. 8A) mE16 or (FIG. 8B) mE53; or human mAbs (FIG. 8C) WNV-10, (FIG. 8D) WNV-57, (FIG. 8E) WNV-62, or (FIG. 8F) WNV-86. Dose-response neutralization curves shown are representative of three independent experiments. Infectivity was normalized to levels observed in the absence of antibody. Error bars indicate the range of duplicate infections. mAb binding to recombinant (FIG. 8G) WNV E protein DIII only or (FIG. 8H) WNV E protein ectodomain was determined by ELISA. DIII-specific humanized mAb E16 (hE16) was used as a control. Error bars indicate the standard deviation of the mean OD450 value obtained from triplicate wells.

FIGS. 9A-H. Effect of mutations at E residue T64 on mAb neutralization. Standard preparations of WNV WT, WNV T64N, or WNV T64Q RVPs were tested concurrently for sensitivity to neutralization by human mAbs (FIG. 9A) WNV-86, (FIG. 9B) WNV-10, (FIG. 9C) WNV-57, (FIG. 9D) WNV-62; or murine mAbs (FIG. 9E) mE53, (FIG. 9F) mE60, (FIG. 9G) mE121, or (FIG. 9H) mE16. Dose-response curves representative of two independent experiments are shown. Infectivity was normalized to levels observed in the absence of antibody. Error bars indicate the range of duplicate infections.

(FIG. 10C) Crystal structure of the WNV E protein monomer (PDB 2HG0) with DI, DII, DIII, and DII-FL indicated above the structure. Residues that reduced the neutralization potency of mAb WNV-86 or WNV-10 are highlighted in orange or magenta, respectively.

Figures 11A, 11B, 11C, 11D:
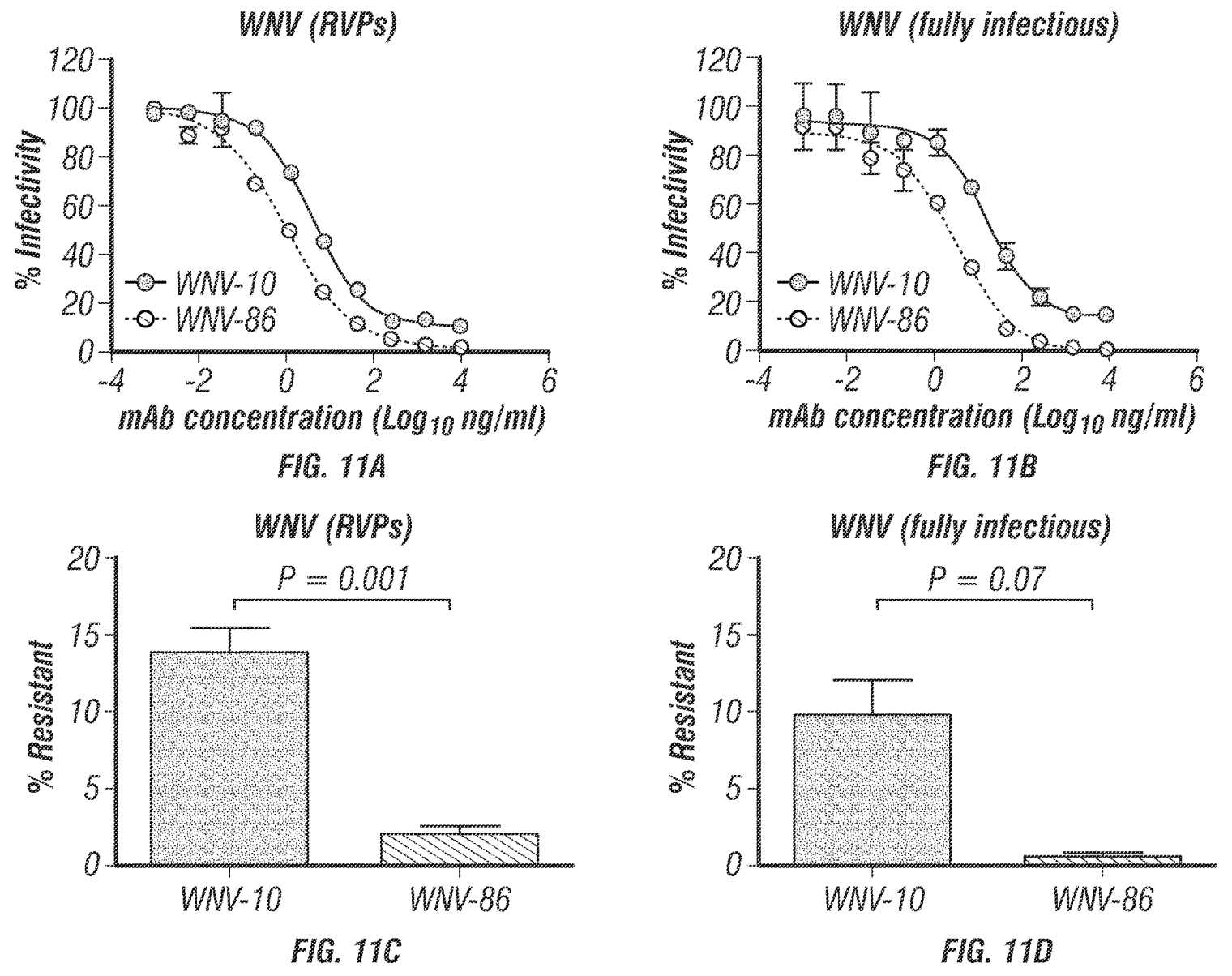

FIGS. 11A-D. Incomplete neutralization by mAb WNV-10. Neutralization of WT WNV (FIG. 11A) RVPs or (FIG. 11B) fully infectious viruses by mAbs WNV-10 or WNV-86. Error bars indicate the range of duplicate infections. Curves shown are representative of at least 3 independent experiments. Mean percentages of WNV (FIG. 11C) RVPs or (FIG. 11D) fully infectious viruses that remain resistant to neutralization at the highest concentration of mAb WNV-10 or WNV-86 tested (10 µg/mL) were obtained from 7 or 3 independent experiments with RVPs or infectious viruses, respectively. Error bars represent the standard error of the mean. The indicated P-values were obtained from paired t-tests.

FIGS. 12A-H. Effect of WNV D67N mutation on neutralization by mAbs. Standard preparations of WNV WT or D67N RVPs were tested concurrently for sensitivity to neutralization by human mAbs (FIG. 12A) WNV-86, (FIG. 12B) WNV-10, (FIG. 12C) WNV-57, (FIG. 12D) WNV-62; or murine mAbs (FIG. 12E) mE53, (FIG. 12F) mE60, (FIG. 12G) mE121, or (FIG. 12H) mE16. Dose-response curves representative of three independent experiments are shown. Infectivity was normalized to levels observed in the absence of antibody. Error bars indicate the range of duplicate infections.

DESCRIPTION OF ILLUSTRATIVE EMBODIMENTS

Figure 1C:
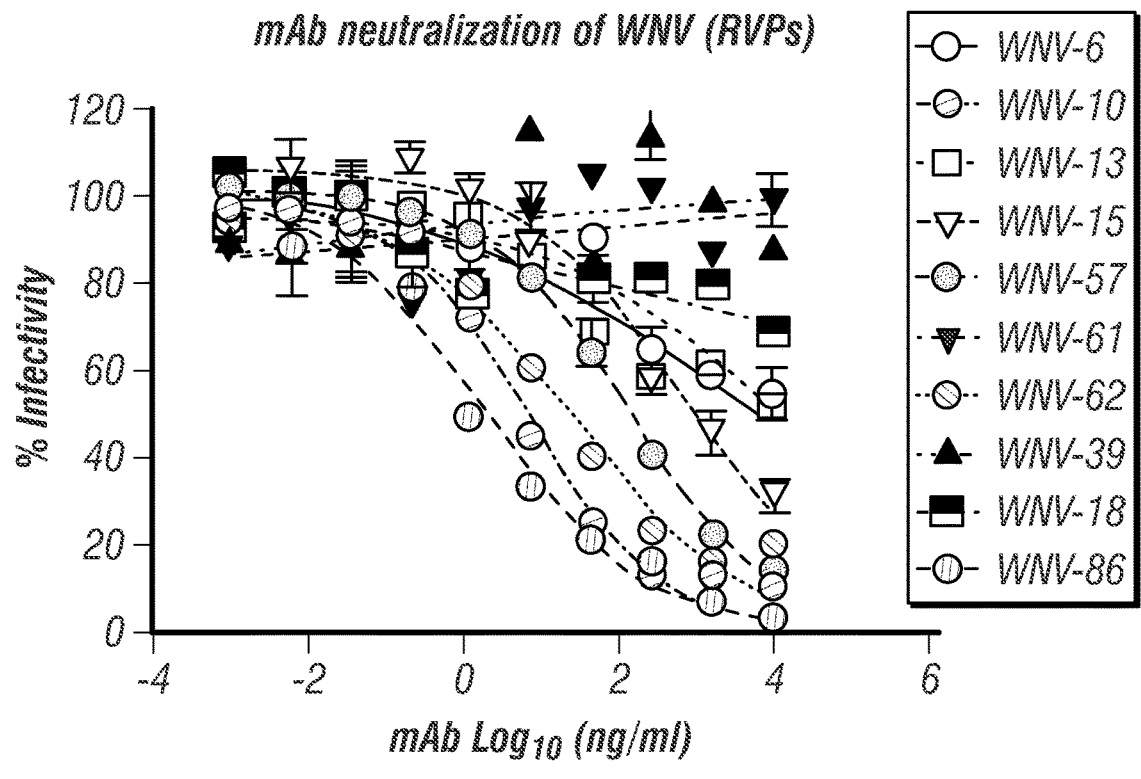

As discussed above, West Nile virus (WNV), a member of the *Flavivirus* genus, is a leading cause of viral encephalitis. No licensed vaccine or therapeutic agent exists to combat WNV infection in humans. The development of neutralizing antibodies against the flavivirus envelope (E) protein is critical for flavivirus immunity and vaccine protection. Previous studies have identified candidate therapeutic neutralizing mouse and human monoclonal antibodies (mAbs) targeting epitopes within the WNV E domain III lateral ridge and the domain I-II hinge region, respectively.

To further explore the neutralizing antibody repertoire elicited by WNV infection for potential therapeutic application, the inventor isolated a panel of 10 mAbs from WNV-infected individuals. The inventor generated a human mAb designated WNV-86 that is one of the most potent neutralizing flavivirus mAbs ever reported, which displayed a WNV neutralizing $IC_{50}$ of 0.02 µg/mL. This mAb targets a novel epitope in E domain II, and preferentially recognizes mature virions lacking an uncleaved form of the chaperone protein prM, unlike most flavivirus-specific antibodies. Selection of WNV-86 neutralization-resistant variant viruses revealed an escape mechanism involving a glycan addition to E domain II that conferred broad resistance to various mAbs. Finally, a single dose of WNV-86 administered two days post-infection completely protected mice from lethal WNV challenge. This study defines a new epitope on the WNV E protein targeted by a potently neutralizing human mAb with high therapeutic potential.

These and other aspects of the disclosure are described in detail below.

I. WEST NILE VIRUS

West Nile fever is a viral infection typically spread by mosquitoes. In about 75% of infections people have few or no symptoms. About 20% of people develop a fever, headache, vomiting, or a rash. In less than 1% of people, encephalitis or meningitis occurs, with associated neck stiffness, confusion, or seizures. Recovery may take weeks to months. The risk of death among those in whom the nervous system is affected is about 10%.

West Nile virus is typically spread by infected mosquitoes. Mosquitoes become infected when they feed on infected birds. Rarely the virus is spread through blood transfusions, organ transplants, or from mother to baby during pregnancy, delivery, or breastfeeding. It otherwise does not spread directly between people. Risks for severe disease include age over 60 and other health problems. Diagnosis is typically based on symptoms and blood tests.

There is no human vaccine. The best method to reduce the risk of infections is avoiding mosquito bites. This may be done by eliminating standing pools of water, such as in old tires, buckets, gutters, and swimming pools. Mosquito repellent, window screens, mosquito nets, and avoiding areas where mosquitoes occur may also be useful. While there is no specific treatment, pain medications may be useful.

WNV occurs in Europe, the Middle East, Africa, India, Asia, Australia, and North America. In the United States thousands of cases are reported a year, with most occurring in August and September. It can occur in outbreaks of disease. The virus was discovered in Uganda in 1937 and was first detected in North America in 1999. Severe disease may also occur in horses and a vaccine for these animals is available. A surveillance system in birds is useful for early detection of a potential human outbreak.

A. Signs and Symptoms

The incubation period for WNV—the amount of time from infection to symptom onset—is typically from between 2 and 15 days. Headache can be a prominent symptom of WNV fever, meningitis, encephalitis, meningoencephalitis, and it may or may not be present in poliomyelitis-like syndrome. Thus, headache is not a useful indicator of neuroinvasive disease.

West Nile fever (WNF), which occurs in 20 percent of cases, is a febrile syndrome that causes flu-like symptoms. Most characterizations of WNF generally describe it as a mild, acute syndrome lasting 3 to 6 days after symptom onset. Systematic follow-up studies of patients with WNF have not been done, so this information is largely anecdotal. In addition to a high fever, headache, chills, excessive sweating, weakness, fatigue, swollen lymph nodes, drowsiness, pain in the joints and flu-like symptoms. Gastrointestinal symptoms that may occur include nausea, vomiting, loss of appetite, and diarrhea. Fewer than one-third of patients develop a rash.

West Nile neuroinvasive disease (WNND), which occurs in less than 1 percent of cases, is when the virus infects the central nervous system resulting in meningitis, encephalitis, meningoencephalitis or a poliomyelitis-like syndrome. Many patients with WNND have normal neuroimaging studies, although abnormalities may be present in various cerebral areas including the basal ganglia, thalamus, cerebellum, and brainstem.

West Nile virus encephalitis (WNE) is the most common neuroinvasive manifestation of WNND. WNE presents with similar symptoms to other viral encephalitis with fever, headaches, and altered mental status. A prominent finding in WNE is muscular weakness (30 to 50 percent of patients with encephalitis, often with lower motor neuron symptoms, flaccid paralysis, and hyporeflexia with no sensory abnormalities.

West Nile meningitis (WNM) usually involves fever, headache, and stiff neck. Pleocytosis, an increase of white blood cells in cerebrospinal fluid, is also present. Changes in consciousness are not usually seen and are mild when present.

West Nile meningoencephalitis is inflammation of both the brain (encephalitis) and meninges (meningitis).

West Nile poliomyelitis (WNP), an acute flaccid paralysis syndrome associated with WNV infection, is less common than WNM or WNE. This syndrome is generally characterized by the acute onset of asymmetric limb weakness or paralysis in the absence of sensory loss. Pain sometimes precedes the paralysis. The paralysis can occur in the absence of fever, headache, or other common symptoms associated with WNV infection. Involvement of respiratory muscles, leading to acute respiratory failure, can sometimes occur.

West-Nile reversible paralysis, Like WNP, the weakness or paralysis is asymmetric. Reported cases have been noted to have an initial preservation of deep tendon reflexes, which is not expected for a pure anterior horn involvement. Disconnect of upper motor neuron influences on the anterior horn cells possibly by myelitis or glutamate excitotoxicity have been suggested as mechanisms. The prognosis for recovery is excellent.

Nonneurologic complications of WNV infection that may rarely occur include fulminant hepatitis, pancreatitis, myocarditis, rhabdomyolysis, orchitis, nephritis, optic neuritis and cardiac dysrhythmias and hemorrhagic fever with coagulopathy. Chorioretinitis may also be more common than previously thought.

Cutaneous manifestations specifically rashes, are not uncommon in WNV-infected patients; however, there is a paucity of detailed descriptions in case reports and there are few clinical images widely available. Punctate erythematous, macular, and papular eruptions, most pronounced on the extremities have been observed in WNV cases and in some cases histopathologic findings have shown a sparse superficial perivascular lymphocytic infiltrate, a manifestation commonly seen in viral exanthems. A literature review provides support that this punctate rash is a common cutaneous presentation of WNV infection.

B. Cause

WNV is one of the Japanese encephalitis antigenic serocomplex of viruses. Image reconstructions and cryoelectron microscopy reveal a 45-50 nm virion covered with a relatively smooth protein surface. This structure is similar to the dengue fever virus; both belong to the genus *Flavivirus* within the family Flaviviridae. The genetic material of WNV is a positive-sense, single strand of RNA, which is between 11,000 and 12,000 nucleotides long; these genes encode seven nonstructural proteins and three structural proteins. The RNA strand is held within a nucleocapsid formed from 12-kDa protein blocks; the capsid is contained within a host-derived membrane altered by two viral glycoproteins.

The prime method of spread of the West Nile virus (WNV) is the female mosquito. Only female feeds on blood. In Europe, cats were identified as being hosts for West Nile virus. The important mosquito vectors vary according to area; in the United States, *Culex pipiens* (Eastern United States, and urban and residential areas of the United States north of 36-39° N), *Culex tarsalis* (Midwest and West), and *Culex quinquefasciatus* (Southeast) are the main vector species.

The mosquito species that are most frequently infected with WNV feed primarily on birds. Different species of mosquitos take a blood meal from different types of vertebrate hosts, Mosquitoes show further selectivity, exhibiting preference for different species of birds. In the United States, WNV mosquito vectors feed preferentially on members of the Corvidae and thrush family. Among the preferred species within these families are the American crow, a corvid, and the American robin (*Turdus migratorius*).

Some species of birds develop sufficient viral levels ($>\sim10^{4.2}$ log PFU/ml) after being infected to transmit the infection to biting mosquitoes that in turn go on to infect other birds. In birds that die from WNV, death usually occurs after 4 to 6 days. In mammals and several species of birds, the virus does not multiply as readily and so does not develop high viremia during infection. Mosquitoes biting such hosts are not believed to ingest sufficient virus to become infected, making them so-called dead-end hosts. As a result of the differential infectiousness of hosts, the feeding patterns of mosquitoes play an important role in WNV transmission, and they are partly genetically controlled, even within a species.

Direct human-to-human transmission initially was believed to be caused only by occupational exposure, such as in a laboratory setting, or conjunctive exposure to infected blood. The US outbreak identified additional transmission methods through blood transfusion, organ transplant, intrauterine exposure, and breast feeding. Since 2003, blood banks in the United States routinely screen for the virus among their donors. As a precautionary measure, the UK's National Blood Service initially ran a test for this disease in donors who donate within 28 days of a visit to the United States, Canada, or the northeastern provinces of Italy, and the Scottish National Blood Transfusion Service asks prospective donors to wait 28 days after returning from North America or the northeastern provinces of Italy before donating. There also have been reports of possible transmission of the virus from mother to child during pregnancy or breast-feeding or exposure to the virus in a lab, but these are rare cases and not conclusively confirmed.

Recently, the potential for mosquito saliva to affect the course of WNV disease was demonstrated. Mosquitoes inoculate their saliva into the skin while obtaining blood. Mosquito saliva is a pharmacological cocktail of secreted molecules, principally proteins, that can affect vascular constriction, blood coagulation, platelet aggregation, inflammation, and immunity. It clearly alters the immune response in a manner that may be advantageous to a virus. Studies have shown it can specifically modulate the immune response during early virus infection, and mosquito feeding can exacerbate WNV infection, leading to higher viremia and more severe forms of disease.

Vertical transmission, the transmission of a viral or bacterial disease from the female of the species to her offspring, has been observed in various West Nile virus studies, amongst different species of mosquitoes in both the laboratory and in nature. Mosquito progeny infected vertically in autumn, may potentially serve as a mechanism for WNV to overwinter and initiate enzootic horizontal transmission the following spring, although it likely plays little role in transmission in the summer and fall.

Risk factors independently associated with developing a clinical infection with WNV include a suppressed immune system and a patient history of organ transplantation. For neuroinvasive disease the additional risk factors include older age (>50+), male sex, hypertension, and diabetes mellitus.

A genetic factor also appears to increase susceptibility to West Nile disease. A mutation of the gene CCR5 gives some protection against HIV but leads to more serious complications of WNV infection. Carriers of two mutated copies of CCR5 made up 4.0 to 4.5% of a sample of West Nile disease sufferers, while the incidence of the gene in the general population is only 1.0%.

C. Diagnosis

Preliminary diagnosis is often based on the patient's clinical symptoms, places and dates of travel (if patient is from a non-endemic country or area), activities, and epidemiologic history of the location where infection occurred. A recent history of mosquito bites and an acute febrile illness associated with neurologic signs and symptoms should cause clinical suspicion of WNV.

Diagnosis of West Nile virus infections is generally accomplished by serologic testing of blood serum or cerebrospinal fluid (CSF), which is obtained via a lumbar puncture. Initial screening could be done using the ELISA technique detecting immunoglobulins in the sera of the tested individuals.

Typical findings of WNV infection include lymphocytic pleocytosis, elevated protein level, reference glucose and lactic acid levels, and no erythrocytes.

Definitive diagnosis of WNV is obtained through detection of virus-specific antibody IgM and neutralizing antibodies. Cases of West Nile virus meningitis and encephalitis that have been serologically confirmed produce similar degrees of CSF pleocytosis and are often associated with substantial CSF neutrophilia. Specimens collected within eight days following onset of illness may not test positive for West Nile IgM, and testing should be repeated. A positive test for West Nile IgG in the absence of a positive West Nile IgM is indicative of a previous flavavirus infection and is not by itself evidence of an acute West Nile virus infection.

If cases of suspected West Nile virus infection, sera should be collected on both the acute and convalescent phases of the illness. Convalescent specimens should be collected 2-3 weeks after acute specimens.

It is common in serologic testing for cross-reactions to occur among flaviviruses such as dengue virus (DENV) and tick-borne encephalitis virus; this necessitates caution when evaluating serologic results of flaviviral infections.

Four FDA-cleared WNV IgM ELISA kits are commercially available from different manufacturers in the U.S., each of these kits is indicated for use on serum to aid in the presumptive laboratory diagnosis of WNV infection in patients with clinical symptoms of meningitis or encephalitis. Positive WNV test results obtained via use of these kits should be confirmed by additional testing at a state health department laboratory or CDC.

In fatal cases, nucleic acid amplification, histopathology with immunohistochemistry, and virus culture of autopsy tissues can also be useful. Only a few state laboratories or other specialized laboratories, including those at CDC, are capable of doing this specialized testing.

A number of various diseases may present with symptoms similar to those caused by a clinical West Nile virus infection. Those causing neuroinvasive disease symptoms include the enterovirus infection and bacterial meningitis. Accounting for differential diagnoses is a crucial step in the definitive diagnosis of WNV infection. Consideration of a differential diagnosis is required when a patient presents with unexplained febrile illness, extreme headache, encephalitis or meningitis. Diagnostic and serologic laboratory testing using polymerase chain reaction (PCR) testing and viral culture of CSF to identify the specific pathogen causing the symptoms, is the only currently available means of differentiating between causes of encephalitis and meningitis.

D. Prevention

Personal protective measures can be taken to greatly reduce the risk of being bitten by an infected mosquito:

- Using insect repellent on exposed skin to repel mosquitoes. EPA-registered repellents include products containing DEET (N,N-diethylmetatoluamide) and picaridin (KBR 3023). DEET concentrations of 30% to 50% are effective for several hours. Picaridin, available at 7% and 15% concentrations, needs more frequent application. DEET formulations as high as 30% are recommended for children over two months of age. Protect infants less than two months of age by using a carrier draped with mosquito netting with an elastic edge for a tight fit.
- When using sunscreen, apply sunscreen first and then repellent. Repellent should be washed off at the end of the day before going to bed.
- Wear long-sleeve shirts, which should be tucked in, long pants, socks, and hats to cover exposed skin. Insect repellents should be applied over top of protective clothing for greater protection. Do not apply insect repellents underneath clothing.
- The application of permethrin-containing (e.g., Permanone) or other insect repellents to clothing, shoes, tents, mosquito nets, and other gear for greater protection. Permethrin is not labeled for use directly on skin. Most repellent is generally removed from clothing and gear by a single washing, but permethrin-treated clothing is effective for up to five washings.
- Be aware that most mosquitoes that transmit disease are most active during twilight periods (dawn and dusk or in the evening). A notable exception is the Asian tiger mosquito, which is a daytime feeder and is more apt to be found in, or on the periphery of, shaded areas with heavy vegetation. They are now widespread in the United States, and in Florida they have been found in all 67 counties.

Staying in air-conditioned or well-screened housing, and/or sleeping under an insecticide-treated bed net. Bed nets should be tucked under mattresses and can be sprayed with a repellent if not already treated with an insecticide.

Personal protective measures can be taken to greatly reduce the risk of being bitten by an infected mosquito:

Using insect repellent on exposed skin to repel mosquitoes. EPA-registered repellents include products containing DEET (N,N-diethylmetatoluamide) and picaridin (KBR 3023). DEET concentrations of 30% to 50% are effective for several hours. Picaridin, available at 7% and 15% concentrations, needs more frequent application. DEET formulations as high as 30% are recommended for children over two months of age. Protect infants less than two months of age by using a carrier draped with mosquito netting with an elastic edge for a tight fit.

When using sunscreen, apply sunscreen first and then repellent. Repellent should be washed off at the end of the day before going to bed.

Wear long-sleeve shirts, which should be tucked in, long pants, socks, and hats to cover exposed skin. Insect repellents should be applied over top of protective clothing for greater protection. Do not apply insect repellents underneath clothing.

The application of permethrin-containing (e.g., Permanone) or other insect repellents to clothing, shoes, tents, mosquito nets, and other gear for greater protection. Permethrin is not labeled for use directly on skin. Most repellent is generally removed from clothing and gear by a single washing, but permethrin-treated clothing is effective for up to five washings.

Be aware that most mosquitoes that transmit disease are most active during twilight periods (dawn and dusk or in the evening). A notable exception is the Asian tiger mosquito, which is a daytime feeder and is more apt to be found in, or on the periphery of, shaded areas with heavy vegetation. They are now widespread in the United States, and in Florida they have been found in all 67 counties.

Staying in air-conditioned or well-screened housing, and/or sleeping under an insecticide-treated bed net. Bed nets should be tucked under mattresses and can be sprayed with a repellent if not already treated with an insecticide.

West Nile virus can be sampled from the environment by the pooling of trapped mosquitoes via ovitraps, carbon dioxide-baited light traps, and gravid traps, testing blood samples drawn from wild birds, dogs, and sentinel monkeys, as well as testing brains of dead birds found by various animal control agencies and the public.

Testing of the mosquito samples requires the use of reverse-transcriptase PCR (RT-PCR) to directly amplify and show the presence of virus in the submitted samples. When using the blood sera of wild birds and sentinel chickens, samples must be tested for the presence of WNV antibodies by use of immunohistochemistry (IHC) or enzyme-linked immunosorbent assay (ELISA).

Dead birds, after necropsy, or their oral swab samples collected on specific RNA-preserving filter paper card, can have their virus presence tested by either RT-PCR or IHC, where virus shows up as brown-stained tissue because of a substrate-enzyme reaction.

West Nile control is achieved through mosquito control, by elimination of mosquito breeding sites such as abandoned pools, applying larvacide to active breeding areas, and targeting the adult population via lethal ovitraps and aerial spraying of pesticides.

Environmentalists have condemned attempts to control the transmitting mosquitoes by spraying pesticide, saying the detrimental health effects of spraying outweigh the relatively few lives that may be saved, and more environmentally friendly ways of controlling mosquitoes are available. They also question the effectiveness of insecticide spraying, as they believe mosquitoes that are resting or flying above the level of spraying will not be killed; the most common vector in the northeastern United States, *Culex pipiens*, is a canopy feeder.

E. Treatment and Prognosis

Most people recover from West Nile virus without treatment. No specific treatment is available for WNV infection. In mild cases over the counter pain relievers can help ease mild headaches and muscle aches in adults. In severe cases treatment consists of supportive care that often involves hospitalization, intravenous fluids, pain medication, respiratory support, and prevention of secondary infections.

While the general prognosis is favorable, current studies indicate that West Nile Fever can often be more severe than previously recognized, with studies of various recent outbreaks indicating that it may take as long as 60-90 days to recover. People with milder WNF are just as likely as those with more severe manifestations of neuroinvasive disease to experience multiple long term (>1+ years) somatic complaints such as tremor, and dysfunction in motor skills and executive functions. People with milder illness are just as likely as people with more severe illness to experience adverse outcomes. Recovery is marked by a long convalescence with fatigue. One study found that neuroinvasive WNV infection was associated with an increased risk for subsequent kidney disease.

II. MONOCLONAL ANTIBODIES AND PRODUCTION THEREOF

A. General Methods

It will be understood that monoclonal antibodies binding to West Nile virus will have several applications. These include the production of diagnostic kits for use in detecting and diagnosing West Nile virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies were generated by subcloning heavy and light chain Fv DNAs from the cloning vector into an IgG plasmid vector, transfected into 293 Freestyle cells or CHO cells, and antibodies were collected and purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Beltramello et al. (2010) previously reported the modification of neutralizing mAbs, due to their tendency to enhance DV infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four DENV serotypes. LALA variants retained the same neutralizing activity as unmodified mAbs but were completely devoid of enhancing activity. LALA or N297 mutations of this nature are therefore contemplated in the context of the presently disclosed antibodies.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed.

Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amounts of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF WEST NILE VIRUS INFECTION

A. Formulation and Administration

The present disclosure provides pharmaceutical compositions comprising anti-West Nile virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of West Nile virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety.

Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting West Nile virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Other immunodections methods include specific assays for determining the presence of West Nile virus in a subject. A wide variety of assay formats are contemplated, but specifically those that would be used to detect West Nile virus in a fluid obtained from a subject, such as saliva, blood, plasma, sputum, semen or urine. In particular, semen has been demonstrated as a viable sample for detecting West Nile virus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may advantageously for formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of West Nile virus antibodies directed to specific parasite epitopes in samples also is provided. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample suspected of containing West Nile virus, and contacting the sample with a first antibody in accordance with the present disclosure, as the case may be, under conditions effective to allow the formation of immunocomplexes.

These methods include methods for purifying West Nile virus or related antigens from a sample. The antibody will preferably be linked to a solid support, such as in the form of a column matrix, and the sample suspected of containing the West Nile virus or antigenic component will be applied to the immobilized antibody. The unwanted components will be washed from the column, leaving the West Nile virus antigen immunocomplexed to the immobilized antibody, which is then collected by removing the organism or antigen from the column.

The immunobinding methods also include methods for detecting and quantifying the amount of West Nile virus or related components in a sample and the detection and quantification of any immune complexes formed during the binding process. Here, one would obtain a sample suspected of containing West Nile virus or its antigens and contact the sample with an antibody that binds West Nile virus or components thereof, followed by detecting and quantifying the amount of immune complexes formed under the specific conditions. In terms of antigen detection, the biological sample analyzed may be any sample that is suspected of containing West Nile virus or West Nile virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to West Nile virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the West Nile virus or West Nile virus antigen is added to the wells. After binding and washing to remove non-specifically bound immune complexes, the bound antigen may be detected. Detection may be achieved by the addition of another anti-West Nile virus antibody that is linked to a detectable label. This type of ELISA is a simple "sandwich ELISA." Detection may also be achieved by the addition of a second anti-West Nile virus antibody, followed by the addition of a third antibody that has binding affinity for the second antibody, with the third antibody being linked to a detectable label.

In another exemplary ELISA, the samples suspected of containing the West Nile virus or West Nile virus antigen are immobilized onto the well surface and then contacted with the anti-West Nile virus antibodies of the disclosure. After binding and washing to remove non-specifically bound immune complexes, the bound anti-West Nile virus antibodies are detected. Where the initial anti-West Nile virus antibodies are linked to a detectable label, the immune complexes may be detected directly. Again, the immune complexes may be detected using a second antibody that has binding affinity for the first anti-West Nile virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of West Nile virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled West Nile virus monoclonal antibodies to determine the amount of West Nile virus antibodies in a sample. The basic format would include contacting a known amount of West Nile virus monoclonal antibody (linked to a detectable label) with West Nile virus antigen or particle. The West Nile virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many lab-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect West Nile virus or West Nile virus antigens, the antibodies may be included in the kit. The immunodetection kits will thus comprise, in suitable container means, a first antibody that binds to West Nile virus or West Nile virus antigen, and optionally an immunodetection reagent.

In certain embodiments, the West Nile virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the West Nile virus or West Nile virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Human subjects. Blood samples were obtained in 2014 from adult subjects with history of symptomatic laboratory-confirmed WNV infection during the 2012 West Nile encephalitis epidemic in Dallas, Texas. The studies were approved by the Institutional Review Board of Vanderbilt University Medical Center; samples were obtained after informed consent was obtained by the Vanderbilt Clinical Trials Center.

Generation of anti-E monoclonal antibodies. Peripheral blood mononuclear cells (PBMC) were isolated from heparinized blood by gradient centrifugation after layering on Ficoll Histopaque and cryopreserved in the vapor phase of liquid nitrogen till use. B cells were transformed by infection with Epstein Barr virus (EBV) obtained from the supernatant of cultured B95.8 cotton top tamarin lymphoblastoid line (ATCC). The transformation medium contained 2.5 µg/mL TLR agonist CpG (phosphorothioate-modified oligodeoxynucleotide ZOEZOEZZZZZOEEZOEZZZT, Life Technologies), 10 µM Chk2 inhibitor [Chk2i] (Sigma), and 10 µg/mL cyclosporine A (Sigma). B cells were plated in 384-well culture plates and cultured for 7 days and then expanded into four 96-well culture plates containing CpG, Chk2i and irradiated heterologous human PBMCs to serve as feeder layers for the growth of lymphoblastoid cell line (LCL) clusters. After an additional three days of culture, the supernatants were screened for binding to recombinant WNV E protein by ELISA. About 5 µL volume of supernatant from each well of transformed B cell cultures (in a total assay volume of 50 µL) were added to wells coated with 2 µg/mL of recombinant WNV E protein. The bound antibodies were detected using alkaline phosphatase conjugated goat anti-human Ig (γ-chain specific) (Southern Biotech).

Cells from wells positive for binding to WNV E were subjected to electrofusion with HMMA2.5 myeloma cells (Yu et al., 2008). The fused cells then were cultured in a selective medium containing 100 µM hypoxanthine, 0.4 µM aminopterin, 16 µM thymidine (HAT Media Supplement, Sigma HO262), and 7 µg/mL ouabain (Sigma O3125) and incubated for 14-18 days before screening hybridomas for antibody production by ELISA using recombinant WNV E protein. Cells from positive wells were cloned biologically by sorting single cells into 384-well plates using a FACSAria III fluorescence-activated cell sorter (Becton Dickinson), cultured for about 14 days and screened for specific antibody production by ELISA using WNV E protein. For expression of antibodies from hybridoma clones, cells were cultured in serum-free medium, Hybridoma SFM (Life Technologies), for 21 days. Antibodies were harvested from the supernatants by affinity chromatography on HiTrap MabSelect SuRe columns (Life Technologies) according to the manufacturer's instructions. Antibodies eluted from affinity columns were concentrated using Amicon centrifugal filters (Millipore).

Cells. Raji B lymphoblast cells (ATCC) engineered to stably express DC-SIGNR (Raji-DCSIGNR) (Davis et al., 2006) were cultured in RPMI 1640 medium containing Glutamax (Invitrogen) supplemented with 7% FBS and 100 U/mL P/S. HEK-293T (ATCC) and Vero (ATCC) cells were maintained in Dulbecco's Modified Eagle medium (DMEM) containing 25 mM HEPES (Invitrogen) supplemented with 7% fetal bovine serum (FBS; Invitrogen) and 100 U/mL penicillin-streptomycin (P/S; Invitrogen). All cells were maintained at 37° C. in the presence of 7% $CO_2$.

Generation of plasmids encoding E protein variants. A previously described expression vector encoding the structural genes (C-prM-E) of the WNV1 NY99 strain (Pierson et al., 2006) as a template for site-directed mutagenesis using the Pfu Ultra DNA polymerase system (Agilent Technologies, Santa Clara, CA). PCR cycling parameters were: 1 cycle of 95° C. for 1 min; 18 cycles of 95° C. for 50 s, 60° C. for 50 s, and 68° C. for 9 min; and 1 cycle of 68° C. for 7 min. Following digestion with DpnI (New England Biolabs, Ipswich, MA) for 3 h at 37° C., PCR products were used to transform Stbl2 cells (Invitrogen, Carlsbad, CA) propagated at 30° C. After confirming the presence of the desired mutation by sequencing, the entire C-prM-E region was sequenced to ensure that no additional mutations were present.

Production of RVPs. RVPs were produced by co-transfection of a plasmid expressing a WNV subgenomic replicon in which the structural genes have been replaced with GFP and plasmids encoding structural gene variants, as described previously (Pierson et al., 2006; Ansarah-Sobrinho et al., 2008; Dowd et al., 2016). Briefly, HEK-293T cells were pre-plated in a low-glucose (1 g/L) formulation of DMEM containing 25 mM HEPES (Invitrogen), 7% FBS, and 100 U/mL P/S and transfected with plasmids encoding the replicon and structural genes at a 1:3 ratio by mass using Lipofectamine 3000 (Invitrogen) and incubated at 37° C. Four hours post-transfection, cells were transferred to 30° C. Supernatant was harvested at days 3 and 4 post-transfection, pooled, passed through a 0.22 µm filter (Millipore), and stored at −80° C. To prepare mature RVPs with increased efficiency of prM cleavage, RVPs were produced by co-transfecting plasmids encoding the replicon, structural genes, and human furin at a 1:3:1 ratio. Immature RVPs with decreased prM cleavage efficiency was produced in cells treated with 20 mM NH4Cl, as described previously (Nelson et al., 2008).

Production of fully infectious WNV. A DNA fragment encoding WT WNV structural genes or WNV structural genes encoding a mutation at E residue 64 introduced by site-directed mutagenesis was ligated into a GFP-expressing WNV "backbone" replicon plasmid (pWNV-GFP-backbone V3) and transfected directly into HEK-293T cells to generate infectious virus particles, as described previously (Lin et al., 2012). Briefly, 1 µg each of the backbone and structural gene plasmids were digested with BamHI and BssHIII and ligated with T4 DNA ligase (New England Biolabs) at 16° C. overnight in a final volume of 40 µl. The entire unpurified ligation mixture was transfected into HEK-293T cells using Lipofectamine 3000 (Invitrogen) according to manufacturer's instructions. Cells were incubated at 37° C. in the presence of 7% $CO_2$. Viral supernatant was harvested at 3 days post-transfection, filtered using a 0.22 μm filter (Millipore), and stored at −80° C.

Determination of virus titer. Virus-containing supernatant was serially diluted 2-fold in a total volume of 100 μl and used to infect $5 \times 10^4$ Raji-DC-SIGNR cells in an equal volume at 37° C. Cells were fixed in 1.8% paraformaldehyde at 48 h or 16 h following infection by RVPs or fully infectious virus, respectively, and GFP-positive cells were enumerated using flow cytometry. Infectious titre was calculated using the linear portion of the resulting dose-response infectivity curve using the following formula: Infectious units (IU) per virus volume=(% GFP-positive cells)×(dilution factor)×(number of cells)

Neutralization assays. RVP or fully infectious virus stocks were diluted to a level of infectivity (~5-10%) and incubated with serial dilutions of mAbs for 1 h at room temperature before addition of Raji-DC-SIGNR cells. All infections were performed in duplicate at 37° C. At 48 h (RVP) or 16 h (fully infectious virus) post-infection, infectivity was measured as a percentage of GFP-positive cells by flow cytometry. Antibody dose-response curves were analyzed using non-linear regression with a variable slope (GraphPad Prism v 6.0 g, GraphPad Software Inc.) to estimate the reciprocal serum dilution (NT50) or concentration of antibody ($IC_{50}$) required to inhibit infection by 50%.

Selection of neutralization escape variants. Fully infectious GFP-expressing WNV (Lin et al., 2102) was incubated with mAb WNV-86 (0.6 μg/mL for WT; 2 μg/mL for WNV T64Q) in a total volume of 2 mL for 30 min at 37° C., followed by duplicate infection of pre-plated Vero cells ($8.5 \times 10^5$/well) in a 6-well dish at a MOI of 0.1. After 3-4 days of infection at 37° C., continuous viral replication and antibody selection pressures were maintained by serial passaging of virus supernatant diluted 1:10 in media with or without WNV-86 in a total volume of 2 mL and incubated for 30 min at 37° C. prior to addition to fresh Vero cells. The remaining volume of virus supernatant was aliquoted and stored at −80° C. until further use. Replication of antibody escape viral variants was monitored by visually inspecting cells for GFP expression and confirmed by infecting Raji-DCSIGNR cells with an aliquot of the virus supernatant (serially diluted 2-fold) in the presence or absence of a neutralizing concentration (2 μg/mL) of WNV-86, and by neutralization assays as described above. Following confirmation of mAb escape, viral RNA was isolated from a 50 μl aliquot of viral supernatant (adjusted to 140 μL using RNase-free water) using the QIAamp viral RNA mini kit (QIAGEN) according to the manufacturer's instructions. cDNA encoding WNV structural genes was amplified using the SuperScript III One-Step RT-PCR system (Invitrogen). The structural genes were sequenced directly from the gel-purified PCR product and were compared to the structural gene sequence of WNV passaged in parallel in the absence of antibody to identify mAb escape mutations.

Measurement of monoclonal antibody binding to recombinant E proteins. Monoclonal antibody binding to WNV was measured by ELISA, as described previously (Oliphant et al., 2007). Briefly, recombinant full length WNV E protein or DIII was diluted to 5 μg/mL in 0.1 M sodium carbonate buffer (pH 9.3) and adsorbed on 96-well MaxiSorp microtiter plates overnight at 4° C. After blocking with phosphate-buffered saline (PBS) containing 2% bovine serum albumin (BSA) and 0.05% Tween 20 (PBS-BT) for 1 h at 37° C., three-fold serial dilutions of antibody in PBS-BT were incubated for 1 h at room temperature. Plates were washed with PBS plus 0.05% Tween 20 and incubated with biotin-conjugated goat anti-mouse IgG (1 μg/mL; Sigma-Aldrich) for 1 h at room temperature. After being washed, all plates were incubated with streptavidin-horseradish peroxidase (2 μg/mL; Zymed) for 1 h at room temperature and developed with tetramethylbenzidine substrate (Dako). After the addition of 1 N $H_2SO_4$, the optical density at 450 nm was measured. Best-fit lines were fit using GraphPad Prism v 6.0 g (GraphPad Software, Inc).

Mouse experiments. Five-week old C57BL/6J mice (Jackson Laboratories, Cat #000644) were inoculated subcutaneously with 100 focus forming units (FFU) of WNV NY99 after anaesthetization with xylazine and ketamine. Two days post-infection, mice were given 100 μg of mAb via intraperitoneal injection and monitored for survival for 30 days. Mouse experiments were approved and performed according to the guidelines of the Washington University School of Medicine Institutional Animal Care and Use Committee (IACUC) (Assurance Number: A3381-01).

Statistical analysis. All data were analysed in GraphPad Prism v 6.0 g (GraphPad Software Inc.) and expressed as mean values and their standard error (SEM). P-values were calculated using paired t-tests or the log-rank test, as indicated.

Example 2—Results

Figure 1D:
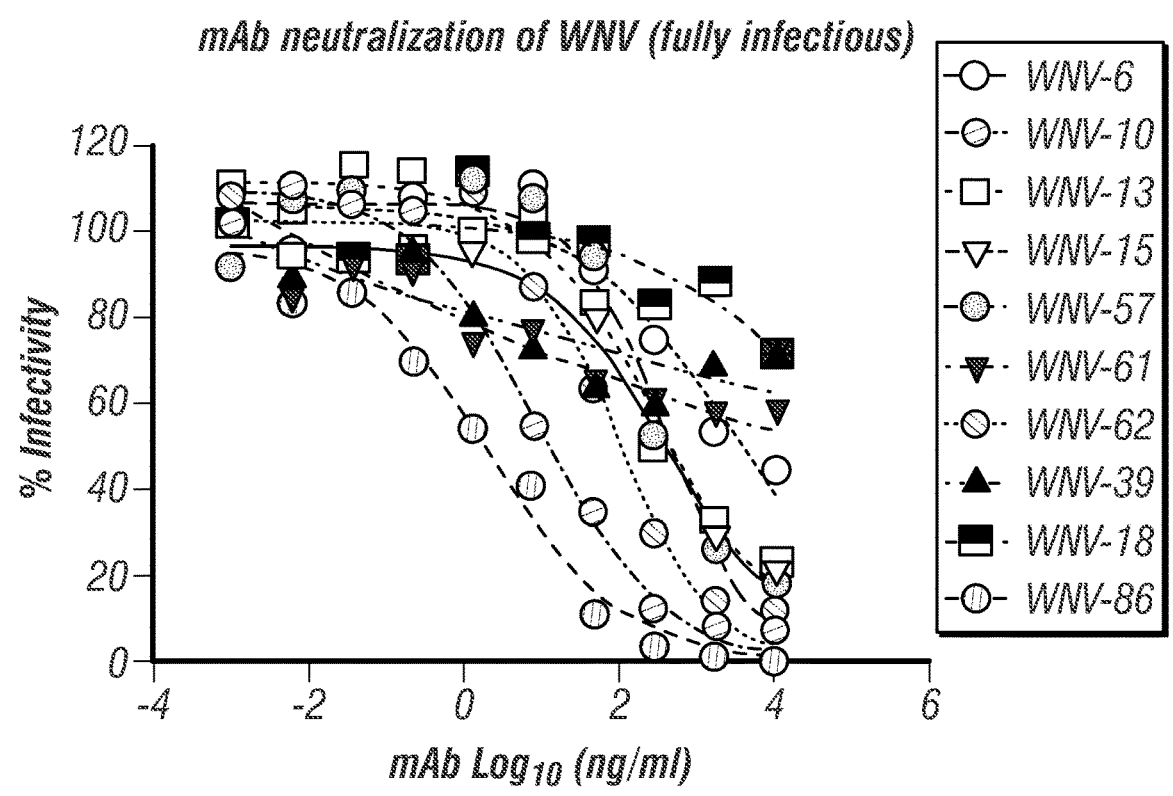

Isolation of human monoclonal antibodies against WNV. The inventor obtained 13 serum samples from individuals in Dallas, TX who had a history of prior laboratory-confirmed symptomatic WNV infection that occurred during the 2012 epidemic. The serum samples were screened for neutralizing activity against WNV pseudo-infectious reporter virus particles (RVPs) (Pierson et al., 2006) (FIGS. 1A-B) and estimated the reciprocal serum dilution that inhibited infectivity by 50% ($NT_{50}$). These samples displayed a range of neutralizing activities (median $NT_{50}$ of 1,504; range of 215 to 5,365), with sera from 9 out of 13 donors displaying potent neutralization (average $NT_{50}$>1,000). To characterize the antibodies that mediated serum neutralization, the inventor selected B cells from three donors (subjects 865, 866, and 870) with potent serum neutralizing activity (average $NT_{50}$ values of 5,341, 1,504, and 5,365, respectively) for EBV transformation and monoclonal antibody production. The frequency of WNV E protein-specific EBV-transformed B cells was similar for these three donors (0.9% for 865; 1.1% for 855; and 0.7% for 870). Following hybridoma fusion and single cell sorting (Smith et al., 2012), 10 antibody-secreting hybridoma clones were recovered. Of these 10 mAbs, three (WNV-61, WNV-39, WNV-18) displayed undetectable neutralizing activity against WNV RVPs, and another three (WNV-6, WNV-13, WNV-15) had modest neutralizing activity, with a large fraction (30% to 50%) of RVPs remaining infectious at the highest mAb concentration tested (10 μg/mL, FIGS. 1C and 1E). The remaining four mAbs (WNV-10, WNV-57, WNV-62, WNV-86) strongly neutralized WNV RVPs (average $IC_{50}$ values of 20, 336, 91, or 2 ng/mL, respectively, FIGS. 1C and 1E) and were chosen for further characterization. MAb WNV-86 displayed particularly remarkable potency, exceeding that of the mouse or humanized form of the therapeutic mAb E16 (Oliphant et al., 2005; Pierson et al., 2007). Because RVPs are made by genetic complementation and are only capable of a single round of infection, the neutralization profiles of these mAbs also were confirmed in neutralization assays using fully infectious WNV, with similar results (FIGS. 1D and 1F).

Figure 7A:
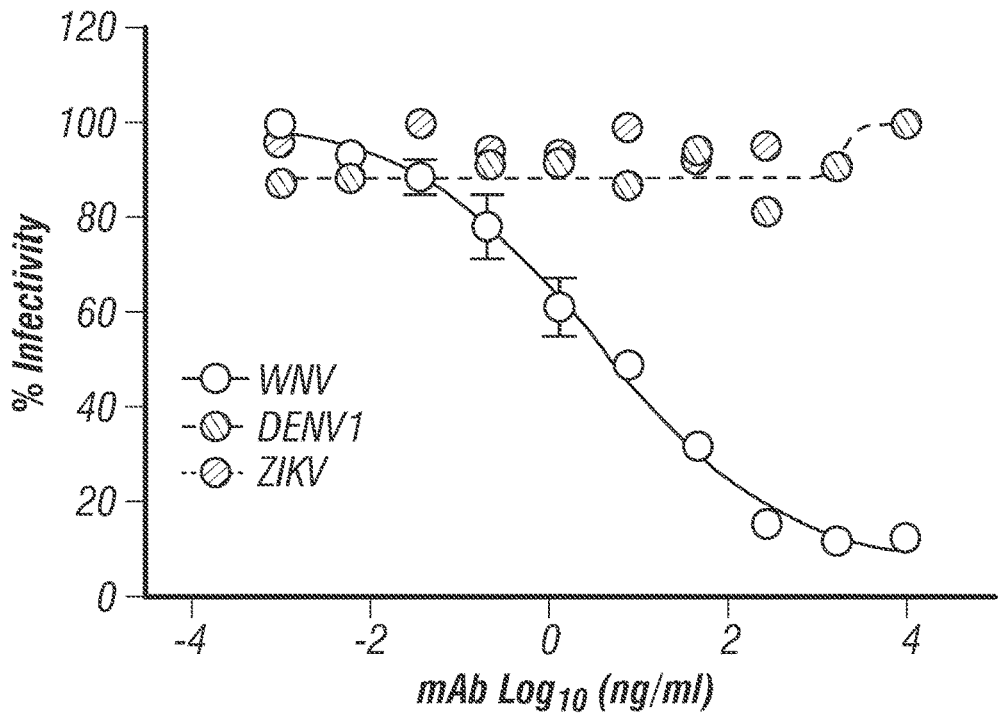
FIGS. 7A-D. MAb cross-reactivity against flaviviruses. Standard preparations of WNV, DENV1, or ZIKV RVPs were tested for sensitivity to neutralization by mAbs (FIG. 7A) WNV-10, (FIG. 7B) WNV-57, (FIG. 7C) WNV-62, or (FIG. 7D) WNV-86. Dose-response curves representative of three independent experiments are shown. Infectivity was normalized to levels observed in the absence of antibody. Error bars indicate the range of duplicate infections.
Figure 7B:
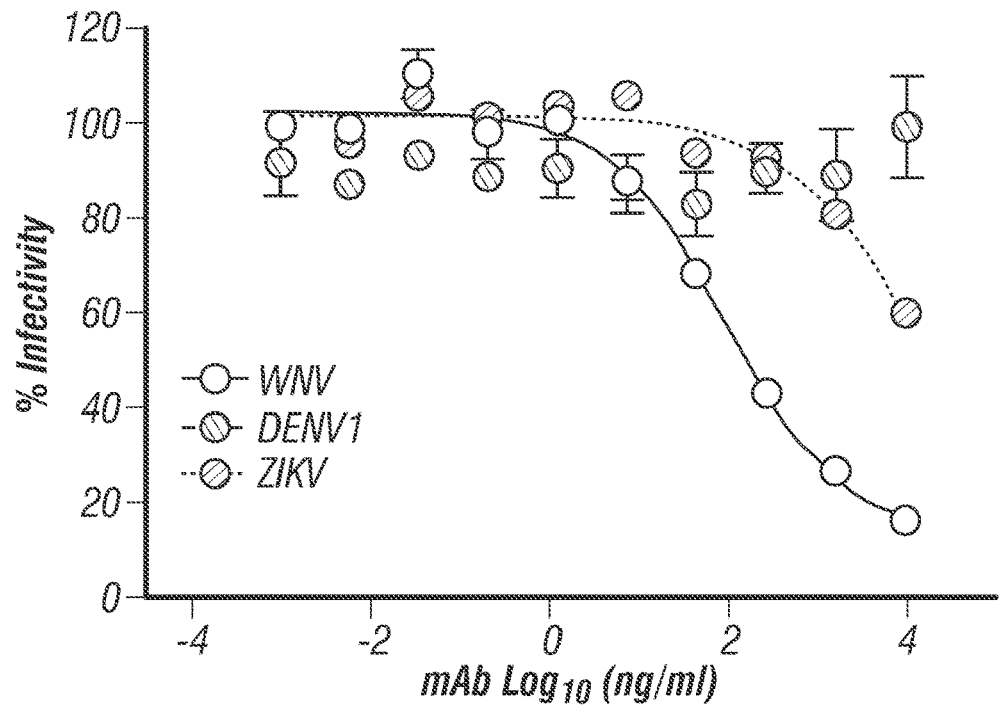
Figure 7C:
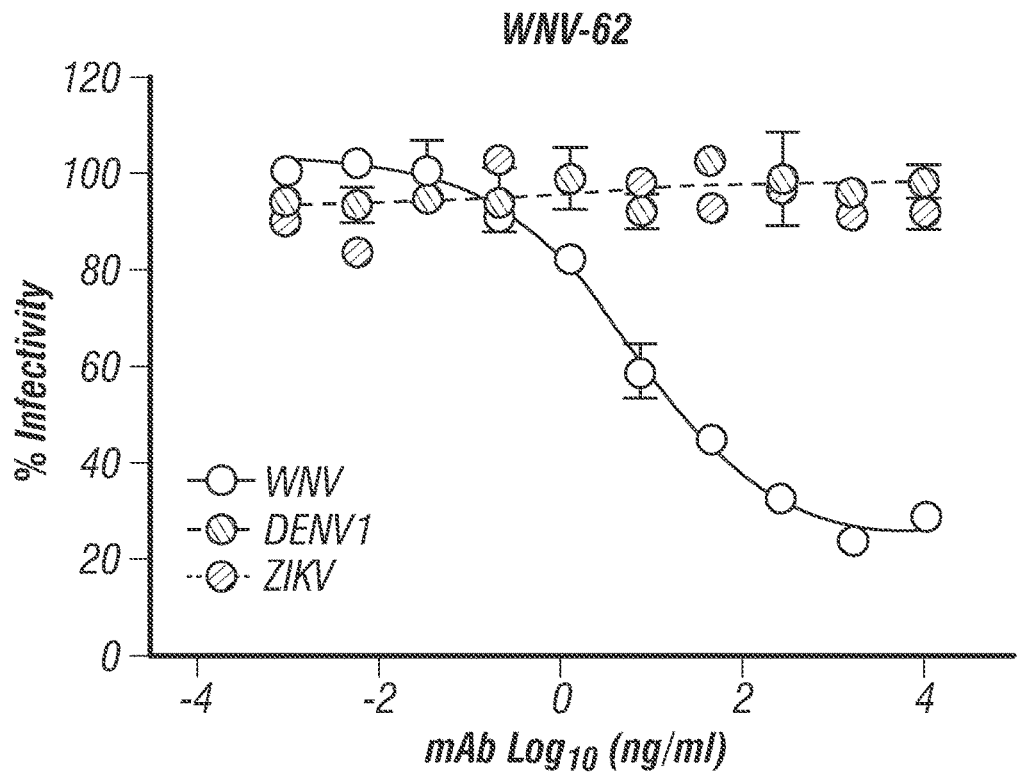
Figure 7D:
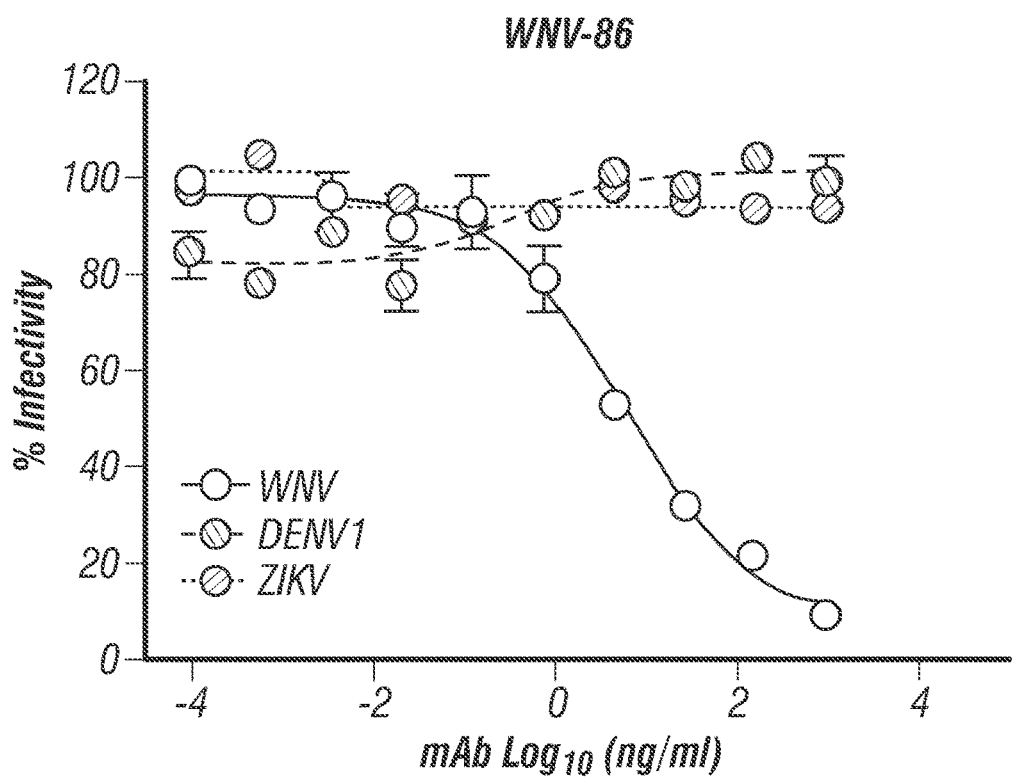

To determine whether mAbs that strongly neutralize WNV also could inhibit related flaviviruses, they were screened for the ability to neutralize the Western Pacific strain of dengue virus serotype 1 (DENV1) or the H/PF/2013 strain of Zika virus (ZIKV). All four mAbs tested displayed little or no cross-neutralization of DENV1 or ZIKV (FIGS. A-D). MAb WNV-57 very weakly neutralized ZIKV with an $IC_{50}$>10 μg/mL (FIG. 7B). Thus, the screen of B cells from WNV-infected individuals identified potently neutralizing antibodies that were mostly WNV-specific.

Figure 2A:
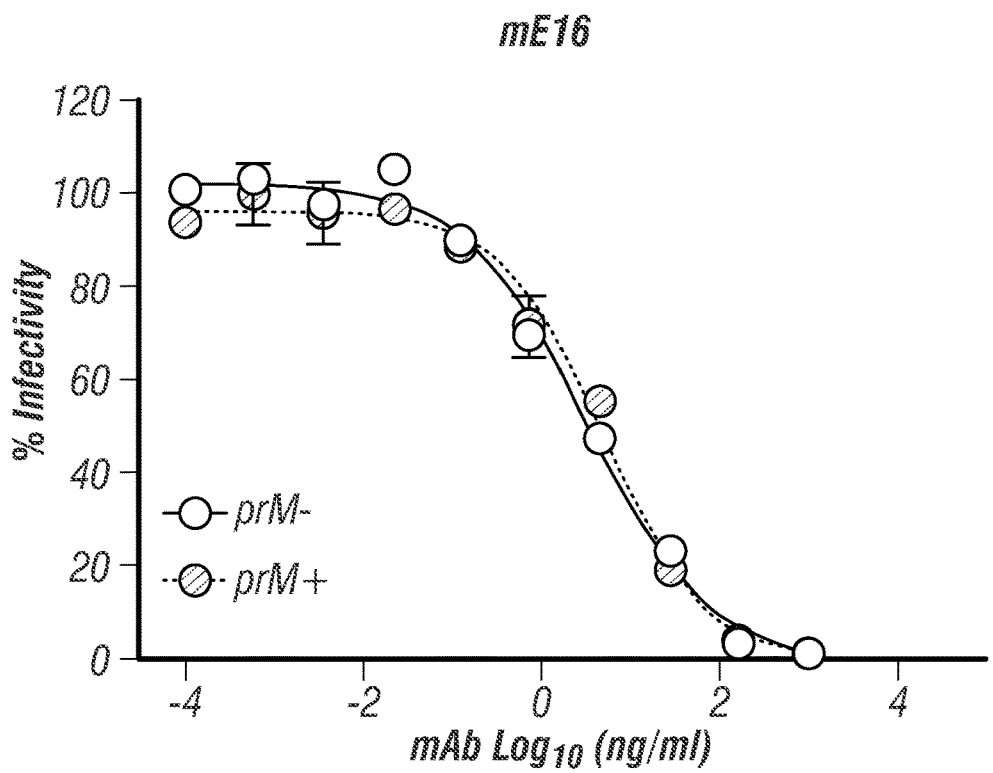
Figure 2B:
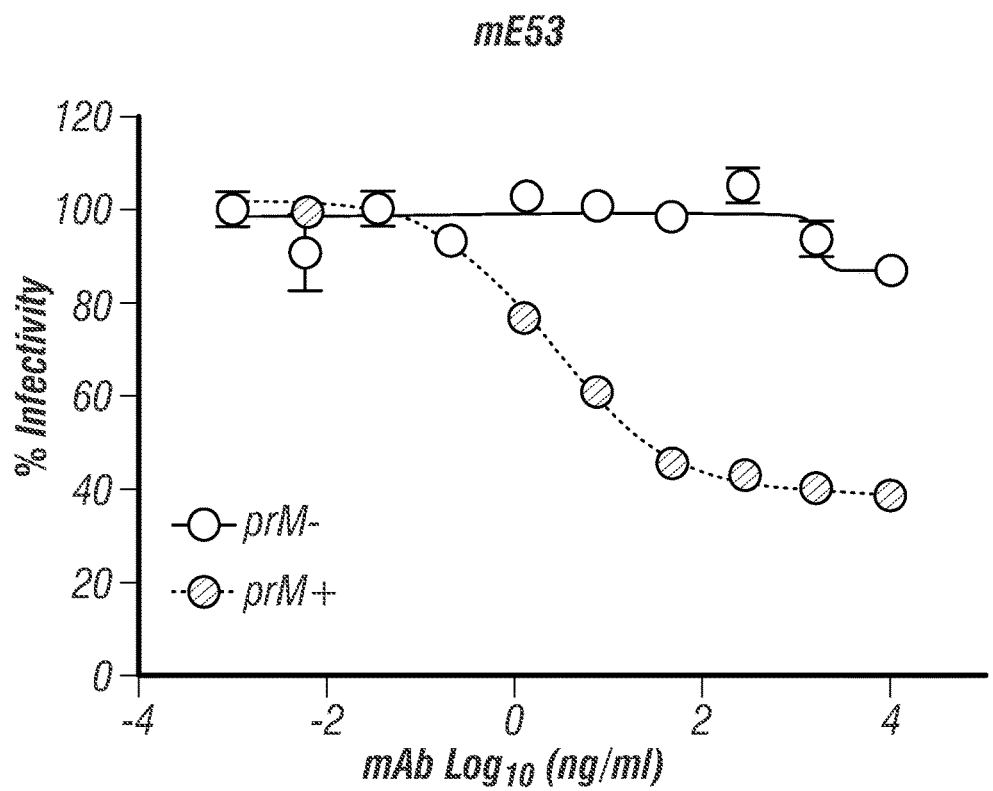
Figure 2C:
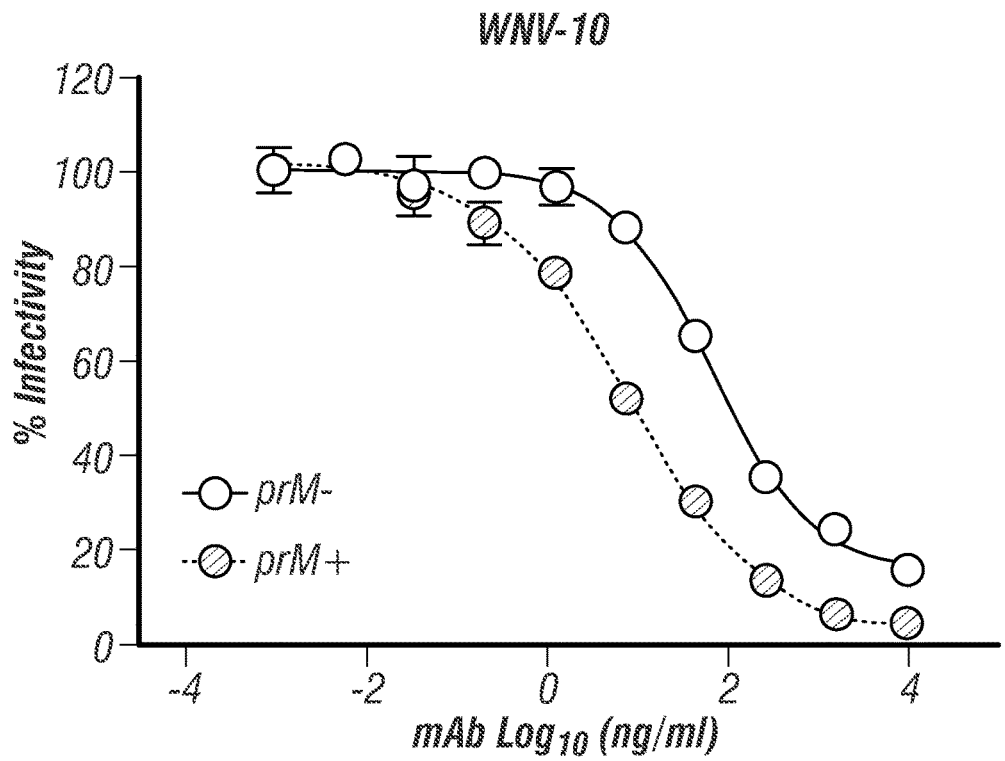
Figure 2D:
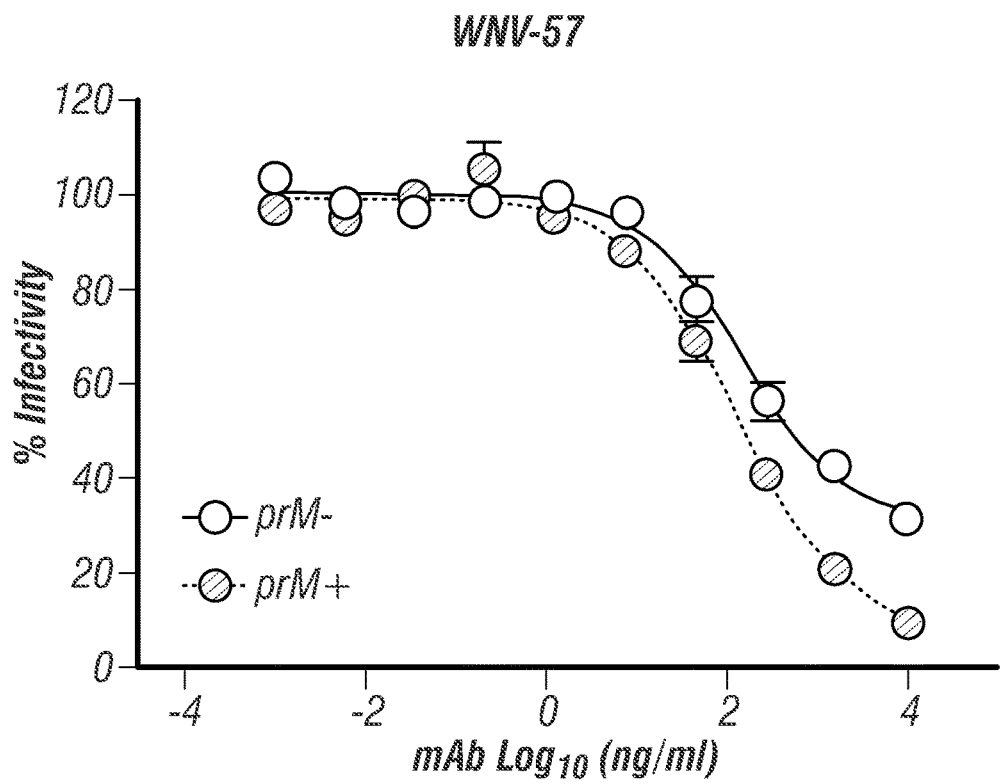
Figures 2E, 2F:
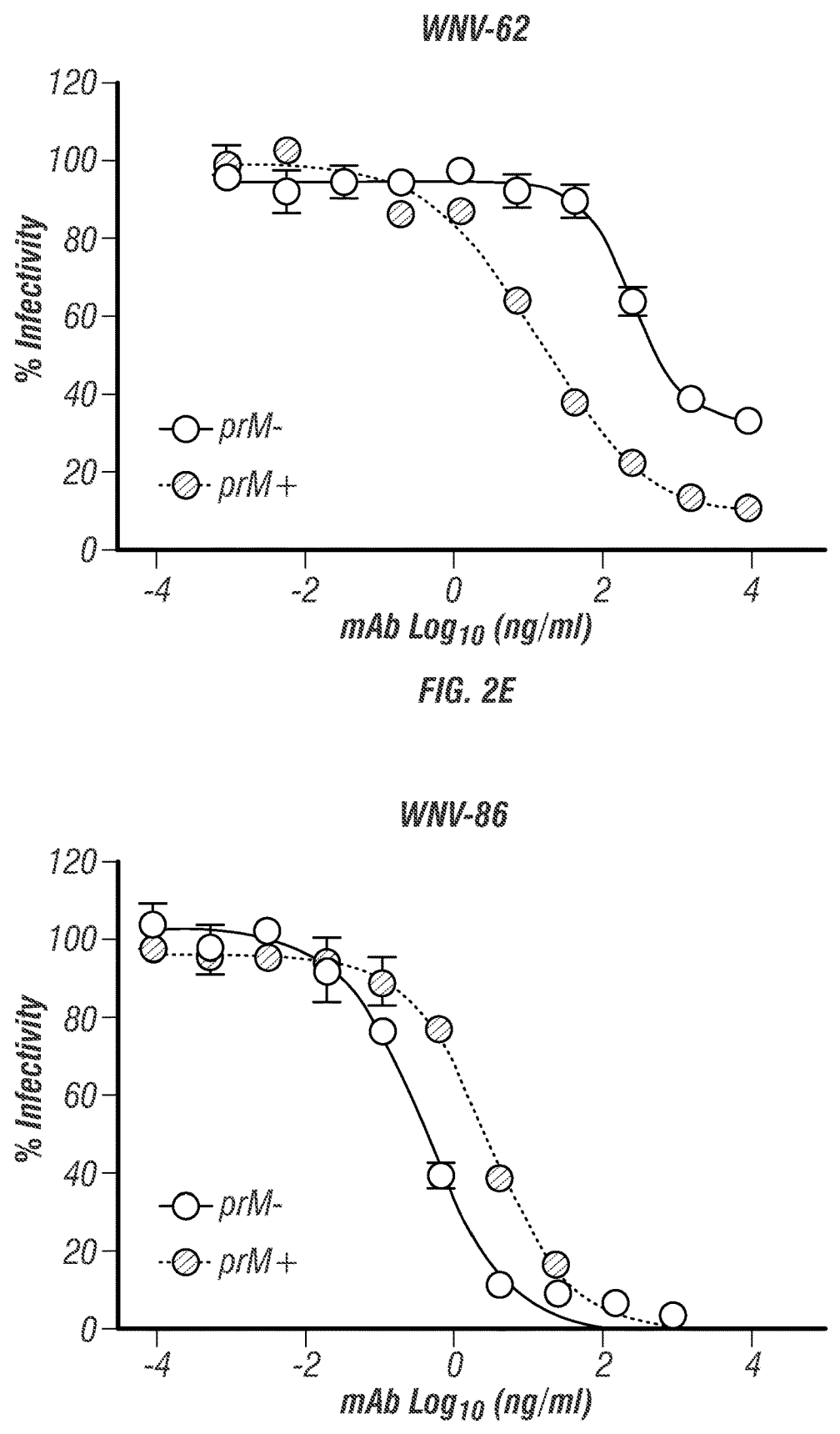
Figure 2G:
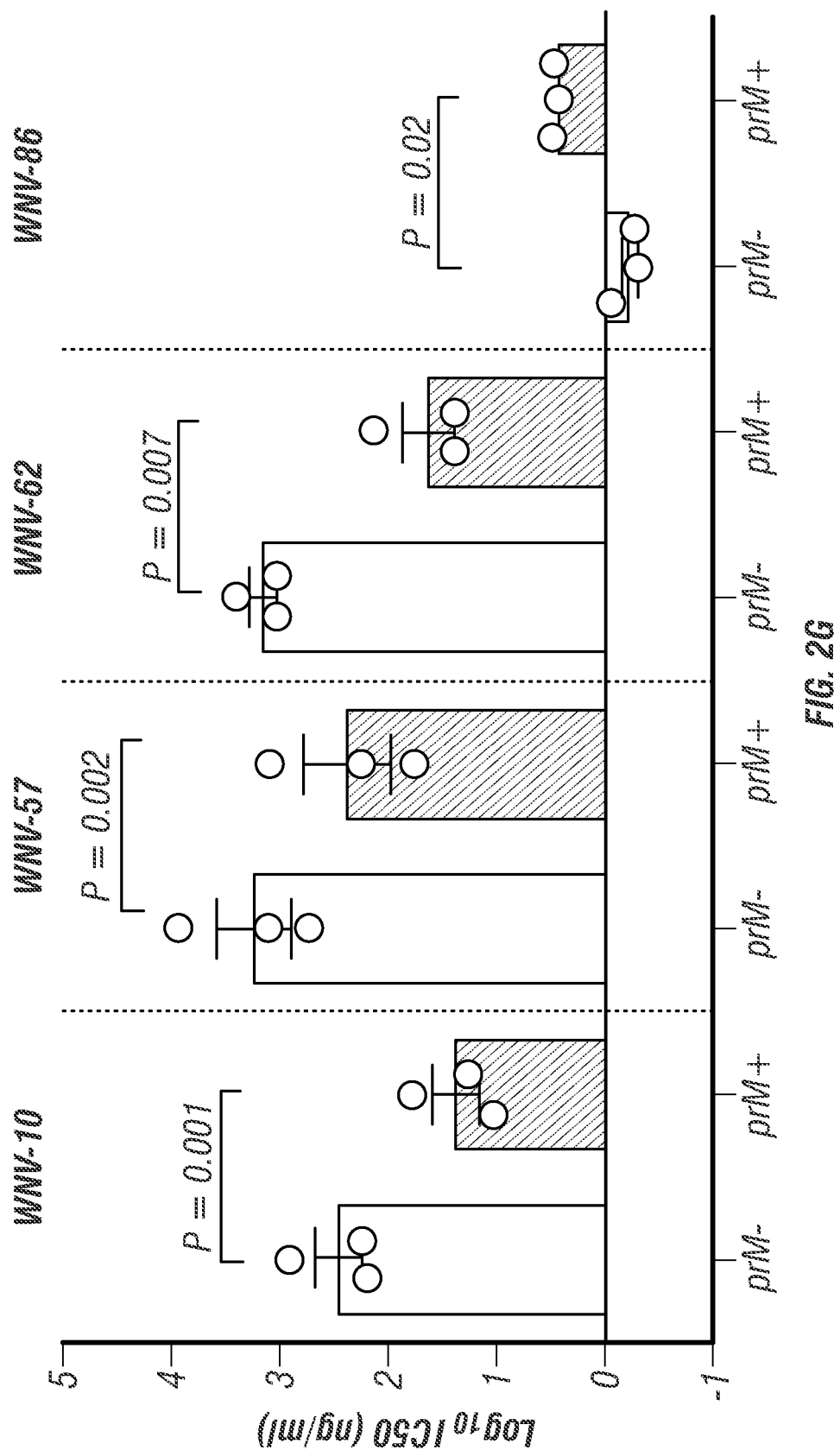

MAbs do not target immunodominant epitopes in DII-FL or DIII for murine mAbs. To investigate whether the WNV-specific NAbs targeted the common previously described immunodominant murine mAba epitopes, the ability of mAbs WNV-10, WNV-57, WNV-62, and WNV-86 to neutralize wild-type (WT) WNV or RVP variants containing a mutation in the WNV E protein residue 332 (T332K) or 106 (G106V) was compared. These variant residues abolish binding of most antibodies specific for DIII-LR (Oliphant et al., 2005; Sanchez et al., 2005; Beasley & Barrett, 2002) or DII-FL (Goncalvez et al., 2004; Smith et al., 2013; Crill et al., 2004; Oliphant et al., 2006), respectively. As expected, WNV RVPs containing the T332K, but not the G106V mutation, resisted neutralization by the DIII-LR-specific mouse mAb E16 (FIG. 8A). The DII-FL specific mouse mAb E53 is weakly neutralizing, resulting in a large proportion of RVPs that remain infectious even at high mAb concentrations, due to heterogeneity in the accessibility of its epitope on virions containing varying amounts of prM (Nelson et al., 2008; Oliphant et al., 2006; Cherrier et al., 2009). Consistent with previous studies, E53 neutralization was not detected against WNV RVPs containing the G106V mutation (FIG. 8B) (Oliphant et al., 2006). In contrast, all 4 human mAbs isolated in the current study neutralized WT, T332K, and G106V RVPs with similar potency (<2-fold difference in $IC_{50}$, FIGS. 8C-2F). Each 4 of these mAbs also failed to bind to a recombinant WNV E protein containing only DIII (FIG. 8B), suggesting that their epitopes lie outside this region, which is targeted by the strongly neutralizing therapeutic mouse mAb E16. Finally, unlike most previously described potently neutralizing human mAbs against flaviviruses (Dejnirattisai et al., 2015; Kaufmann et al., 2010; de Alwis et al., 2012), all 4 mAbs bound to recombinant WNV E protein (FIG. 8H). These results demonstrated that the potently neutralizing human mAbs target neither known epitopes in DII-FL and DIII nor those requiring a complex quaternary structure.

mAb WNV-86 preferentially neutralized mature virus particles. Compared to fully mature virions that contain little or no prM, partially mature virions that retain uncleaved prM are generally more sensitive to neutralization by antibodies, particularly those targeting poorly exposed epitopes (Nelson et al., 2008; Cherrier et al., 2009). The prM content of virus particles can be manipulated by preparing viruses in the presence of overexpressed human furin or $NH_4Cl$ to increase (prM−) or decrease (prM+) cleavage efficiency of prM, respectively (Nelson et al., 2008). To determine whether the neutralizing activities of the isolated human mAbs were affected by virion maturation state, the ability to neutralize prM− or prM+ WNV RVPs was compared. As previously shown, mouse mAb E16, which targets the highly accessible DIII-LR epitope, neutralized these particles with similar potency (FIG. 2A) (Nelson et al., 2008), while mouse mAb E53, which is specific for the cryptic DII-FL epitope, neutralized prM+ RVPs but not prM− RVPs (FIG. 2B) (Nelson et al., 2008; Cherrier et al., 2009). As seen with most antibodies described to date (Nelson et al., 2008; Guirakhoo et al., 1992; Heinz et al., 1994;), three out of the four human mAbs displayed increased neutralization potency against prM+ RVPs relative to prM− RVPs to varying extents (13-fold, 7-fold, or 27-fold decrease in $IC_{50}$ for mAbs WNV-10, WNV-57, or WNV-62, respectively, FIGS. 2C-2E and 2G). In contrast, the $IC_{50}$ of mAb WNV-86 was 4-fold lower (P=0.02) against prM− RVPs compared to prM+ RVPs (FIGS. 2F-2G), suggesting that this mAb recognizes an epitope preferentially displayed on mature virus particles lacking prM.

Figure 3A:
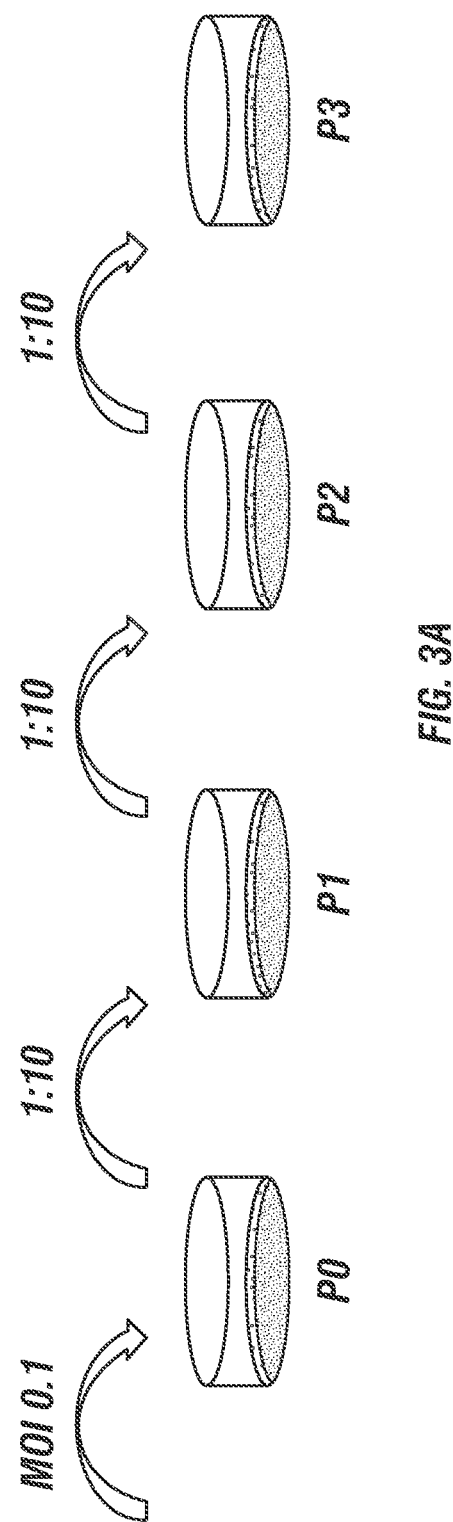
Figures 3B, 3C:
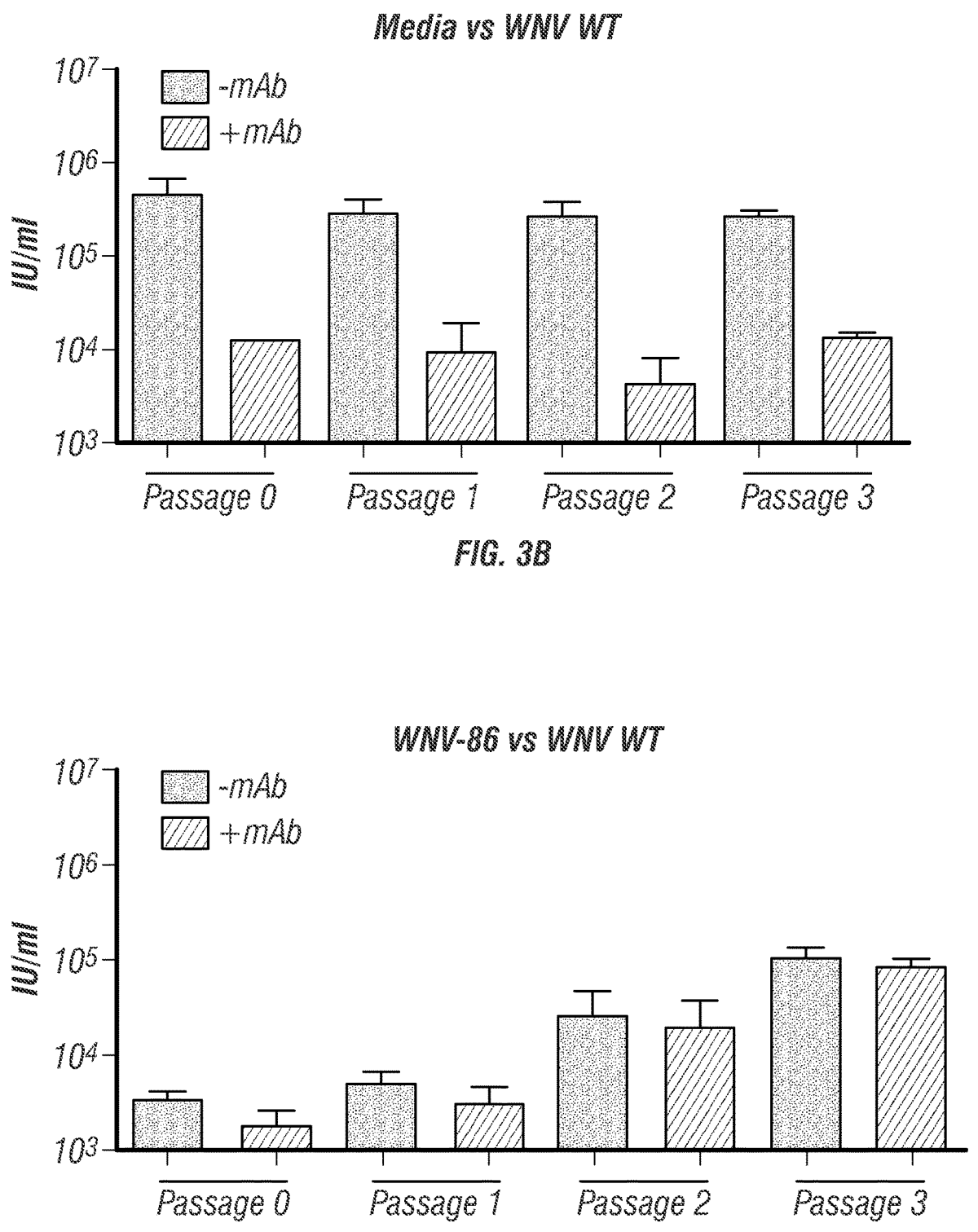

In vitro selection of mAb WNV-86 neutralization escape variant viruses. To gain insight into the epitope targeted by mAb WNV-86, the fully infectious GFP-expressing WNV (Lin et al., 2012) was serially passaged on Vero cell monolayer cultures in duplicate wells in two independent experiments (FIG. 3A) in the presence of WNV-86 at a concentration 200-fold greater than its $IC_{50}$ against WT WNV (FIGS. 1A-F). At each passage, replication of antibody escape variants was monitored by inoculating Raji-DC-SIGNR cells with an aliquot of virus supernatant titrated in the presence or absence of a neutralizing concentration of WNV-86. As anticipated, WNV passaged in the absence of WNV-86 selection pressure infected Raji-DCSIGNR cells in the absence of mAb but was strongly (20- to 60-fold) inhibited by the presence of mAb included in virus titration experiments (FIG. 3B). Although only low titers of WNV grown in the presence of WNV-86 at early passages were recovered, after three serial passages under mAb selection pressure, WNV displayed high titers (~$10^5$ IU/mL) when titrated in the presence or absence of WNV-86, indicating successful escape from neutralization (FIG. 3C). Neutralization studies performed with WNV-86 confirmed that virus supernatant obtained from the third serial passage under mAb selection was resistant to neutralization, whereas virus propagated in control medium wells remained highly sensitive to neutralization by WNV-86 (FIG. 3D).

Mutation at a single residue in E protein DII conferred WNV-86 escape. Next, the viral mutation(s) that conferred WNV-86 neutralization escape by comparing the bulk RNA sequences of escape variants to those of WNV passaged in parallel in the absence of antibody selection from each of the two independent experiments detailed above were determined. All (4/4) escape variants contained a single nucleotide change corresponding to an amino acid substitution at residue 64 (T64N) in DII of the E protein that resulted in the addition of a potential N-linked glycosylation site (PNGS). To confirm that this mutation conferred escape from WNV-86, a WNV T64N RVP variant was generated for further characterization. By performing SDS-PAGE and western blotting of pelleted WT or T64N RVPs, a slower migration rate of E proteins on T64N compared to WT RVPs was observed (FIG. 4A), suggesting that the additional PNGS introduced by this mutation were indeed occupied by glycans. In support of this, treatment with PNGase F resulted in a similar migration rate of WT and T64N E proteins (FIG. 4A). Interestingly, the T64N mutation conferred resistance to neutralization not only by WNV-86, but also by other human mAbs, including WNV-10, WNV-57, WNV-62, and mouse mAbs E53, E60, and E121 (Oliphant et al., 2006), which target epitopes within the DII-FL (E53, E60) and DI (E121) (FIGS. 9A-9G). Among all mAbs tested, only mouse mAb E16, which targets the highly accessible DIII-LR epitope (Nybakken et al., 2005), was not affected by the T64N mutation (FIG. 9H).

Figure 4B:
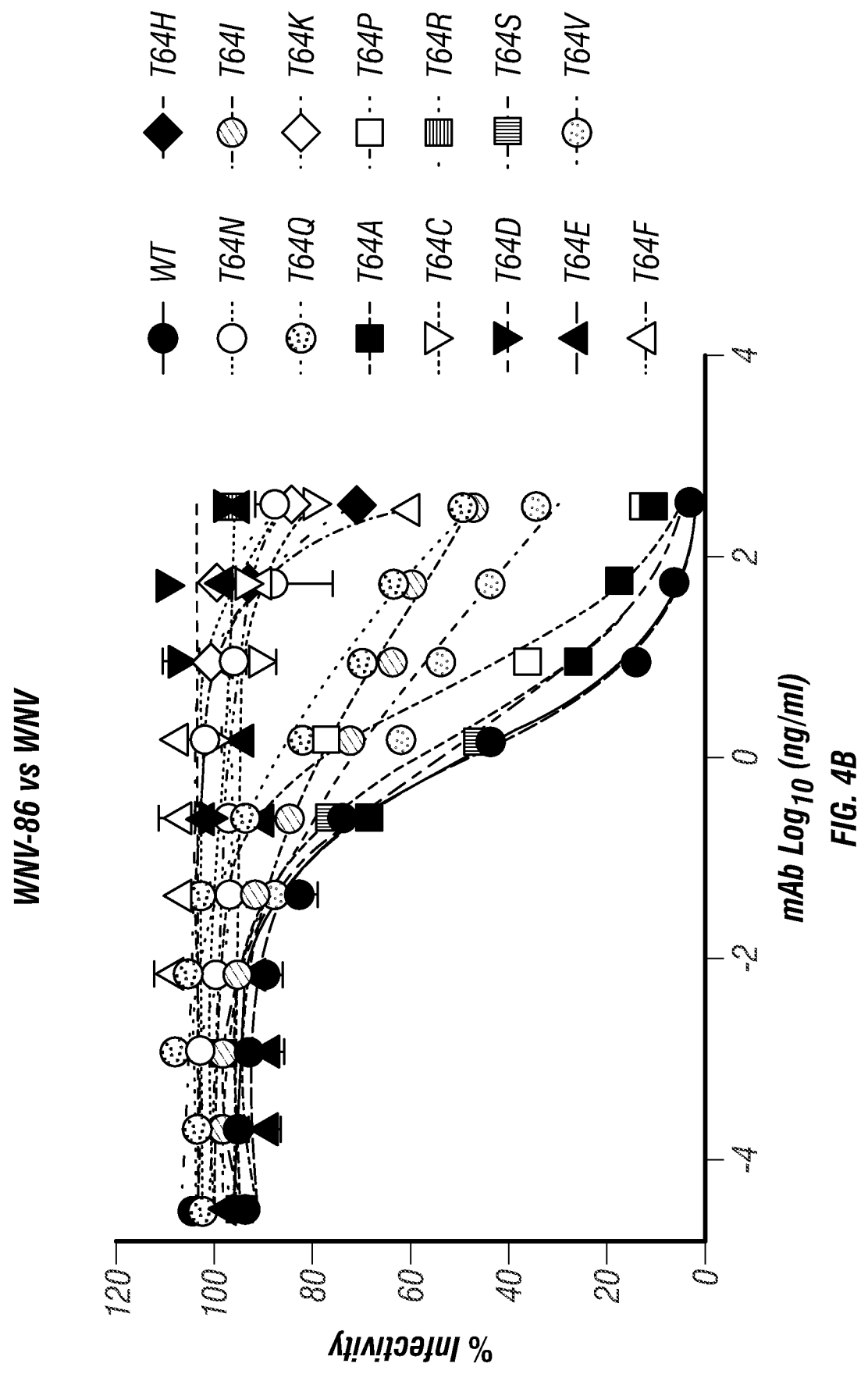
Figure 4C:
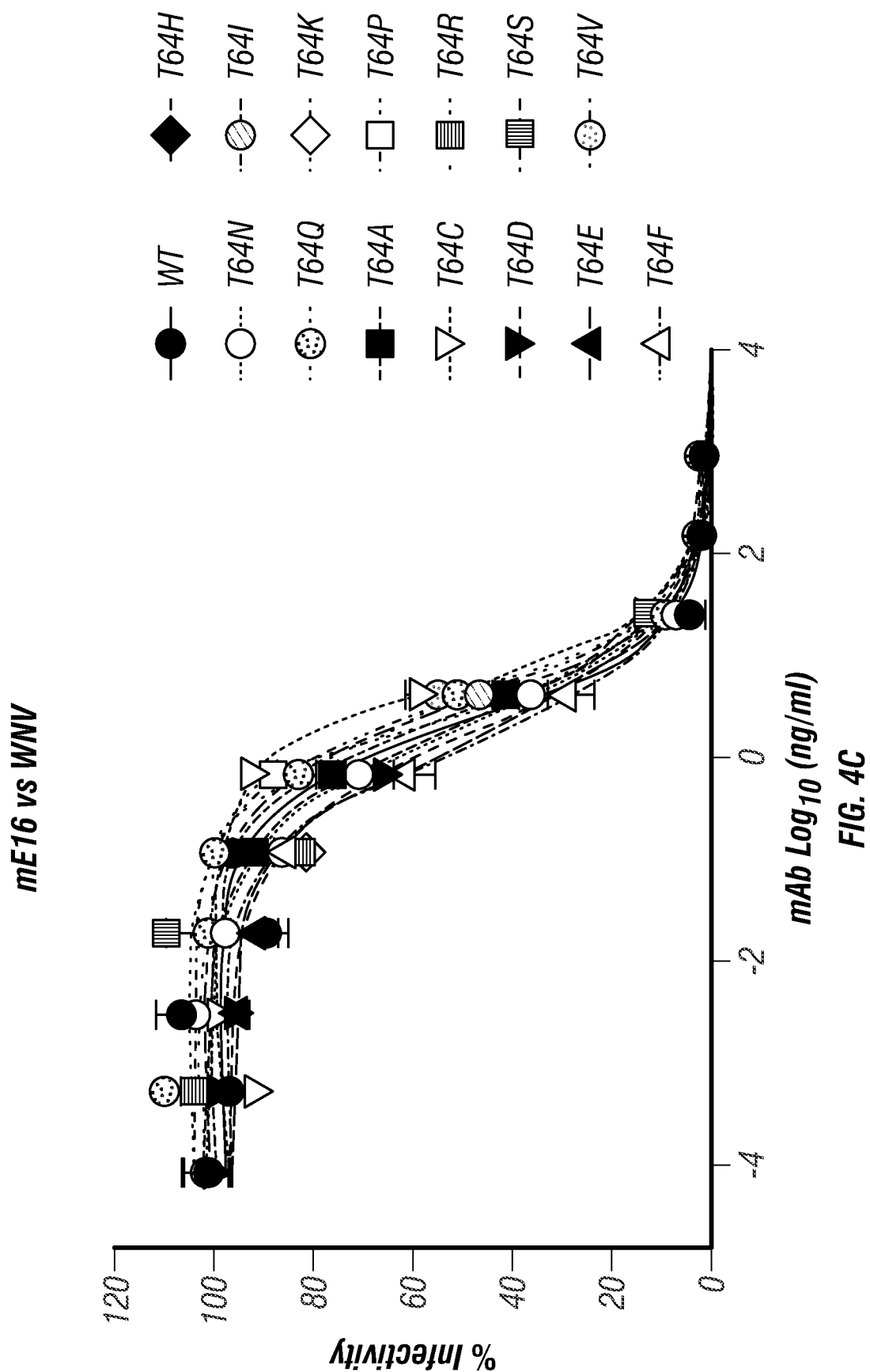
Figure 4E:
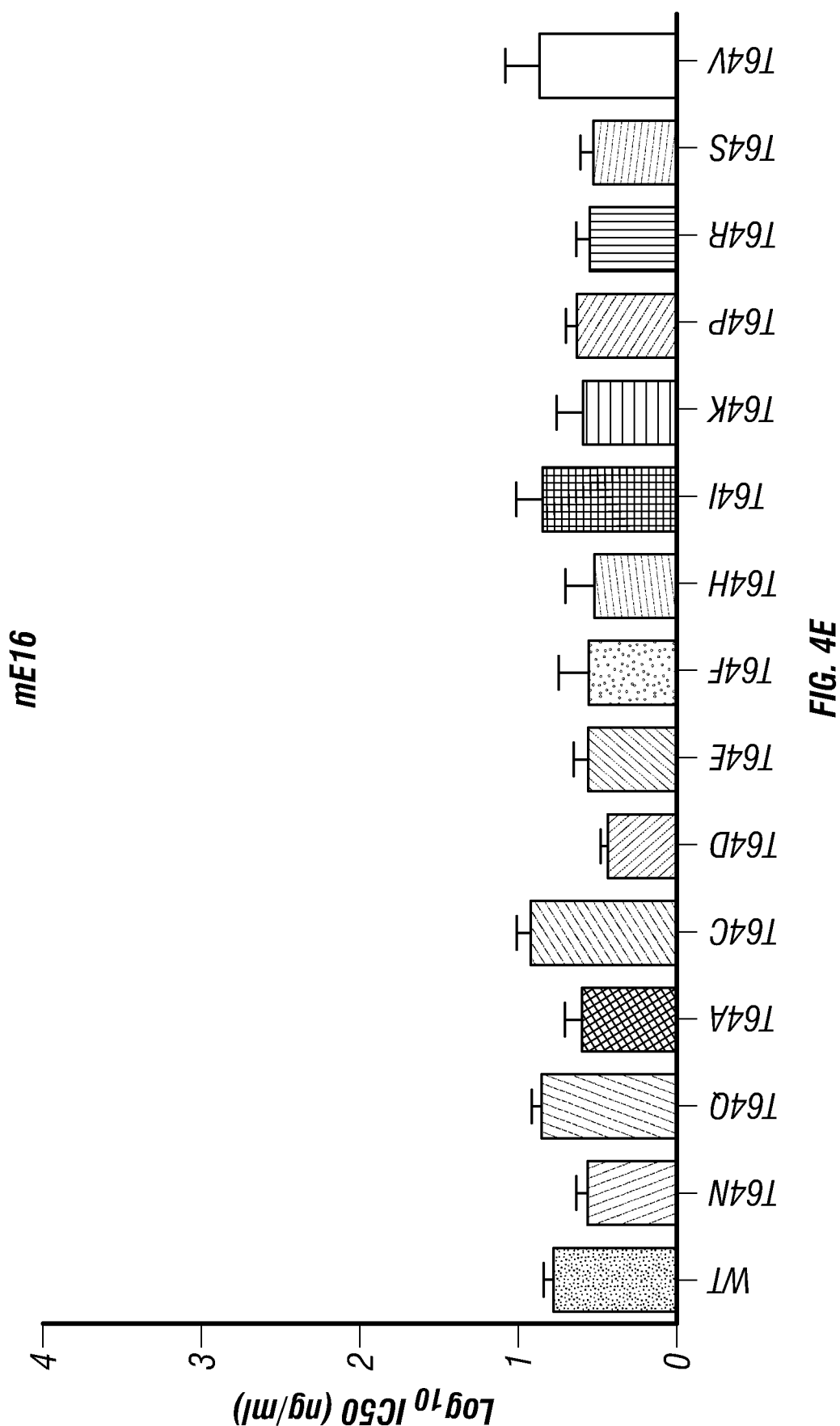

The ability of the T64N mutation to confer broad resistance to neutralization by mAbs was tested to determine if this feature was due to the addition of a glycan in the E protein. To test this, the threonine at E DII residue 64 was replaced with a glutamine (T64Q), which is chemically similar to an asparagine, but does not result in the addition of a PNGS motif. In neutralization studies, the T64Q mutation did not affect the potency of any mAb with the exception of WNV-86 (FIGS. 9A-H); the sensitivity of T64Q RVPs to neutralization by WNV-86 was intermediate between that of WT and T64N RVPs (FIG. 9A). To further explore the importance of E DII residue 64 on WNV-86 recognition, twelve additional amino acid variants at this residue were created to represent distinct chemical groups. Overall, 11 out of the total 14 variants (excluding T64A, T64S, T64P) resulted in a 20-fold or greater reduction in WNV-86 potency (FIGS. 4B and 4D). In contrast, none of the T64 variants significantly impacted sensitivity to neutralization by E16 (FIGS. 4C and 4E). These findings demonstrate that, unlike most mAbs tested, the mutation at residue 64 plays an important role for WNV-86 in recognition of E protein, regardless of glycan occupancy.

Figures 5A, 5B:
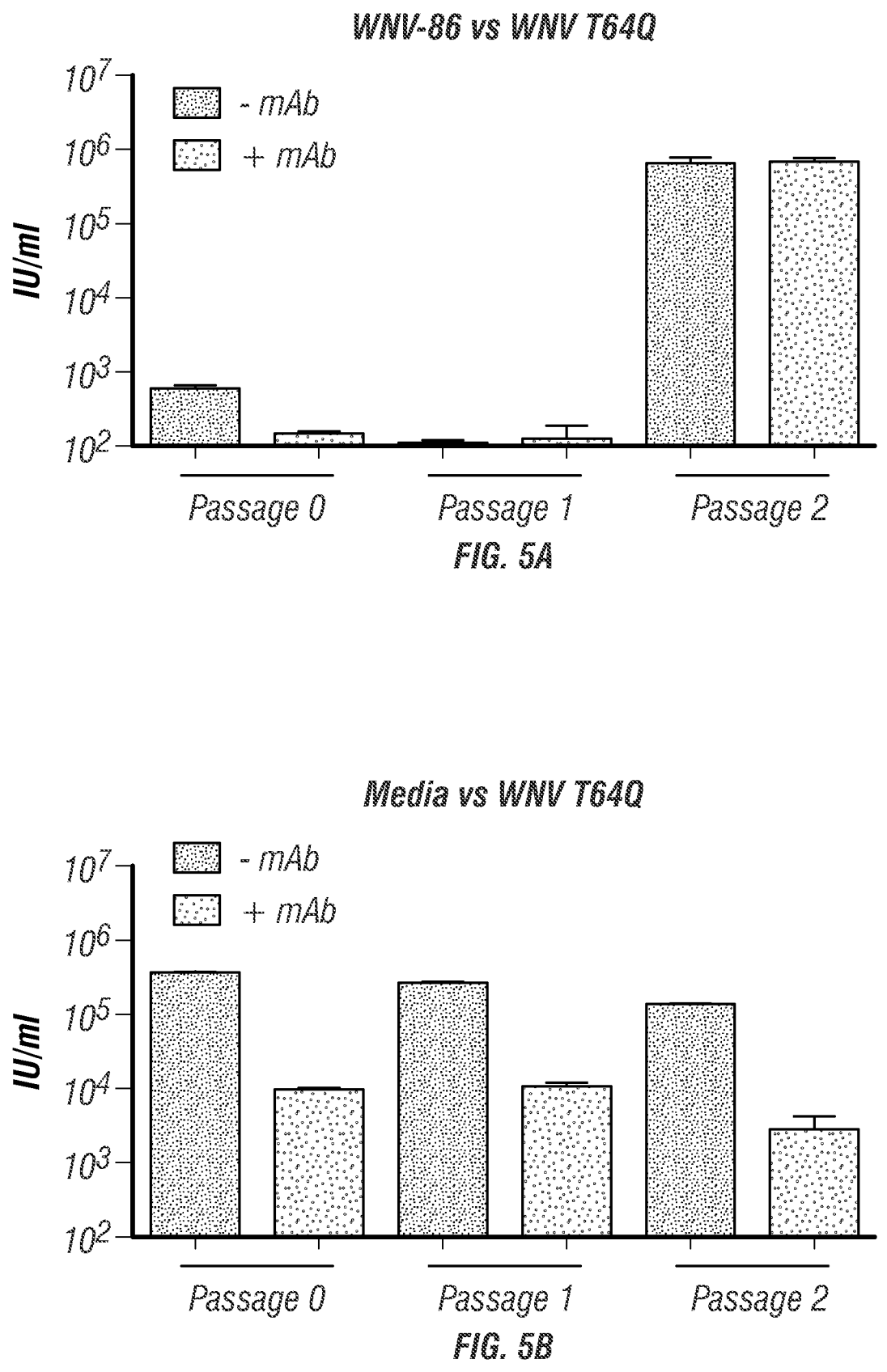

Epitope mapping of WNV-86. To identify additional E residues that contribute to WNV-86 recognition, a second set of in vitro neutralization escape experiments was performed (as described in FIGS. 3A-D) by serially passaging a WNV T64Q infectious clone variant, which displayed an intermediate sensitivity to neutralization by WNV-86 (FIG. 3A and FIGS. 4B and 4D), under mAb selection pressure. After two serial passages, virus-containing supernatant displayed robust infection of Raji-DCSIGNR cells even in the presence of mAb WNV-86, suggesting successful selection of neutralization escape variants (FIG. 5A), as confirmed by neutralization studies with mAb WNV-86. Virus-containing supernatant obtained from duplicate wells following two serial passages under mAb selection pressure resisted neutralization, whereas viruses passaged in control wells containing media only did not escape neutralization (FIG. 5C).

Figure 5E:
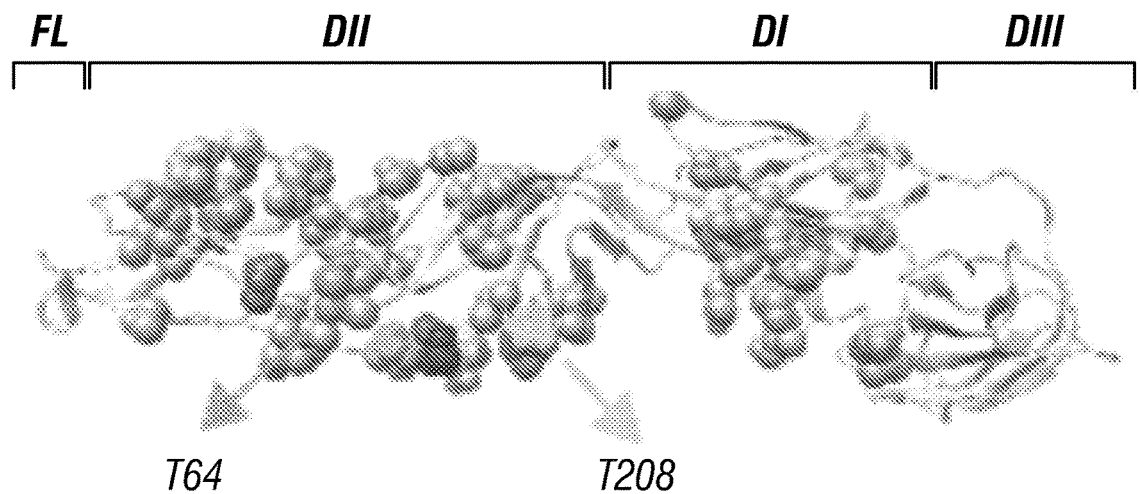

Comparison of bulk viral RNA sequences isolated from WNV T64Q passaged in the presence or absence of mAb WNV-86 in duplicate wells identified a single nucleotide change in 2/2 escape variants that resulted in a second amino acid substitution at E DII residue 208 (T208K, FIG. 5E). As observed with WNV T64Q RVPs, when tested individually, WNV RVPs containing a T208K mutation reduced, but did not eliminate sensitivity to neutralization by WNV-86 (88- or 13-fold increase in $IC_{50}$, respectively, FIGS. 5D and 5F). However, in combination, these two mutations abrogated WNV-86 neutralization (FIG. 5D), suggesting that mutation at both residues is required for neutralization escape from WNV-86.

Figure 5F:
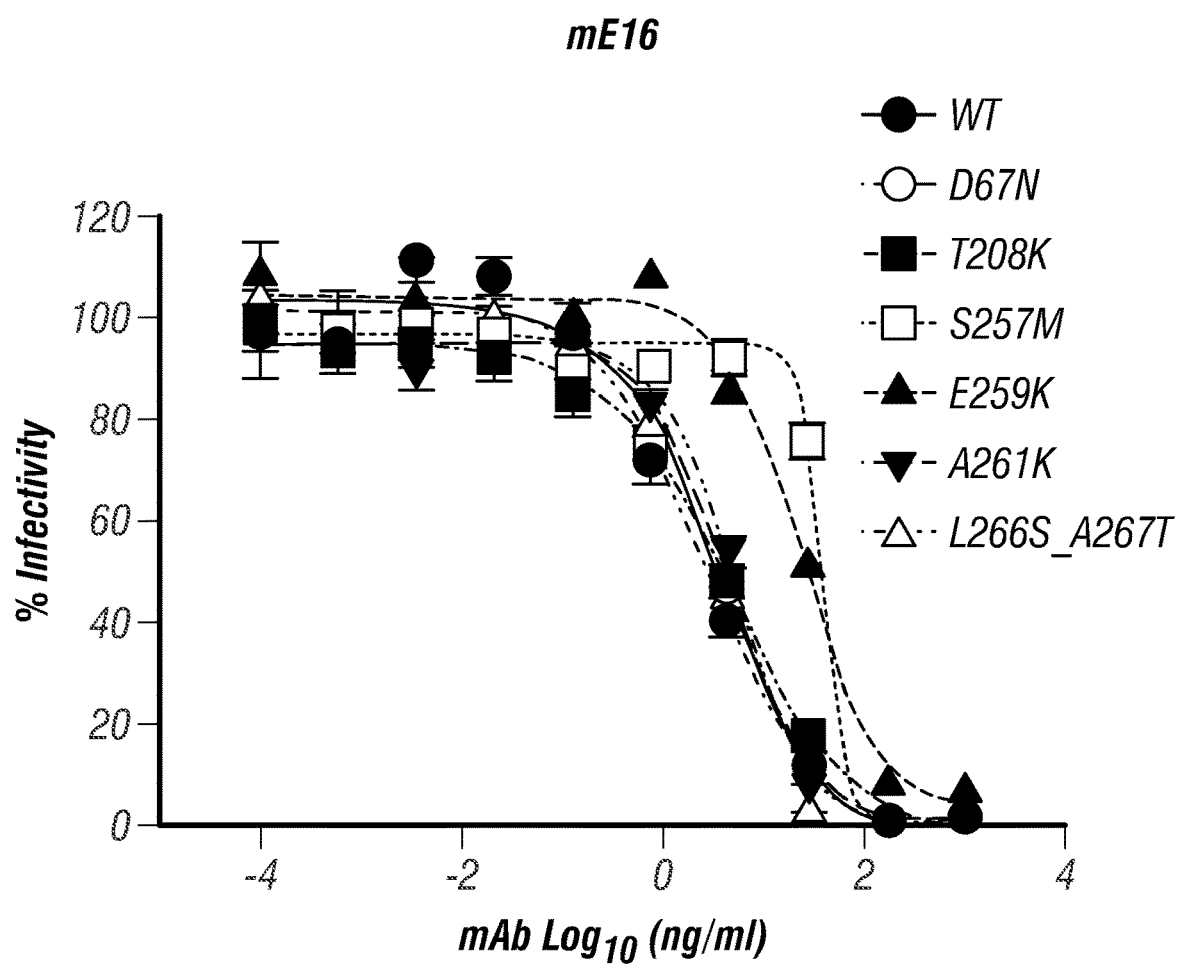
Figure 5G:
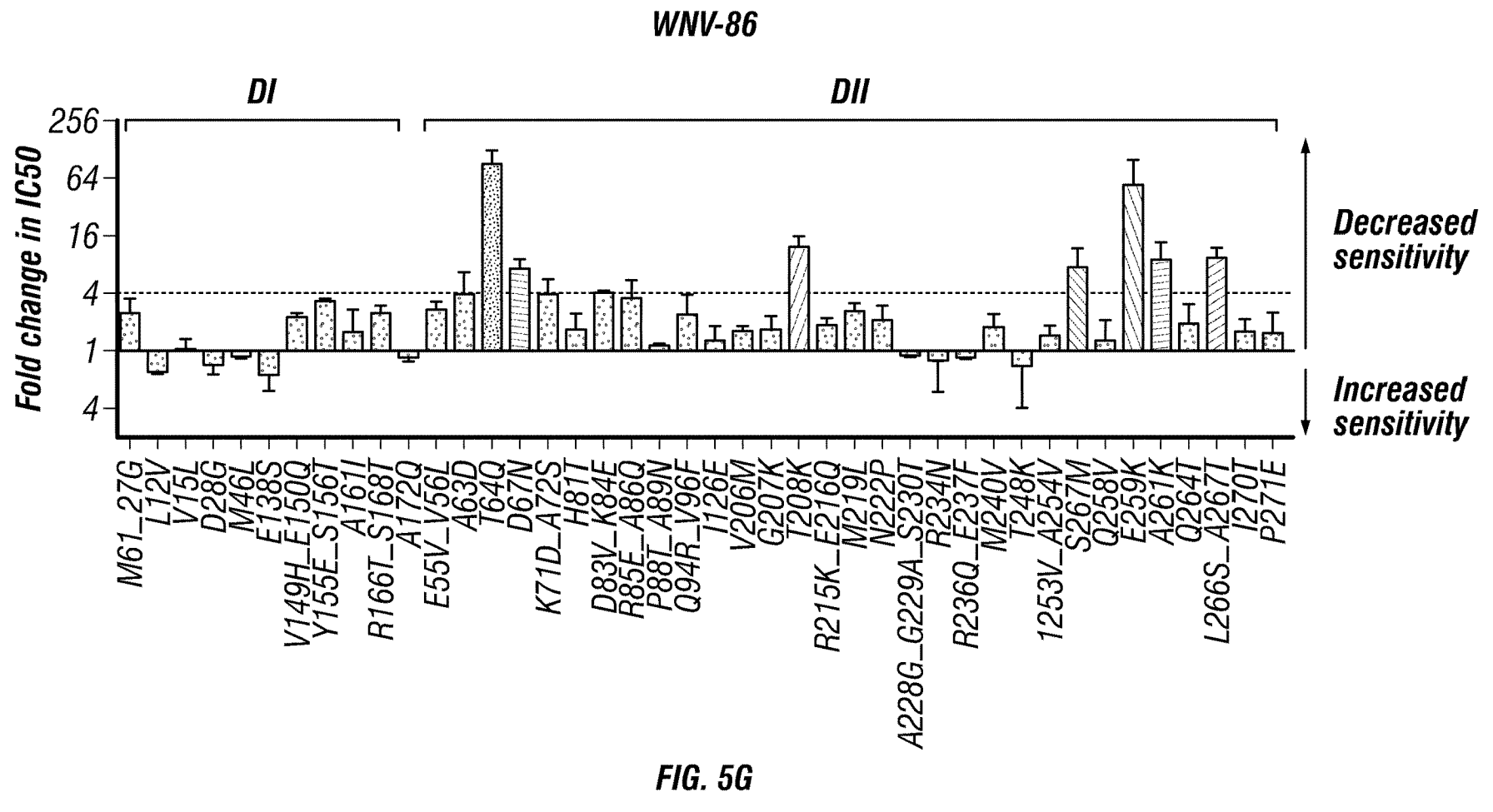

To further define the epitope targeted by WNV-86, a panel of 42 RVP variants encoding single, double, or triple mutations at a total of 58 solvent accessible residues throughout DI and DII of the E protein was screened, including E DII residues 64 and 208 identified in the in vitro selection experiments above. Of 58 total mutations tested, 27 displayed minimal effects on sensitivity to neutralization (<2-fold change in $IC_{50}$), 23 modestly decreased sensitivity to neutralization (2- to 4-fold increase in $IC_{50}$), and 8 reduced sensitivity by >4-fold (FIG. 5G). All 8 mutations that reduced WNV-86 potency by >4-fold are clustered in DII and, with the exception of D67N, are bounded by residues T64 and T208 (FIGS. 5E and 5G), suggesting that the binding footprint of mAb WNV-86 lies within this region. To exclude the possibility that these 8 mutations non-specifically altered antigenicity, they were tested against mouse mAb E16, which targets a well-defined, distal epitope in DIII-LR. Two of these mutations (S257M and E259K) also reduced sensitivity to neutralization by mouse mAb E16 by >10-fold (FIG. 5F). Although the D67N mutation did not alter sensitivity to neutralization by E16, this mutation conferred broad resistance to a panel of mAbs targeting distinct epitopes (FIG. 6). These results suggest that these 3 mutations indirectly affect WNV-86 recognition through overall changes in E protein antigenicity.

Figure 10A:
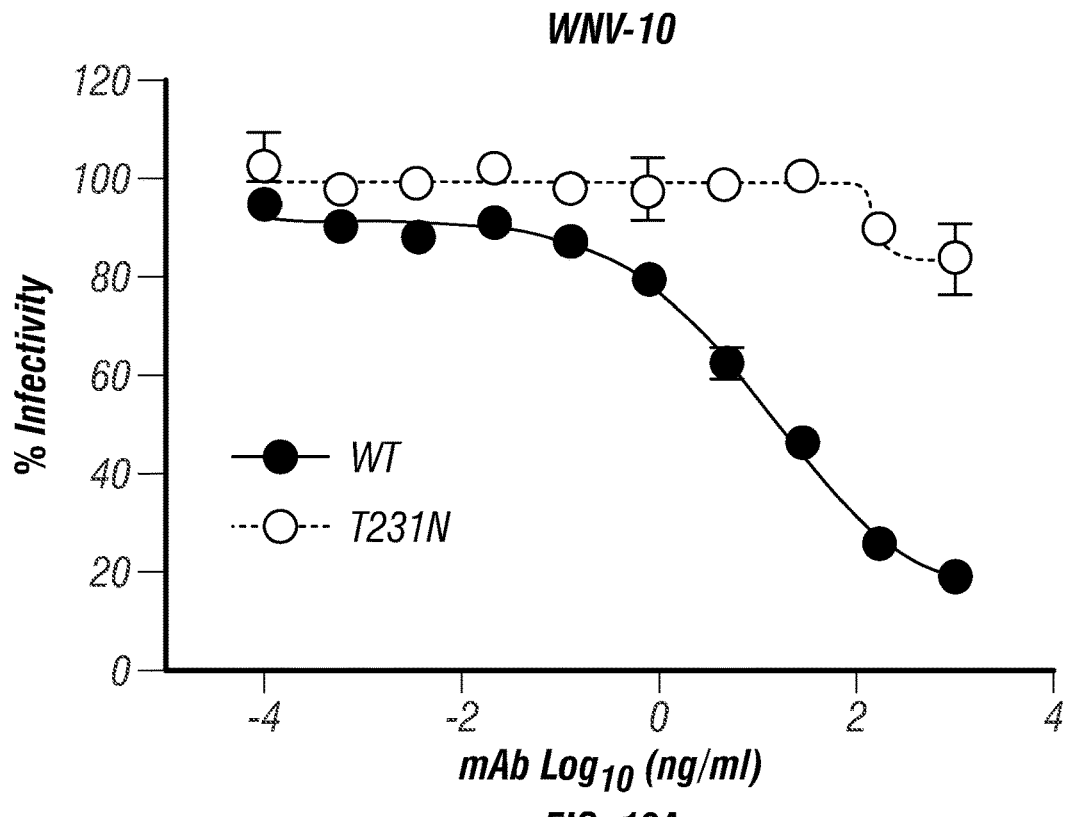
FIGS. 10A-C. Mutation at E DII residue T231 confers escape from WNV-10. Neutralization of WNV WT or T231N RVPs by mAb (FIG. 10A) WNV-10 or (FIG. 10B) WNV-86. Error bars indicate the range of duplicate infections. Neutralization curves shown are representative of three independent experiments.
Figure 10B:
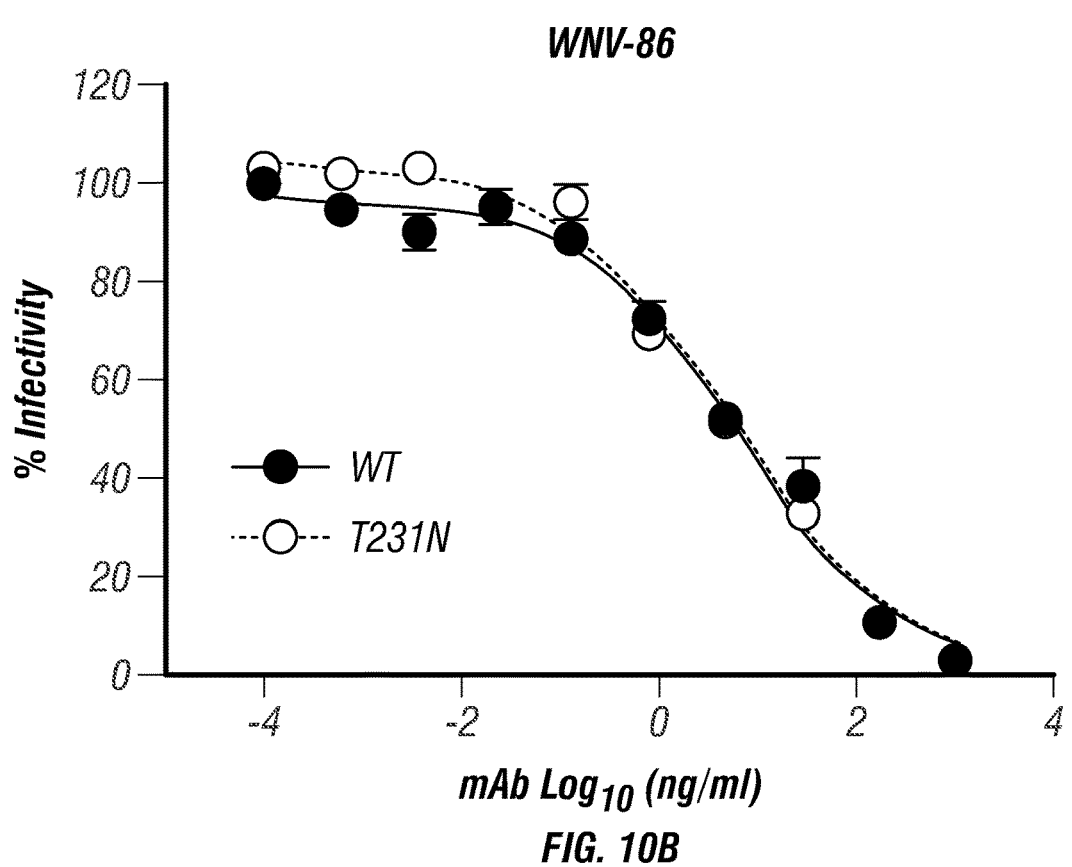
Figure 10C:
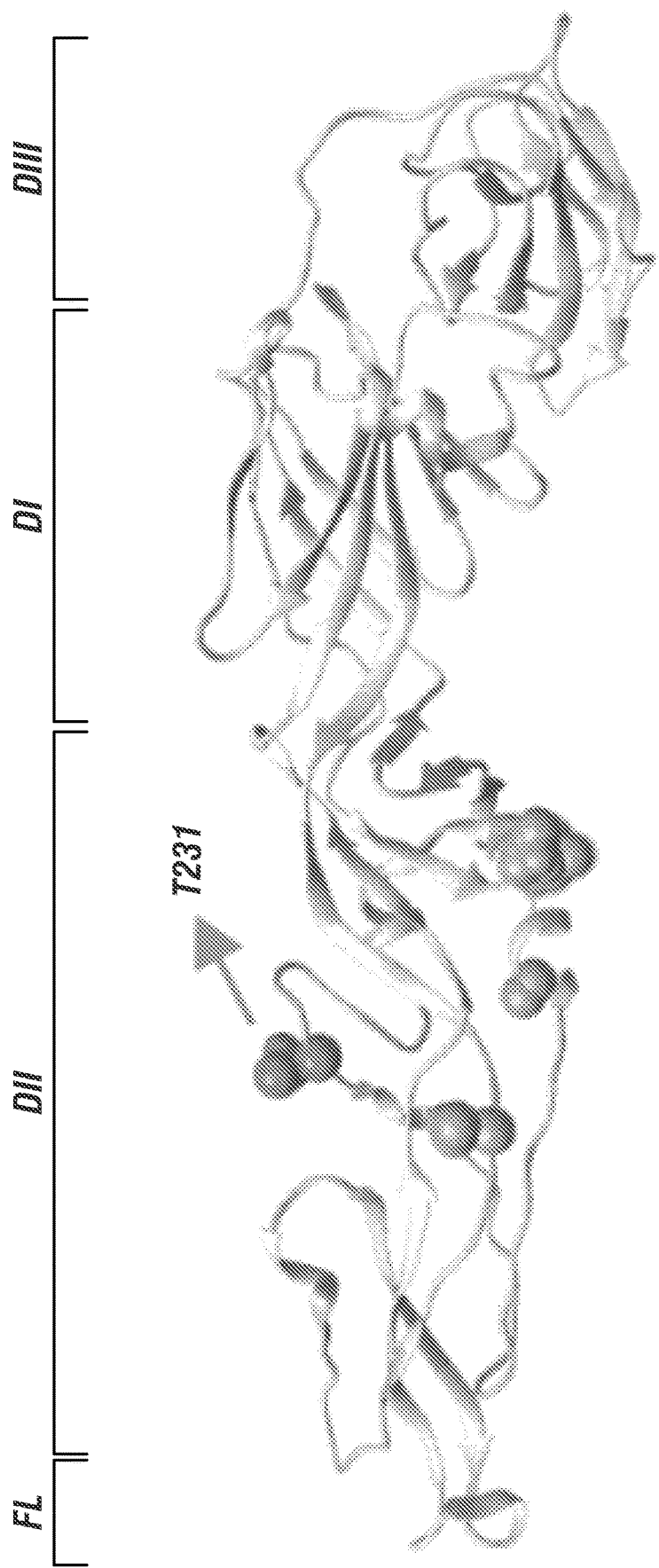
Figure 12E:
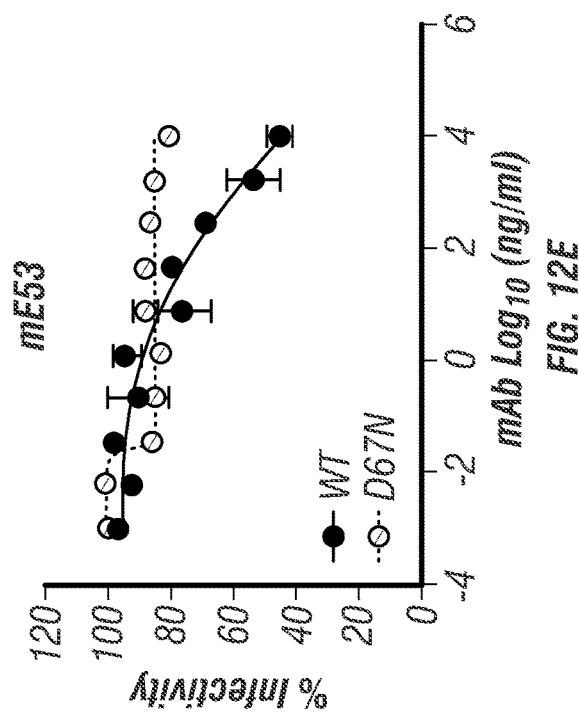
Figure 12F:
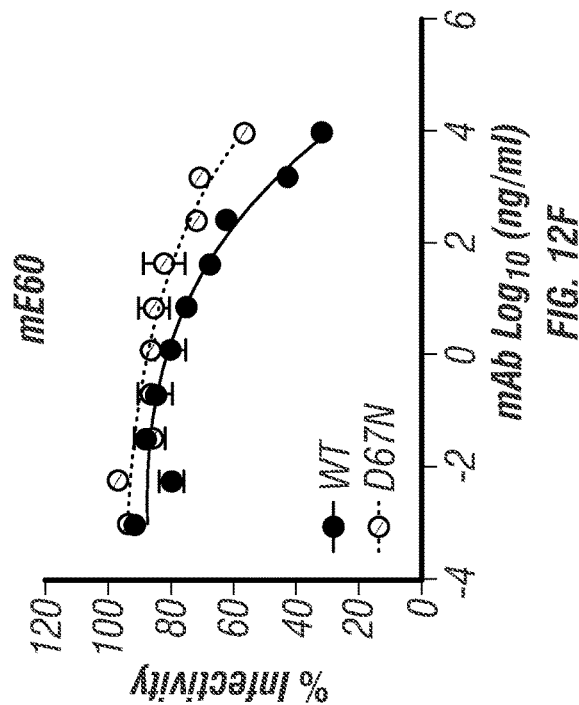
Figure 12G:
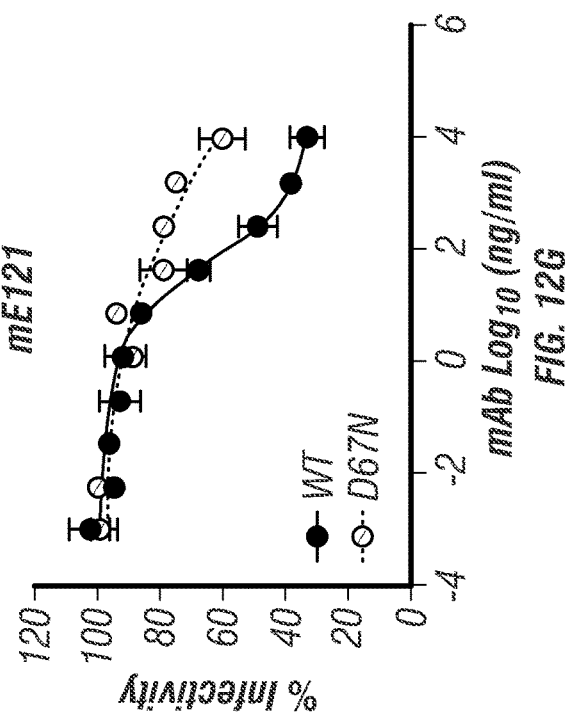
Figure 12H:
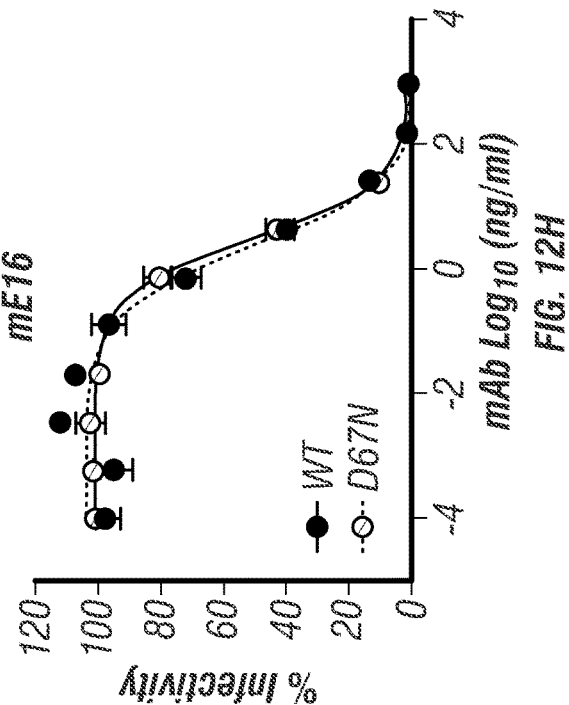

Therapeutic efficacy of mAbs. To evaluate the therapeutic potential of neutralizing human mAbs, five-week old C57BL/6J mice were infected with WNV, treated with a single dose (100 µg) of mAb WNV-86 or WNV-10 two days following infection, and monitored for survival for 30 days. These mAbs were isolated from two different WNV-infected individuals and chosen because they represent the two most potently neutralizing mAbs in the screen (FIGS. 1A-F). Additionally, selection and characterization of WNV-10 escape variants in vitro identified a single mutation at E residue 231 (T231N) that conferred resistance to neutralization by WNV-10 (FIG. 10A) but not WNV-86 (FIG. 10B). Although also located in E DII, this residue is located outside the predicted binding footprint of WNV-86 (FIGS. 5A-F and FIG. 10C). These findings suggest that WNV-86 and WNV-10 target non-overlapping epitopes.

As seen with mice treated with humanized mouse mAb E16 (hE16), which was shown previously to be therapeutic in vivo (Oliphant et al., 2005), mice treated with mAb WNV-86 were protected completely from mortality (FIG. 6). In contrast, treatment with mAb WNV-10 afforded only partial protection, with 5 out of 10 mice succumbing to infection by day 19. Treatment with an isotype-control humanized mAb (hCHK152) resulted in significant mortality (9 out of 10 mice) by day 16. Thus, the potent neutralizing activity of mAb WNV-86 in vitro correlated with therapeutic efficacy in vivo. Although the in vitro neutralization potency of mAb WNV-10 was similar to that of mAb E16 (~10 ng/mL, FIGS. 1E-F) (Pierson et al., 2007), only the latter afforded complete protection from lethal infection, suggesting that additional properties in addition to in vitro neutralization potency determine mAb therapeutic efficacy (Oliphant et al., 2005).

Example 3—Discussion

In this study, the inventor sought to identify a panel of potently neutralizing human mAbs against WNV with therapeutic potential. By isolating and culturing B cells from three WNV-infected individuals with potent serum neutralizing activity, the inventor successfully obtained a total of 10 mAbs with varying neutralization potencies against WNV. MAb WNV-86 was the most potent, neutralizing WNV with an $IC_{50}$ that was approximately 3-fold lower than that for mAb E16, which has been shown previously to prevent mortality in WNV-infected mice, even when a single dose of its mouse or humanized form was administered as late as 5 days post-infection (Oliphant et al., 2004). Like most potently WNV neutralizing mouse antibodies, E16 targets a highly exposed epitope within the E protein DIII-LR Nybakken et al., 2005). In contrast, WNV-86 did not recognize epitopes within DIII, consistent the recognition pattern of recent studies of potently neutralizing human mAbs for flaviviruses (VanBlargan et al., 2016). Unlike most potently neutralizing human mAbs identified recently (Dejnirattisai et al., 2015; Kaufmann et al., 2010; de Alwis et al., 2012), however, WNV-86 bound to recombinant soluble E protein, suggesting its epitope does not require a complex quaternary arrangement. In vitro selection of neutralization escape variant viruses and epitope mapping studies revealed a cluster of residues in DII that likely comprise the WNV-86 epitope. Although the exact binding footprint of WNV-86 awaits structural studies, the DII epitope identified by the mapping studies appears distinct from those targeted by many strongly neutralizing human mAbs, which often target the hinge region between DI and DII (Kaufmann et al., 2010; de Alwis et al., 2012; Teoh et al., 2012).

In addition to its novel epitope and potent neutralizing activity, another unique property of mAb WNV-86 is its ability to neutralize mature virions lacking uncleaved prM better than those that retain prM due to incomplete maturation. This finding is in contrast to the many monoclonal and polyclonal antibodies characterized to date (Guirakhoo et al., 1992; Heinz et al., 1994; Nelxon et al., 2008). The increased sensitivity of prM-containing virions to neutralization by many antibodies may be explained by improved epitope accessibility on E proteins arranged as a heterotrimeric spikes in association with prM relative to that on E proteins assembled as homodimers in a dense herringbone arrangement on mature particles lacking prM (Pierson & Diamond, 2012). An exception to this model may apply to antibodies targeting quaternary epitopes that span within and across E protein dimers (Dejnirattisai et al., 2015; Kaufmann et al., 2010; Teoh et al., 2012; Fibriansah et al., 2015a; 2015b; Barba-Spaeth et al., 2016; Zhang et al., 2016); these antibodies should in theory preferentially neutralize mature virions relative to those that retain prM (Dejnirattisai et al., 2015). Although the epitope of WNV-86 does not require a quaternary structure, detailed structural studies are required to determine whether the accessibility of this epitope is improved on E proteins assembled as dimers on the mature virus particle. Alternatively, while not required for binding, residues on the opposing E protein within the dimer may contribute to WNV-86 interactions, thus improving mAb recognition and neutralization potency.

Although WNV-86 escape variant viruses were readily selected in vitro, the potential for in vivo selection of WNV-86 escape variants remains to be determined. Notably, despite the presence of naturally occurring variation at residues important for recognition by the mAb E16 (Li et al., 2005), in vivo selection of E16 escape variant viruses occurred only infrequently, even in immunodeficient mice (Zhang et al., 2009). The in vitro selection experiments identified E DII residues important for WNV-86 recognition. In two independent experiments, all neutralization escape variant viruses isolated encoded the same T64N mutation, which is predicted to add a glycosylation site in the WNV E protein. Many virus envelope glycoproteins employ a 'glycan shield' mechanism to evade Nabs (VanBlargan et al., 2016). Indeed, the T64N mutation conferred broad resistance to neutralization by mAbs targeting distinct epitopes. Interestingly, this mutation is proximal to E DII residue 67, which is glycosylated in DENV (N67), but not WNV (D67), and introduction of a glycosylation site at this residue (D67N) into WNV RVPs similarly resulted in broad resistance to neutralization by mAbs (FIGS. 12A-H). Despite these observations, escape from WNV-86 was not limited to the addition of a glycan at residue T64. Instead introduction of multiple amino acid variants with distinct chemical groups significantly reduced or eliminated WNV-86 recognition, suggesting that this residue is directly contacted by WNV-86. Additionally, WNV RVPs containing the D67N mutation only had a modest effect (<4-fold reduction in $IC_{50}$) on WNV-86 neutralization potency (FIG. 5F). Thus, in contrast to most mAbs tested here, WNV-86 recognition is affected minimally by the presence of glycans in this region of DII.

As seen with mAb E16, the in vitro neutralization potency of WNV-86 correlated with in vivo therapeutic efficacy. In contrast, despite potent neutralizing activity in vitro, when administered as a single dose post-exposure, mAb WNV-10 prevented WNV-induced mortality in only 50% of mice. Unlike WNV-86, which neutralized >98% of viruses at the highest mAb concentration tested (10 μg/mL), neutralization studies with WNV-10 consistently revealed a higher proportion (10-15%) of viruses resistant to neutralization at similar concentrations (FIGS. 1C-D and FIG. 11A-D). Thus, it is possible that the inability of WNV-10 to completely neutralize WNV explains its incomplete protection against lethal infection. In addition to in vitro neutralization titers, other factors contribute to in vivo protection. For example, the protective efficacy of E16 was diminished in mice lacking Fc-γ receptors (Oliphant et al., 2005), demonstrating that antibody effector functions play a role in in vivo protection. Due to the prevalence of flavivirus attachment factors, antibodies that neutralize by blocking attachment may prevent infection of some cell types, but not others (Nybakken et al., 2005; Oliphant et al., 2006). Whether the mechanism of neutralization of WNV-86 or its ability to mediate Fc-mediated effector functions contributes to its therapeutic efficacy awaits further studies.

TABLE 1

NUCLEOTIDE SEQUENCES FOR ANTIBODY VARIABLE REGIONS

| Clone | Variable Sequence Region | SEQ ID NO: |
|---|---|---|
| WNV-6 heavy | caggtgcagctggtgcagtctggggctgaggtgaagaagcctggggcctcagtgaacatttcctgcaaggcatc tggatacaccttcaccaactactttatccactgggtgcgacaggcccctggacaagggcttgagtggatggggat gatcaaccctcgtggtggcagcacacacttcgcacagaagttccaggccagagtcaccatgaccagggacacat ccacgaatacagtttatatggaactgagcagcctgagatctgaggacacggccatgtattactgtgctaaagga atctgtaaaatctcatttatgtgtcccttcgaccctgggccagggaaccctggtcaccgtctcctca | 1 |
| WNV-6 light | gacatcgtgatgacccagtctccagcctccctgtctgcatctgtaagagacagagtcaccatcacttgccggca agtcagagcattaacaaccatgtaaattggtatcagcagaagccggggaaggcccctaaactcctgatctacag tacatccagtttgcaaagtggggtcccatccaggttcagtggcagtggatctgggacagatttcactctcaccatc agcagtctgcaacctgaagattttgcaacttactactgtcaacagagttacagtaccccggggacgttcggccaa gggaccaaggtggaaatcaaa | 2 |
| WNV-10 heavy | caggtgcagctggtggagtcggggggaggcgtggtccagcctgggaggtccctgagactctcctgtgcagcctct ggattccaccttcagtagtcatgctatgcactgggtccgccaggctccaggcaagggctggagtgggtggcagtt atatcatatgatataatcaatgaatattacgcagactccgtgaagggccgattcaccatctccagagacaattcc aagaacacgctgtatctgcaaatgaatagcctgagagctgaggacacggctgtttattactgtgcgagagacgg gtactttcctaatagtagtggtgagggggttctttgactactggggccagggaaccctggtcaccgtctcctca | 3 |

TABLE 1-continued

NUCLEOTIDE SEQUENCES FOR ANTIBODY VARIABLE REGIONS

| Clone | Variable Sequence Region | SEQ ID NO: |
|---|---|---|
| WNV-10 light | gaaattgtgatgacgcagtctccagccaccctgtctgtgtctccaggggaaagagccaccctctcctgcagggcc agtcagagtcttagtaacaacttagcctggtaccagcagaaacctggccaggctcccaggctcctcatctatggt gcatccaccagggccactggtatcccagccaggttcagtggcagtgggtctgggacacagttcactctcaccatc agcagcctgcagtctgaagatattgcagtttattactgtcagcagttcaataactggccgtggacgttcggccaa gggaccaaggtggaaatcaaa | 4 |
| WNV-13 heavy | caggtgcagctggtggagtctgggggaggcgtggtccaacctggggaggtccctgagactttcctgtgcagcctct ggattcatttcgagaactatggcatgcactgggtccgccaggctccaggcaaggggctggagtgggtggcagtt atttcatatgatggagataacaaagactatagtaagtccgtgaagggccgattcaccatctccagagacaattcc aagaacacgctgcatttgcagatgaacagcctgagaactgaagacacggctgtgtactactgtgcaaaagaac caagtaagagttggttccgtttctttgagacttggggccagggaaccctggtcaccgtctcctcag | 5 |
| WNV-13 light | cagattgtgctgactcaggcaccctcggtgtcagtggcccaggacagacggccaggattacctgtgggggcac tggaagtaaaggtgtgcactggtaccagcagaagccaggccaggcccctgtggtggtcgtccatgatgatagcg accggcccctcagggatccctgggcgattctctggctccaactctgggaacgcggccatgctgaccatcagcagg gtcgaagccggggatgaggccgactattactgtcaggtgtgggatagtgtcagtgacgtggttttcggcggagg gaccaagctgaccgtccta | 6 |
| WNV-15 heavy | caggtgcagctggtggagtctgggggaggcttggtcaagcctggagggtccctgagactctcctgtgtagcctct ggattccccttcagtgagtcctacatgagctggattcgccaggctccagggaaggggctggagtgggtctcatac attagtagtagtagttacacaaatttatgcagactctgtgaagggccgattcaccatctccagagacaacgcc aagaactcactgtgatctgcagatgaacagcctgagagtcgacgacacggctgtatattactgtgtgagagatgg cattcttaattactatgctgggggaagtaaagactactggggccagggaaccctggtcaccgtctcctca | 7 |
| WNV-15 light | cagtctgccctgactcagcctgcctccgtgtctgggtctcctggacagtcgatcaccatctcctgcactggaacca gcagtgatattgggacttatacccttgtctcctggtaccagcaacacccaggcaaagcccccaaactcatgattt atgagggcagtaagcggccctcaggggtttctaatcgcttctctggctccaagtctggcaacacggcctcctga caatctctggccttcaggctgaggacgaggctgattattactgctgctcatatgcaggtagcaatattcctctattc ggcggagggaccaaggtgaccgtccta | 8 |
| WNV-18 heavy | caggtcaccttgagggagtctggtcctgcgctggtgaaacccacacagaccctcacactgacctgcaccttctct gggttctcactcaccactagtggaatgtgtgtaagctggatccgtcagaccccagggaaggccctggagtggctt gctctcattgattgggaagatgataaatactacaacatctctgaagacaggctcaccatctccaaggacacc tccaaaaaccaggtggtcctacaatgaccaacatggaccctgtggacacaggcacatattactgtgcacgggg cacagggagggataaagccatggttttcgtctactggggccagggaaccctggtcaccgtctcctca | 9 |
| WNV-18 light | gacatcgtgatgactcagtctccagattccctggctgtgtctctgggcgagagggccaccatcaactgcaagtcc agccagagtgttttatacaggtccaataataagaacttcttagcttggtaccagcagaaaccaggacagcctcct aagctgctcatttcctgggcatctacccgggaacccgggatccctgaccgcttcagtggcagcgggtctgggaca gatttcactctcaccatcagcagcctgcaggctgaggatgtggcagtttattactgtcagcaatattatagtgctcc ccttttcggcggagggaccaaggtggagatcaaa | 10 |
| WNV-39 heavy | gaggtgcagctggtggagtctgggggaggcttggtccggcctgggggtccctgagactctcctgtgcagctct ggattcaccttcagtagctatgctttgcactggctccgccaggctccagggaagggactggaatatgtttcatcta ttaatgataacgggcgtcttacattttatgcaaactctgtgaagggcagattcaccatctccagagacaattccaa gaacaccctctatcttcaaatgggccgctgagagctgacgacatggctgtgtattactgtgcgagaggattcga tgaaaatactggttattaccttgacaactggggccagggaaccctggtcaccgtctcctca | 11 |
| WNV-39 light | cagtctgtgttgactcagccgccctcagtgtctgcggccccaagacagaaggtcaccatctcctgctctggaacc agctccaacattgggaataattatgtatcctggtaccagcagctcccaggaacagcccccagactcctcatttat gacaataataggcgaccctcagggattcctgaccgattctctggctccaagtctggcacgtcagccaccctggac atcaccggactccagactgggacgaggccgactattattgcggaacatgggatagcagcctgagttttgtggtg ttcggcggagggaccaagctgaccgtccta | 12 |
| WNV-57 heavy | caggtgcagctggtggagtctgggggaggcgtggtccagcctgggcggtccctgagactcgcctgtgcagcctct ggattcaccttaagtgactttgccatacactgggtccgccaggctccaggcaaggggctggagtgggtggcaatc atatcatatgatggaaacatcaaatactacgcagactccgtgaagggccgcttcaccatctccagtgacaattcc aagaacacggtctatctccaaatgaacagcctgagagctgaggacacggctgtgtattactgtgcgagaaatcc tgatgtggtggagactgcccacgatgcttttgatatctggggccaagggaccctggtcaccgtctcctca | 13 |
| WNV-57 light | gacatcctgatgacccagtctccatcctccctgtctgcatctgtaggagacagagtcaccatcacttgccgggcta gtcagaacattaagaattatttaaattggtatcagcagaaaccagggaaagcccctaaactccttatctatgctg catccagtttacagagtttagtcccatcaaggttcagtggcagtgggtctgggacagatttcactctcaccatcag cagtctgcaacctgaagattttgcaacttactactgtcaacagagttacagttcttccggacgttcggccaaggg accaaggtggaagtcaaa | 14 |
| WNV-61 heavy | caggtgcagctggtggagtctgggggaggcgtggtccagcctgggaggtccctgagactctcctgtgtaggctct ggattcagcctcagtgattatgctatgcactgggtccgccaggctccagggggggctggagtgggtggcagtt atatcatatgatggaaggaatgcatattacgcagagtccgtgaagggccgattcatcatctccagagacaattcc aaaaacacactctatctacaaatgaccagcctgagaattgaggacacggctgtctattattgtgtgagagggga attcagtacgtcattttgtggtgctgactgcccctatcactactatggcatggacgtctggggccgagggaccctg gtcaccgtctcctca | 15 |

TABLE 1-continued

NUCLEOTIDE SEQUENCES FOR ANTIBODY VARIABLE REGIONS

| Clone | Variable Sequence Region | SEQ ID NO: |
|---|---|---|
| WNV-61 light | caggctgtggtgactcaggagccctcactgactgtgtccccaggagggacagtcactctcacctgtgcctctacc gctggagctgtcaccagtgatctttttcccttctggctccagcagaagcctggccaagcccccaggacacttattt ataatacaaacaaactgtactcctggaccccagcccggttctcaggctccctctttgggggtaaagctgccctga ccctttcgggtgcgcagcctgaagatgaggctgaatattactgcctgctctcctatgctggtgctcgcttgttcggc ggagggaccaagttgaccgtcctg | 16 |
| WNV-62 heavy | caggtgcagctggtggagtctgggggaggcgtggtccagcctgggaggtccctgagactttcatgtgcagcctct ggattcaccttcagtagttatggcatgcactgggtccgccaggctccaggcaaggggctggagtgggtggcagtt atgtcttatgatggaagtaagatatactatgcagactccgtgaagggccgattcaccatctccagagacaattcc aagaacacgctgtatctgcaaatggacagcctgagagctgaggacacggctgtgtattactgtgcgaaagttgg ttattatgatggtagtcgttatgacctaatcgctgaatacttccagtactggggccagggcaccctggtcaccgtct cctca | 17 |
| WNV-62 light | cagtctgtgctgactcagccgccctcagtgtctggggccgcagggcagagggtcaccatctcctgcactgggagc agctccaacatcggggcaggttatgatgtacactggtatcagcaacttccaggaacagcccccaaactcctcatc tatggtaacaacaatcggccctcaggggtccctgaccgattctctggctccaagtctgacacttcagcctccctgg ccatcactgggctccggcctgaggatgaacttgattattactgccagtcctatgacaacaggctgagtgcttatgt cttcggaactgggaccaaggtcaccgtccta | 18 |
| WNV-86 heavy | caggtgcagctggtgcagtctgggggaggcctggtacagcctggcaggtccctgagactctgctgtgcagcctct ggattcagctttgatgattttgccatgcactgggtccggcaagctccagggaagggcctggagtgggtctcaggt attaattggaatagtggtcacataggctatgcggactctgtgaagggccgattcaccatctccagagacaacgcc aagaactccctgtgtctgcaaatgaacagtctgagacctgaggacacggccttgtattactgtgcaaaagatcgg gcgtattactttggttcagggacctcaggtggtgcttttgatgtctggggccaagggaccctggtcaccgtctcctc a | 19 |
| WNV-86 light | gacatcgtgatgacccagtctccatcgtccctgtctgcatctgtaggagacagagtcaccatcacttgccgggca agtcagaacattatcagctatttaaattggtatcagcagaaaccagggaaagcccctaagctcctgatctatgat gcatccagtttgcaaagtggggtcccatcaaggttcagtggcagtggttctgggacagatttcactctcaccatca gcagtctgcaacctgaagattttgcaacttactactgtcaaaggagttttagtaccccgctcactttcggcggagg gaccaaggtggagatcaaa | 20 |

TABLE 2

PROTEIN SEQUENCES FOR ANTIBODY VARIABLE REGIONS

| Clone | Variable Sequence | SEQ ID NO. |
|---|---|---|
| WNV-6 heavy | QVQLVQSGAEVKKPGASVNISCKASGYTFTNYFIHWVRQAPGQGLEWMGMINPRGGS THFAQKFQARVTMTRDTSTNTVYMELSSLRSEDTAMYYCAKGICKISFMCPFDPWGQG TLVTVSS | 21 |
| WNV-6 light | DIVMTQSPASLSASVRDRVTITCRASQSINNHVNWYQQKPGKAPKLLIYSTSSLQSGVPSR FSGSGSGTDFTLTISSLQPEDFATYYCQQSYSTPGTFGQGTKVEIK | 22 |
| WNV-10 heavy | QVQLVESGGGVVQPGRSLRLSCAASGFTFSSHAMHWVRQAPGKGLEWVAVISYDIINEY YADSVKGRFTISRDNSKNTLYLQMNSLRAEDTAVYYCARDGYFPNSSGEGFFDYWGQGT LVTVSS | 23 |
| WNV-10 light | EIVMTQSPATLSVSPGERATLSCRASQSLSNNLAWYQQKPGQAPRLLIYGASTRATGIPA RFSGSGSGTQFTLTISSLQSEDIAVYYCQQFNNWPWTFGQGTKVEIK | 24 |
| WNV-13 heavy | QVQLVESGGGVVQPGRSLRLSCAASGFIFENYGMHWVRQAPGKGLEWVAVISYDGDN KDYSKSVKGRFTISRDNSKNTLHLQMNSLRTEDTAVYYCAKEPSKSWFRFFETWGQGTLV TVSS | 25 |
| WNV-13 light | QIVLTQAPSVSVAPGQTARITCGGTGSKGVHWYQQKPGQAPVVVVHDDSDRPSGIPGR FSGSNSGNAAMLTISRVEAGDEADYYCQVWDSVSDVVFGGGTKLTVL | 26 |
| WNV-15 heavy | QVQLVESGGGLVKPGGSLRLSCVASGFTFSESYMSWIRQAPGKGLEWVSYISSSSSYTNY ADSVKGRFTISRDNAKNSLDLQMNSLRVDDTAVYYCVRDGILNYYAGGSKDYWGQGTL VTVSS | 27 |
| WNV-15 light | QSALTQPASVSGSPGQSITISCTGTSSDIGTYTLVSWYQQHPGKAPKLMIYEGSKRPSGVS NRFSGSKSGNTASLTISGLQAEDEADYYCCSYAGSNIPLFGGGTKVTVL | 28 |

TABLE 2-continued

PROTEIN SEQUENCES FOR ANTIBODY VARIABLE REGIONS

| Clone | Variable Sequence | SEQ ID NO. |
|---|---|---|
| WNV-18 heavy | QVTLRESGPALVKPTQTLTLTCTFSGFSLTTSGMCVSWIRQTPGKALEWLALIDWEDDKY YNTSLKTRLTISKDTSKNQVVLTMTNMDPVDTGTYYCARGTGRDKAMVFVYWGQGTLV TVSS | 29 |
| WNV-18 light | DIVMTQSPDSLAVSLGERATINCKSSQSVLYRSNNKNFLAWYQQKPGQPPKLLISWASTR EPGIPDRFSGSGSGTDFTLTISSLQAEDVAVYYCQQYYSAPLFGGGTKVEIK | 30 |
| WNV-39 heavy | EVQLVESGGGLVRPGGSLRLSCAGSGFTFSSYALHWLRQAPGKGLEYVSSINDNGRLTFY ANSVKGRFTISRDNSKNTLYLQMGRLRADDMAVYYCARGFDENTGYYLDNWGQGTLVT VSS | 31 |
| WNV-39 light | QSVLTQPPSVSAAPRQKVTISCSGTSSNIGNNYVSWYQQLPGTAPRLLIYDNNRRPSGIPD RFSGSKSGTSATLDITGLQTGDEADYYCGTWDSSLSFVVFGGGTKLTVL | 32 |
| WNV-57 heavy | QVQLVESGGGVVQPGRSLRLACAASGFTLSDFAIHWVRQAPGKGLEWVAIISYDGNIKY YADSVKGRFTISSDNSKNTVYLQMNSLRAEDTAMYYCARDPDVVETAHDAFDIWGQGT LVTVSS | 33 |
| WNV-57 light | DILMTQSPSSLSASVGDRVTITCRASQNIKNYLNWYQQKPGKAPKLLIYAASSLQSLVPSR FSGSGSGTDFTLTISSLQPEDFATYYCQQSYSSFRTFGQGTKVEVK | 34 |
| WNV-61 heavy | QVQLVESGGGVVQPGRSLRLSCVGSGFSLSDYAMYWVRQAPGRGLEWVAVISYDGRN AYYAESVKGRFIISRDNSKNTLYLQMTSLRIEDTAVYYCVRGEFSTSFCGADCPYHYYGMD VWGRGTLVTVSS | 35 |
| WNV-61 light | QAVVTQEPSLTVSPGGTVTLTCASTAGAVTSDLFPFWLQQKPGQAPRTLIYNTNKLYSWT PARFSGSLFGGKAALTLSGAQPEDEAEYYCLLSYAGARLFGGGTKLTVL | 36 |
| WNV-62 heavy | QVQLVESGGGVVQPGRSLRLSCAASGFTFSSYGMHWVRQAPGKGLEWVAVMSYDGSK IYYADSVKGRFTISRDNSKNTLYLQMDSLRAEDTAVYYCAKVGYYDGSRYDLIAEYFQYW GQGTLVTVSS | 37 |
| WNV-62 light | QSVLTQPPSVSGAAGQRVTISCTGSSSNIGAGYDVHWYQQLPGTAPKLLIYGNNNRPSG VPDRFSGSKSDTSASLAITGLRPEDELDYYCQSYDNRLSAYVFGTGTKVTVL | 38 |
| WNV-86 heavy | QVQLVQSGGGLVQPGRSLRLCCAASGFSFDDFAMHWVRQAPGKGLEWVSGINWNSG HIGYADSVKGRFTISRDNAKNSLCLQMNSLRPEDTALYYCAKDRAYYFGSGTSGGAFDV WGQGTLVTVSS | 39 |
| WNV-86 light | DIVMTQSPSSLSASVGDRVTITCRASQNIISYLNWYQQKPGKAPKLLIYDASSLQSGVPSRF SGSGSGTDFTLTISSLQPEDFATYYCQRSFSTPLTFGGGTKVEIK | 40 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| WNV-6 | GYTFTNYF (41) | INPRGGST (42) | AKGICKISFMCPFDP (43) |
| WNV-10 | GFTFSSHA (44) | ISYDIINE (45) | ARDGYFPNSSGEGFFDY (46) |
| WNV-13 | GFIFENYG (47) | ISYDGDNK (48) | AKEPSKSWFRFFET (49) |
| WNV-15 | GFTFSESY (50) | ISSSSSYT (51) | VRDGILNYYAGGSKDY (52) |
| WNV-18 | GFSLTTSGMC (53) | IDWEDDK (54) | ARGTGRDKAMVFVY (55) |
| WNV-39 | GFTFSSYA (56) | INDNGRLT (57) | ARGFDENTGYYLDN (58) |
| WNV-57 | GFTLSDFA (59) | ISYDGNIK (60) | ARDPDVVETAHDAFDI (61) |
| WNV-61 | GFSLSDYA (62) | ISYDGRNA (63) | VRGEFSTSFCGADCPYHYYGMDV (64) |
| WNV-62 | GFTFSSYG (65) | MSYDGSKI (66) | AKVGYYDGSRYDLIAEYFQY (67) |
| WNV-86 | GFSFDDFA (68) | INWNSGHI (69) | AKDRAYYFGSGTSGGAFDV (70) |

TABLE 4

CDR LIGHT CHAIN SEQUENCES

| Antibody | CDRH1 (SEQ ID NO:) | CDRH2 (SEQ ID NO:) | CDRH3 (SEQ ID NO:) |
|---|---|---|---|
| WNV-6 | QSINNH (71) | STS (72) | QQSYSTPGT (73) |

TABLE 4-continued

CDR LIGHT CHAIN SEQUENCES

| Antibody | CDRH1 (SEQ ID NO:) | CDRH2 (SEQ ID NO:) | CDRH3 (SEQ ID NO:) |
|---|---|---|---|
| WNV-10 | QSLSNN (74) | GAS (75) | QQFNNWPWT (76) |
| WNV-13 | GTGSKG (77) | DDS (78) | QVWDSVSDVV (79) |
| WNV-15 | SSDIGTYTL (80) | EGS (81) | CSYAGSNIPL (82) |
| WNV-18 | QSVLYRSNNKNF (83) | WAS (84) | QQYYSAPL (85) |
| WNV-39 | SSNIGNNY (86) | DNN (87) | GTWDSSLSFVV (88) |
| WNV-57 | QNIKNY (89) | AAS (90) | QQSYSSFRT (91) |
| WNV-61 | AGAVTSDLF (92) | NTN (93) | LLSYAGARL (94) |
| WNV-62 | SSNIGAGYD (95) | GNN (96) | QSYDNRLSAYV (97) |
| WNV-86 | QNIISY (98) | DAS (99) | QRSFSTPLT (100) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., Am. J. Pediatr. Hematol. Oncol., 12(4), 480-489, 1990.
Allred et al., Arch. Surg., 125(1), 107-113, 1990.
Ansarah-Sobrinho et al., Virology 381, 67-74, doi:10.1016/j.virol.2008.08.021, 2008.
Atherton et al., Biol. of Reproduction, 32, 155-171, 1985.
Barba-Spaeth et al., Nature 536, 48-53, doi:10.1038/nature18938, 2016.
Barzon et al., Euro Surveill. 2016 Aug. 11; 21(32).
Beasley, D. W. & Barrett, A. D., J Virol 76, 13097-13100, 2002.
Belmusto-Wom et al., Am J Trop Med Hyg 72, 189-197, 2005.
Beltramello et al., Cell Host Microbe 8, 271-283, 2010.
Ben-Nathan et al., J Infect Dis 188, 5-12, doi:10.1086/376870, 2003.
Brown et al., J. Immunol. Meth., 12; 130(1): 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
Capeding et al., Lancet 384, 1358-1365, doi:10.1016/S0140-6736(14)61060-6, 2014.
Center for Disease Control. West Nile virus. Atlanta, GA: US Department of Health and Human Services, CDC; 2016.
Cherrier et al., EMBO J 28, 3269-3276, doi:10.1038/emboj.2009.245; 2009.
Choi et al., Virus Res 123, 216-218, doi:10.1016/j.virusres.2006.09.002, 2007.
Crill, W. D. & Chang, G. J., J Virol 78, 13975-13986, doi:10.1128/JVI.78.24.13975-13986.2004, 2004.
Davis et al., J Virol 80, 1290-1301, doi:10.1128/JVI.80.3.1290-1301.2006, 2006.
de Alwis et al., Proc Natl Acad Sci USA 109, 7439-7444, doi:10.1073/pnas.1200566109, 2012.
De Jager et al., Semin. Nucl. Med. 23(2), 165-179, 1993.
Dejnirattisai et al., Nat Immunol 16, 170-177, doi:10.1038/ni.3058, 2015.
Dholakia et al., J. Biol. Chem., 264, 20638-20642, 1989.
Diamond et al., J Virol 77, 2578-2586, 2003.
Doolittle and Ben-Zeev, Methods Mol. Biol., 109: 215-237, 1999.
Dowd et al., Cell Rep 16, 1485-1491, doi:10.1016/j.celrep.2016.07.049, 2016.
Duffy et al., N Engl J Med 2009; 360 (24) 2536-2543
Duffy et al., N. Engl. J Med. 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Engle, M. J. & Diamond, M. S., J Virol 77, 12941-12949, 2003.
Fibriansah et al., Nat Commun 6, 6341, doi:10.1038/ncomms7341, 2015.
Fibriansah et al., Science 349, 88-91, doi:10.1126/science.aaa8651, 2015.

Gefter et al., *Somatic Cell Genet.*, 3:231-236, 1977.
Goncalvez et al., *J Virol* 78, 12919-12928, doi:10.1128/JVI.78.23.12919-12928.2004, 2004.
Gornet et al., *Semin Reprod Med.* 2016 September; 34(5): 285-292. Epub 2016 Sep. 14.
Gould et al., *J Virol* 79, 14606-14613, doi:10.1128/JVI.79.23.14606-14613.2005, 2005.
Guirakhoo et al., *Virology* 191, 921-931, 1992.
Gulbis and Galand, *Hum. Pathol.* 24(12), 1271-1285, 1993.
Halfon et al., *PLoS ONE* 2010; 5 (5) e10569
Hasan et al., *Nat Commun* 8, 14722, doi:10.1038/ncomms14722, 2017.
Heinz et al., *Virology* 198, 109-117, doi:10.1006/viro.1994.1013, 1994.
Hessell et al., *Nature* 449, 101-4, 2007.
Kaufmann et al., *Proc Natl Acad Sci USA* 107, 18950-18955, doi:10.1073/pnas.1011036107, 2010.
Khatoon et al., *Ann. of Neurology*, 26, 210-219, 1989.
King et al., *J Biol. Chem.*, 269, 10210-10218, 1989.
Kohler and Milstein, *Eur. J Immunol.*, 6, 511-519, 1976.
Kohler and Milstein, *Nature*, 256, 495-497, 1975.
Kostyuchenko et al., *Nature* 533, 425-428, doi:10.1038/nature17994, 2016.
Kuhn et al., *Cell* 108, 717-725, 2002.
Kyte and Doolittle, *J. Mol. Biol.*, 157(1):105-132, 1982.
Lai et al., *J Virol* 82, 6631-6643, doi:10.1128/NI.00316-08, 2008.
Li et al., *Virology* 335, 99-105, doi:10.1016/j.virol.2005.02.011, 2005.
Lin et al., *J Virol* 86, 3501-3512, doi:10.1128/JVI.06435-11; 2012.
Mansuy et al., *Lancet Infect Dis.* 2016 October; 16(10): 1106-7.
Markoff, L., *Vaccine* 18 Suppl 2, 26-32, 2000.
Mukhopadhyay et al., *Science* 302, 248, doi:10.1126/science.1089316, 2003.
Nakamura et al., In: *Enzyme Immunoassays: Heterogeneous and Homogeneous Systems*, Chapter 27, 1987.
Nelson et al., *PLoS Pathog* 4, e1000060, doi:10.1371/journal.ppat.1000060, 2008.
Nybakken et al., *Nature* 437, 764-769, doi:10.1038/nature03956, 2005.
Oliphant et al., *J Virol* 80, 12149-12159, doi:10.1128/NI.01732-06; 2006.
Oliphant et al., *J Virol* 81, 11828-11839, doi:10.1128/NI.00643-07, 2007.
Oliphant et al., *Nat Med* 11, 522-530, doi:10.1038/nm1240, 2005.
O'Shannessy et al., *J. Immun. Meth.*, 99, 153-161, 1987.
Persic et al., *Gene* 187:1, 1997
Pierson et al., *Cell Host Microbe* 1, 135-145, doi:10.1016/j.chom.2007.03.002, 2007.
Pierson et al., *Virology* 346, 53-65, doi:10.1016/j.virol.2005.10.030, 2006.
Pierson, T. C. & Diamond, M. S., *Curr Opin Virol* 2, 168-175, doi:10.1016/j.coviro.2012.02.011, 2012.
Potter and Haley, *Meth. Enzymol.*, 91, 613-633, 1983.
Purpura et al., *Lancet Infect Dis.* 2016 October; 16(10): 1107-8. Epub 2016 Sep. 19.
R. C. Team, R Foundation for Statistical Computing, Vienna, Austria, 2014.
Remington's Pharmaceutical Sciences, 15th Ed., 3:624-652, 1990.
Roehrig et al., *Ann NY Acad Sci* 951, 286-297, 2001.
Sanchez et al., *Virology* 336, 70-82, doi:10.1016/j.virol.2005.02.020, 2005.
Sapparapu et al., *Nature* 540, 443-447, doi:10.1038/nature20564, 2016.
Sirohi et al., *Science* 352, 467-470, doi:10.1126/science.aaf5316, 2016.
Smith et al., *J Virol* 86, 2665-2675, doi:10.1128/JVI.06335-11, 2012.
Smith et al., *MBio* 4, e00873-00813, doi:10.1128/mBio.00873-13, 2013.
Tang et al., *J Biol. Chem.*, 271, 28324-28330, 1996.
Teoh et al., *Sci Transl Med* 4, 139ra183, doi:10.1126/scitranslmed.3003888, 2012.
Throsby et al., *J Virol* 80, 6982-6992, doi:10.1128/JVI.00551-06, 2006.
VanBlargan et al., *Microbiol Mol Biol Rev* 80, 989-1010, doi:10.1128/MMBR.00024-15, 2016.
Villar et al., *N Engl J Med* 372, 113-123, doi:10.1056/NEJMoa1411037, 2015.
Wawrzynczak & Thorpe, In: *Immunoconjugates, Antibody Conuugates In Radioimaging And Therapy Of Cancer*, Vogel (Ed.), NY, Oxford University Press, 28, 1987.
Yu et al., *J Immunol Methods* 336, 142-151, doi:10.1016/j.jim.2008.04.008, 2008.
Zhang et al., *J Infect Dis* 200, 202-205, doi:10.1086/599794, 2009.
Zhang et al., *Nat Commun* 7, 13679, doi:10.1038/ncomms13679, 2016.
Zhang et al., *Nat Struct Mol Biol* 20, 105-110, doi:10.1038/nsmb.2463, 2013.

What is claimed is:

1. A method of detecting a West Nile virus infection in a subject comprising:
   (a) contacting a sample from said subject with an antibody or antigen-binding fragment thereof comprising heavy and light chain CDR1-3 sequences of SEQ ID NOS: 68-70 and 98-100, respectively, wherein the antibody or antigen-binding fragment thereof binds to West Nile Virus E protein; and
   (b) detecting West Nile virus in said sample by binding of said antibody or antigen-binding fragment thereof to West Nile virus E protein in said sample.

2. A method of inhibiting West Nile virus (WNV) in a subject infected with WNV comprising administering to said subject an antibody or antigen-binding fragment thereof comprising heavy and light chain CDR1-3 sequences of SEQ ID NOS: 68-70 and 98-100, respectively, wherein the antibody or antigen-binding fragment thereof binds to WNV E protein.

3. The method of claim 2, the antibody or antigen-binding fragment thereof is encoded by heavy and light chain variable sequences comprising SEQ ID NOS: 19 and 20, respectively.

4. The method of claim 2, the antibody or antigen-binding fragment thereof is encoded by heavy and light chain variable sequences having 95% identity to sequences comprising SEQ ID NOS: 19 and 20, respectively.

5. The method of claim 2, wherein said antibody or antigen-binding fragment thereof is encoded by heavy and light chain variable sequences having 70%, 80%, or 90% identity to sequences comprising SEQ ID NOS: 19 and 20, respectively.

6. The method of claim 2, wherein said antibody or antigen-binding fragment thereof comprises heavy and light chain variable sequences comprising SEQ ID NOS: 39 and 40, respectively.

7. The method of claim 2, wherein said antibody or antigen-binding fragment thereof comprises heavy and light chain variable sequences having 70%, 80% or 90% identity to SEQ ID NOS: 39 and 40, respectively.

8. The method of claim 2, wherein said antibody or antigen-binding fragment thereof comprises heavy and light chain variable sequences having 95% identity to SEQ ID NOS: 39 and 40, respectively.

9. The method of claim 2, wherein the antigen-binding fragment thereof is a recombinant scFv (single chain fragment variable) antibody, Fab fragment, F(ab')$_2$ fragment, or Fv fragment.

10. The method of claim 2, wherein said antibody is an IgG, or a recombinant IgG antibody or antigen-binding fragment thereof comprising an Fc portion mutated to eliminate FcR interactions.

11. The method of claim 2, wherein said antibody is a chimeric antibody or a bispecific antibody.

12. The method of claim 2, wherein said antibody or antigen-binding fragment thereof is administered prior to infection or after infection.

13. The method of claim 2, wherein said subject is a pregnant female, a sexually active female, or a female undergoing fertility treatments.

14. A method of inhibiting West Nile virus (WNV) infection in a subjected infected with WNV comprising administering to said subject an RNA or DNA sequence or vector encoding antibody or antigen-binding fragment thereof comprising heavy and light chain CDR1-3 sequences of SEQ ID NOS: 68-70 and 98-100, respectively, wherein the antibody or antigen-binding fragment thereof binds to WNV E protein.

15. A monoclonal antibody or antigen-binding fragment thereof, wherein the antibody or antigen-binding fragment comprises heavy and light chain CDR1-3 sequences of SEQ ID NOS: 68-70 and 98-100, respectively, wherein the antibody or antigen-binding fragment thereof contains an Fc portion mutated to eliminate FcR interactions, and wherein the antibody or antigen-binding fragment thereof binds to West Nile Virus E protein.

16. An isolated, engineered cell that expresses an antibody or antigen-binding fragment thereof, wherein the antibody or antigen-binding fragment thereof comprises heavy and light chain CDR1-3 sequences of SEQ ID NOS: 68-70 and 98-100, respectively, wherein the antibody or antigen-binding fragment thereof binds to West Nile Virus E protein.

17. A pharmaceutical formulation comprising one or more antibodies or antigen binding fragments thereof, wherein at least one of the antibodies or antigen-binding fragments thereof comprises heavy and light chain CDR1-3 sequences of SEQ ID NOS: 68-70 and 98-100, respectively, and wherein the antibody or antigen-binding fragment thereof binds to West Nile Virus E protein.

18. A method of determining the antigenic integrity of a West Nile Virus E antigen comprising:
   (a) contacting a sample comprising said antigen with a first antibody or antigen-binding fragment thereof comprising heavy and light chain CDR1-3 sequences of SEQ ID NOS: 68-70 and 98-100, respectively, wherein the antibody or antigen-binding fragment thereof binds to West Nile Virus E protein; and
   (b) determining antigenic integrity of said antigen by detectable binding of said first antibody or antigen-binding fragment thereof to said antigen.

19. The method of claim 10, wherein the Fc portion is mutated to eliminate FcR interactions comprises a LALA mutation.

20. The monoclonal antibody of claim 15, wherein the Fc portion is mutated to eliminate FcR interactions comprises a LALA mutation.

* * * * *

SEQUENCE LISTING

```
<160> NUMBER OF SEQ ID NOS: 100

<210> SEQ ID NO 1
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtgcagtc tggggctgag gtgaagaagc ctggggcctc agtgaacatt      60
tcctgcaagg catctggata caccttcacc aactacttta tccactgggt gcgacaggcc     120
cctggacaag gccttgagtg gatggggatg atcaacccct cgtggtggcag cacacacttc     180 gcacagaagt tccaggccag agtcaccatg accagggaca tccacgaa tacagtttat        240
```

```
atggaactga gcagcctgag atctgaggac acggccatgt attactgtgc taaaggaatc    300
tgtaaaatct catttatgtg tcccttcgac ccctggggcc agggaaccct ggtcaccgtc    360
tcctca                                                                366
```

<210> SEQ ID NO 2
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 2

```
gacatcgtga tgacccagtc tccagcctcc ctgtctgcat ctgtaagaga cagagtcacc     60
atcacttgcc gggcaagtca gagcattaac aaccatgtaa attggtatca gcagaagccg    120
gggaaggccc ctaaactcct gatctacagt acatccagtt tgcaaagtgg ggtcccatcc    180
aggttcagtg gcagtggatc tgggacagat ttcactctca ccatcagcag tctgcaacct    240
gaagattttg caacttacta ctgtcaacag agttacagta ccccggggac gttcggccaa    300
gggaccaagg tggaaatcaa a                                              321
```

<210> SEQ ID NO 3
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 3

```
caggtgcagc tggtggagtc ggggggaggc gtggtccagc ctgggaggtc cctgagactc     60
tcctgtgcag cctctggatt caccttcagt agtcatgcta tgcactgggt ccgccaggct    120
ccaggcaagg ggctgagtg gtggcagtt atatcatatg atataatcaa tgaatattac    180
gcagactccg tgaagggccg attcaccatc tccagagaca attccaagaa cacgctgtat    240
ctgcaaatga atagcctgag agctgaggac acggctgttt attactgtgc gagagacggg    300
tactttccta atagtagtgg tgaggggttc tttgactact ggggccaggg aaccctggtc    360
accgtctcct ca                                                        372
```

<210> SEQ ID NO 4
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 4

```
gaaattgtga tgacgcagtc tccagccacc ctgtctgtgt ctccagggga aagagccacc     60
ctctcctgca gggccagtca gagtcttagt aacaacttag cctggtacca gcagaaacct    120
ggccaggctc ccaggctcct catctatggt gcatccacca gggccactgg tatcccagcc    180
aggttcagtg gcagtgggtc tgggacacag ttcactctca ccatcagcag cctgcagtct    240
gaagatattg cagtttatta ctgtcagcag ttcaataact ggccgtggac gttcggccaa    300
gggaccaagg tggaaatcaa a                                              321
```

<210> SEQ ID NO 5
<211> LENGTH: 364
<212> TYPE: DNA

<213> ORGANISM: Artificial sequence
<220> FEATURE:
<223> OTHER INFORMATION: Synthetic oligonucleotide

<400> SEQUENCE: 5

```
caggtgcagc tggtggagtc tgggggaggc gtggtccaac ctgggaggtc cctgagactt    60
tcctgtgcag cctctggatt cattttcgag aactatggca tgcactgggt ccgccaggct   120
ccaggcaagg ggctggagtg ggtggcagtt atttcatatg atggagataa caaagactat   180
agtaagtccg tgaagggccg attcaccatc tccagagaca attccaagaa cacgctgcat   240
ttgcagatga acagcctgag aactgaagac acggctgtgt actactgtgc aaaagaacca   300
agtaagagtt ggttccgttt ctttgagact tggggccagg aaccctggt caccgtctcc   360
tcag                                                                364
```

<210> SEQ ID NO 6
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 6

```
cagattgtgc tgactcaggc accctcggtg tcagtggccc caggacagac ggccaggatt    60
acctgtgggg gcactggaag taaaggtgtg cactggtacc agcagaagcc aggccaggcc   120
cctgtggtgg tcgtccatga tgatagcgac cggccctcag ggatccctgg gcgattctct   180
ggctccaact ctgggaacgc ggccatgctg accatcagca gggtcgaagc cggggatgag   240
gccgactatt actgtcaggt gtgggatagt gtcagtgacg tggttttcgg cggagggacc   300
aagctgaccg tccta                                                    315
```

<210> SEQ ID NO 7
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtggagtc tgggggaggc ttggtcaagc ctggagggtc cctgagactc    60
tcctgtgtag cctctggatt caccttcagt gagtcctaca tgagctggat ccgccaggct   120
ccagggaagg ggctggagtg ggtctcatac attagtagta gtagtagtta cacaaattat   180
gcagactctg tgaagggccg attcaccatc tccagagaca cgccaagaa ctcactggat   240
ctgcagatga acagcctgag agtcgacgac acggctgtat attactgtgt gagagatggc   300
attcttaatt actatgctgg gggaagtaaa gactactggg gccagggaac cctggtcacc   360
gtctcctca                                                           369
```

<210> SEQ ID NO 8
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 8

```
cagtctgccc tgactcagcc tgcctccgtg tctgggtctc ctggacagtc gatcaccatc    60
tcctgcactg gaaccagcag tgatattggg acttataccc ttgtctcctg gtaccagcaa   120
```

```
cacccaggca aagcccccaa actcatgatt tatgagggca gtaagcggcc ctcaggggtt    180
tctaatcgct tctctggctc caagtctggc aacacggcct ccctgacaat ctctggcctt    240
caggctgagg acgaggctga ttattactgc tgctcatatg caggtagcaa tattcctcta    300
ttcggcggag ggaccaaggt gaccgtccta                                     330
```

<210> SEQ ID NO 9
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 9

```
caggtcacct tgagggagtc tggtcctgcg ctggtgaaac ccacacagac cctcacactg     60
acctgcacct tctctggggtt ctcactcacc actagtggaa tgtgtgtaag ctggatccgt    120
cagaccccag ggaaggccct ggagtggctt gctctcattg attgggaaga tgataaatac    180
tacaacacct ctctgaagac caggctcacc atctccaagg acacctccaa aaaccaggtg    240
gtccttacaa tgaccaacat ggaccctgtg gacacaggca catattactg tgcacggggc    300
acagggaggg ataaagccat ggttttcgtc tactggggcc agggaaccct ggtcaccgtc    360
tcctca                                                               366
```

<210> SEQ ID NO 10
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 10

```
gacatcgtga tgactcagtc tccagattcc ctggctgtgt ctctgggcga gagggccacc     60
atcaactgca gtccagcca gagtgtttta tacaggtcca ataataagaa cttcttagct    120
tggtaccagc agaaaccagg acagcctcct aagctgctca tttcctgggc atctacccgg    180
gaacccggga tccctgaccg cttcagtggc agcgggtctg ggacagattt cactctcacc    240
atcagcagcc tgcaggctga ggatgtggca gtttattact gtcagcaata ttatagtgct    300 cccttttcg gcggagggac caaggtggag atcaaa                              336
```

<210> SEQ ID NO 11
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 11

```
gaggtgcagc tggtggagtc tgggggaggc ttggtccggc ctgggggtc cctgagactc      60 tcctgtgcag gctctggatt caccttcagt agctatgctt gcactggct ccgccaggct    120 ccagggaagg gactggaata tgtttcatct attaatgata cgggcgtct tacattttat    180 gcaaactctg tgaagggcag attcaccatc tccagagaca attccaagaa caccctctat    240
cttcaaatgg gccgcctgag agctgacgac atggctgtgt attactgtgc gagaggattc    300
gatgaaaata ctggttatta ccttgacaac tggggccagg gaaccctggt caccgtctcc    360
tca                                                                  363
```

<210> SEQ ID NO 12
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 12

```
cagtctgtgt tgactcagcc gccctcagtg tctgcggccc caagacagaa ggtcaccatc      60
tcctgctctg gaaccagctc caacattggg aataattatg tatcctggta ccagcagctc     120
ccaggaacag cccccagact cctcatttat gacaataata gcgcgaccctc agggattcct    180 gaccgattct ctggctccaa gtctggcacg tcagccaccc tggacatcac cggactccag     240 actgggacg aggccgacta ttattgcgga acatgggata gcagcctgag ttttgtggtg      300
ttcggcggag ggaccaagct gaccgtccta                                      330
```

<210> SEQ ID NO 13
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 13

```
caggtgcagc tggtggagtc tgggggaggc gtggtccagc ctgggcggtc cctgagactc      60
gcctgtgcag cctctggatt caccttaagt gactttgcca tacactgggt ccgccaggct     120
ccaggcaagg ggctggagtg ggtggcaatc atatcatatg atggaaacat caaatactac     180
gcagactccg tgaagggccg cttcaccatc tccagtgaca attccaagaa cacggtctat     240
ctccaaatga acagcctgag agctgaggac acggctatgt attactgtgc gagagatcct     300
gatgtggtgg agactgccca cgatgctttt gatatctggg gccaagggac cctggtcacc     360
gtctcctca                                                             369
```

<210> SEQ ID NO 14
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 14

```
gacatcctga tgacccagtc tccatcctcc ctgtctgcat ctgtaggaga cagagtcacc      60
atcacttgcc gggctagtca gaacattaag aattatttaa attggtatca gcagaaacca     120
gggaaagccc ctaaactcct tatctatgct gcatccagtt tacagagttt agtcccatca     180
aggttcagtg gcagtgggtc tgggacagat ttcactctca ccatcagcag tctgcaacct     240
gaagattttg caacttacta ctgtcaacag agttacagtt cttttccggac gttcggccaa     300 gggaccaagg tggaagtcaa a                                                321
```

<210> SEQ ID NO 15
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 15

```
caggtgcagc tggtggagtc tgggggaggc gtggtccagc ctgggaggtc cctgagactc      60
```

```
tcctgtgtag gctctggatt cagcctcagt gattatgcta tgtactgggt ccgccaggct    120
cctggcaggg ggctggagtg ggtggcagtt atatcatatg atggaaggaa tgcatattac    180
gcagagtccg tgaagggccg attcatcatc tccagagaca attccaaaaa cacactctat    240
ctacaaatga ccagcctgag aattgaggac acggctgtct attattgtgt gagaggggaa    300
ttcagtacgt cattttgtgg tgctgactgc ccctatcact actatggcat ggacgtctgg    360
ggccgaggga ccctggtcac cgtctcctca                                     390
```

<210> SEQ ID NO 16
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 16

```
caggctgtgg tgactcagga gccctcactg actgtgtccc caggagggac agtcactctc    60
acctgtgcct ctaccgctgg agctgtcacc agtgatcttt ttcccttctg gctccagcag    120
aagcctggcc aagcccccag gacacttatt tataatacaa acaaactgta ctcctggacc    180
ccagcccggt tctcaggctc cctctttggg ggtaaagctg ccctgaccct tcgggtgcg    240 cagcctgaag atgaggctga atattactgc ctgctctcct atgctggtgc tcgcttgttc    300
ggcggaggga ccaagttgac cgtcctg                                        327
```

<210> SEQ ID NO 17
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 17

```
caggtgcagc tggtggagtc tgggggaggc gtggtccagc ctgggaggtc cctgagactt    60
tcatgtgcag cctctggatt caccttcagt agttatggca tgcactgggt ccgccaggct    120
ccaggcaagg ggctggagtg ggtggcagtt atgtcttatg atggaagtaa gatatactat    180
gcagactccg tgaagggccg attcaccatc tccagagaca attccaagaa cacgctgtat    240
ctgcaaatgg acagcctgag agctgaggac acggctgtgt attactgtgc gaaagttggt    300
tattatgatg gtagtcgtta tgacctaatc gctgaatact ccagtactg ggccagggc    360 accctggtca ccgtctcctc a                                              381
```

<210> SEQ ID NO 18
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 18

```
cagtctgtgc tgactcagcc gccctcagtg tctggggccg cagggcagag ggtcaccatc    60
tcctgcactg ggagcagctc caacatcggg gcaggttatg atgtacactg gtatcagcaa    120
cttccaggaa cagcccccaa actcctcatc tatggtaaca acaatcggcc ctcaggggtc    180
cctgaccgat tctctggctc caagtctgac acttcagcct ccctggccat cactgggctc    240
cggcctgagg atgaacttga ttattactgc cagtcctatg acaacaggct gagtgcttat    300
```

```
gtcttcggaa ctgggaccaa ggtcaccgtc cta                              333
```

<210> SEQ ID NO 19
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 19

```
caggtgcagc tggtgcagtc tggggggaggc ctggtacagc ctggcaggtc cctgagactc    60
tgctgtgcag cctctggatt cagctttgat gattttgcca tgcactgggt ccggcaagct   120
ccagggaagg gcctggagtg gtctcaggt attaattgga atagtggtca cataggctat    180
gcggactctg tgaagggccg attcaccatc tccagagaca cgccaagaa ctccctgtgt    240
ctgcaaatga acagtctgag acctgaggac acggccttgt attactgtgc aaaagatcgg   300
gcgtattact ttggttcagg gacctcaggt ggtgcttttg atgtctgggg ccaagggacc   360
ctggtcaccg tctcctca                                                  378
```

<210> SEQ ID NO 20
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 20

```
gacatcgtga tgacccagtc tccatcgtcc ctgtctgcat ctgtaggaga cagagtcacc    60
atcacttgcc gggcaagtca gaacattatc agctatttaa attggtatca gcagaaacca   120
gggaaagccc ctaagctcct gatctatgat gcatccagtt tgcaaagtgg ggtcccatca   180
aggttcagtg gcagtggttc tgggacagat ttcactctca ccatcagcag tctgcaacct   240
gaagattttg caacttacta ctgtcaaagg agttttagta ccccgctcac tttcggcgga   300
gggaccaagg tggagatcaa a                                              321
```

<210> SEQ ID NO 21
<211> LENGTH: 122
<212> TYPE: PRT
<213> ORGANISM: Artificial sequence
<220> FEATURE:
<223> OTHER INFORMATION: Synthetic amino acid

<400> SEQUENCE: 21

```
Gln Val Gln Leu Val Gln Ser Gly Ala Glu Val Lys Lys Pro Gly Ala
1               5                   10                  15

Ser Val Asn Ile Ser Cys Lys Ala Ser Gly Tyr Thr Phe Thr Asn Tyr
            20                  25                  30

Phe Ile His Trp Val Arg Gln Ala Pro Gly Gln Gly Leu Glu Trp Met
        35                  40                  45

Gly Met Ile Asn Pro Arg Gly Gly Ser Thr His Phe Ala Gln Lys Phe
    50                  55                  60

Gln Ala Arg Val Thr Met Thr Arg Asp Thr Ser Thr Asn Thr Val Tyr
65                  70                  75                  80

Met Glu Leu Ser Ser Leu Arg Ser Glu Asp Thr Ala Met Tyr Tyr Cys
                85                  90                  95

Ala Lys Gly Ile Cys Lys Ile Ser Phe Met Cys Pro Phe Asp Pro Trp
            100                 105                 110
```

```
Gly Gln Gly Thr Leu Val Thr Val Ser Ser
        115                 120
```

<210> SEQ ID NO 22
<211> LENGTH: 107
<212> TYPE: PRT
<213> ORGANISM: Artificial sequence
<220> FEATURE:
<223> OTHER INFORMATION: Synthetic amino acid

<400> SEQUENCE: 22

```
Asp Ile Val Met Thr Gln Ser Pro Ala Ser Leu Ser Ala Ser Val Arg
1               5                   10                  15

Asp Arg Val Thr Ile Thr Cys Arg Ala Ser Gln Ser Ile Asn Asn His
            20                  25                  30

Val Asn Trp Tyr Gln Gln Lys Pro Gly Lys Ala Pro Lys Leu Leu Ile
        35                  40                  45

Tyr Ser Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Thr Phe Gly Gln Gly Thr Lys Val Glu Ile Lys
            100                 105
```

<210> SEQ ID NO 23
<211> LENGTH: 124
<212> TYPE: PRT
<213> ORGANISM: Artificial sequence
<220> FEATURE:
<223> OTHER INFORMATION: Synthetic amino acid

<400> SEQUENCE: 23

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Val Ile Ser Tyr Asp Ile Ile Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Phe Pro Asn Ser Ser Gly Glu Gly Phe Phe Asp
            100                 105                 110

Tyr Trp Gly Gln Gly Thr Leu Val Thr Val Ser Ser
        115                 120
```

<210> SEQ ID NO 24
<211> LENGTH: 107
<212> TYPE: PRT
<213> ORGANISM: Artificial sequence
<220> FEATURE:
<223> OTHER INFORMATION: Synthetic amino acid

<400> SEQUENCE: 24

```
Glu Ile Val Met Thr Gln Ser Pro Ala Thr Leu Ser Val Ser Pro Gly
```

-continued

```
                1               5                  10                 15
            Glu Arg Ala Thr Leu Ser Cys Arg Ala Ser Gln Ser Leu Ser Asn Asn
                            20                  25                 30

Leu Ala Trp Tyr Gln Gln Lys Pro Gly Gln Ala Pro Arg Leu Leu Ile
                        35                  40                 45

Tyr Gly Ala Ser Thr Arg Ala Thr Gly Ile Pro Ala Arg Phe Ser Gly
                    50                  55                 60

Ser Gly Ser Gly Thr Gln Phe Thr Leu Thr Ile Ser Ser Leu Gln Ser
             65                  70                  75                 80

Glu Asp Ile Ala Val Tyr Tyr Cys Gln Gln Phe Asn Asn Trp Pro Trp
                            85                  90                 95

Thr Phe Gly Gln Gly Thr Lys Val Glu Ile Lys
                           100                 105
```

<210> SEQ ID NO 25
<211> LENGTH: 121
<212> TYPE: PRT
<213> ORGANISM: Artificial sequence
<220> FEATURE:
<223> OTHER INFORMATION: Synthetic amino acid

<400> SEQUENCE: 25

```
            Gln Val Gln Leu Val Glu Ser Gly Gly Gly Val Val Gln Pro Gly Arg
            1               5                  10                 15

Ser Leu Arg Leu Ser Cys Ala Ala Ser Gly Phe Ile Phe Glu Asn Tyr
                            20                  25                 30

Gly Met His Trp Val Arg Gln Ala Pro Gly Lys Gly Leu Glu Trp Val
                        35                  40                 45

Ala Val Ile Ser Tyr Asp Gly Asp Asn Lys Asp Tyr Ser Lys Ser Val
                    50                  55                 60

Lys Gly Arg Phe Thr Ile Ser Arg Asp Asn Ser Lys Asn Thr Leu His
             65                  70                  75                 80

Leu Gln Met Asn Ser Leu Arg Thr Glu Asp Thr Ala Val Tyr Tyr Cys
                            85                  90                 95

Ala Lys Glu Pro Ser Lys Ser Trp Phe Arg Phe Phe Gly Thr Trp Gly
                           100                 105                110

Gln Gly Thr Leu Val Thr Val Ser Ser
                       115                 120
```

<210> SEQ ID NO 26
<211> LENGTH: 105
<212> TYPE: PRT
<213> ORGANISM: Artificial sequence
<220> FEATURE:
<223> OTHER INFORMATION: Synthetic amino acid

<400> SEQUENCE: 26

```
            Gln Ile Val Leu Thr Gln Ala Pro Ser Val Ser Val Ala Pro Gly Gln
            1               5                  10                 15

Thr Ala Arg Ile Thr Cys Gly Gly Thr Gly Ser Lys Gly Val His Trp
                            20                  25                 30

Tyr Gln Gln Lys Pro Gly Gln Ala Pro Val Val Val His Asp Asp
                        35                  40                 45

Ser Asp Arg Pro Ser Gly Ile Pro Gly Arg Phe Ser Gly Ser Asn Ser
                    50                  55                 60

Gly Asn Ala Ala Met Leu Thr Ile Ser Arg Val Glu Ala Gly Asp Glu
             65                  70                  75                 80
```

Ala Asp Tyr Tyr Cys Gln Val Trp Asp Ser Val Ser Asp Val Val Phe
                85                  90                  95

Gly Gly Gly Thr Lys Leu Thr Val Leu
            100                 105

<210> SEQ ID NO 27
<211> LENGTH: 123
<212> TYPE: PRT
<213> ORGANISM: Artificial sequence
<220> FEATURE:
<223> OTHER INFORMATION: Synthetic amino acid

<400> SEQUENCE: 27

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Glu Ser
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Asp
65                  70                  75                  80

Leu Gln Met Asn Ser Leu Arg Val Asp Asp Thr Ala Val Tyr Tyr Cys
                85                  90                  95

Val Arg Asp Gly Ile Leu Asn Tyr Tyr Ala Gly Gly Ser Lys Asp Tyr
            100                 105                 110

Trp Gly Gln Gly Thr Leu Val Thr Val Ser Ser
        115                 120

<210> SEQ ID NO 28
<211> LENGTH: 110
<212> TYPE: PRT
<213> ORGANISM: Artificial sequence
<220> FEATURE:
<223> OTHER INFORMATION: Synthetic amino acid

<400> SEQUENCE: 28

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Thr Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Asn Ile Pro Leu Phe Gly Gly Gly Thr Lys Val Thr Val Leu
            100                 105                 110

<210> SEQ ID NO 29
<211> LENGTH: 122
<212> TYPE: PRT
<213> ORGANISM: Artificial sequence
<220> FEATURE:
<223> OTHER INFORMATION: Synthetic amino acid -continued

<400> SEQUENCE: 29

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Met Cys Val Ser Trp Ile Arg Gln Thr Pro Gly Lys Ala Leu Glu
        35                  40                  45

Trp Leu Ala Leu Ile Asp Trp Glu Asp Asp Lys Tyr Tyr Asn Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Ala Arg Gly Thr Gly Arg Asp Lys Ala Met Val Phe Val Tyr Trp
            100                 105                 110

Gly Gln Gly Thr Leu Val Thr Val Ser Ser
        115                 120

<210> SEQ ID NO 30
<211> LENGTH: 112
<212> TYPE: PRT
<213> ORGANISM: Artificial sequence
<220> FEATURE:
<223> OTHER INFORMATION: Synthetic amino acid

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Lys Asn Phe Leu Ala Trp Tyr Gln Gln Lys Pro Gly Gln
        35                  40                  45

Pro Pro Lys Leu Leu Ile Ser Trp Ala Ser Thr Arg Glu Pro Gly Ile
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Leu Phe Gly Gly Gly Thr Lys Val Glu Ile Lys
            100                 105                 110

<210> SEQ ID NO 31
<211> LENGTH: 121
<212> TYPE: PRT
<213> ORGANISM: Artificial sequence
<220> FEATURE:
<223> OTHER INFORMATION: Synthetic amino acid

<400> SEQUENCE: 31

Glu Val Gln Leu Val Glu Ser Gly Gly Gly Leu Val Arg Pro Gly Gly
1               5                   10                  15

Ser Leu Arg Leu Ser Cys Ala Gly Ser Gly Phe Thr Phe Ser Ser Tyr
            20                  25                  30

Ala Leu His Trp Leu Arg Gln Ala Pro Gly Lys Gly Leu Glu Tyr Val
        35                  40                  45

Ser Ser Ile Asn Asp Asn Gly Arg Leu Thr Phe Tyr Ala Asn Ser Val
    50                  55                  60

-continued

Lys Gly Arg Phe Thr Ile Ser Arg Asp Asn Ser Lys Asn Thr Leu Tyr
 65                  70                  75                  80

Leu Gln Met Gly Arg Leu Arg Ala Asp Asp Met Ala Val Tyr Tyr Cys
             85                  90                  95

Ala Arg Gly Phe Asp Glu Asn Thr Gly Tyr Tyr Leu Asp Asn Trp Gly
            100                 105                 110

Gln Gly Thr Leu Val Thr Val Ser Ser
            115                 120

<210> SEQ ID NO 32
<211> LENGTH: 110
<212> TYPE: PRT
<213> ORGANISM: Artificial sequence
<220> FEATURE:
<223> OTHER INFORMATION: Synthetic amino acid

<400> SEQUENCE: 32

Gln Ser Val Leu Thr Gln Pro Pro Ser Val Ala Ala Pro Arg Gln
 1               5                  10                  15

Lys Val Thr Ile Ser Cys Ser Gly Thr Ser Ser Asn Ile Gly Asn Asn
             20                  25                  30

Tyr Val Ser Trp Tyr Gln Gln Leu Pro Gly Thr Ala Pro Arg Leu Leu
         35                  40                  45

Ile Tyr Asp Asn Asn Arg Arg Pro Ser Gly Ile Pro Asp Arg Phe Ser
 50                  55                  60

Gly Ser Lys Ser Gly Thr Ser Ala Thr Leu Asp Ile Thr Gly Leu Gln
 65                  70                  75                  80

Thr Gly Asp Glu Ala Asp Tyr Tyr Cys Gly Thr Trp Asp Ser Ser Leu
             85                  90                  95

Ser Phe Val Val Phe Gly Gly Gly Thr Lys Leu Thr Val Leu
            100                 105                 110

<210> SEQ ID NO 33
<211> LENGTH: 123
<212> TYPE: PRT
<213> ORGANISM: Artificial sequence
<220> FEATURE:
<223> OTHER INFORMATION: Synthetic amino acid

<400> SEQUENCE: 33

Gln Val Gln Leu Val Glu Ser Gly Gly Val Val Gln Pro Gly Arg
 1               5                  10                  15

Ser Leu Arg Leu Ala Cys Ala Ala Ser Gly Phe Thr Leu Ser Asp Phe
             20                  25                  30

Ala Ile His Trp Val Arg Gln Ala Pro Gly Lys Gly Leu Glu Trp Val
         35                  40                  45

Ala Ile Ile Ser Tyr Asp Gly Asn Ile Lys Tyr Ala Asp Ser Val
 50                  55                  60

Lys Gly Arg Phe Thr Ile Ser Ser Asp Asn Ser Lys Asn Thr Val Tyr
 65                  70                  75                  80

Leu Gln Met Asn Ser Leu Arg Ala Glu Asp Thr Ala Met Tyr Tyr Cys
             85                  90                  95

Ala Arg Asp Pro Asp Val Val Thr Ala His Asp Ala Phe Asp Ile
            100                 105                 110

Trp Gly Gln Gly Thr Leu Val Thr Val Ser Ser
            115                 120

<210> SEQ ID NO 34

```
<211> LENGTH: 107
<212> TYPE: PRT
<213> ORGANISM: Artificial sequence
<220> FEATURE:
<223> OTHER INFORMATION: Synthetic amino acid

<400> SEQUENCE: 34

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Leu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Phe Arg
                85                  90                  95

Thr Phe Gly Gln Gly Thr Lys Val Glu Val Lys
            100                 105

<210> SEQ ID NO 35
<211> LENGTH: 130
<212> TYPE: PRT
<213> ORGANISM: Artificial sequence
<220> FEATURE:
<223> OTHER INFORMATION: Synthetic amino acid

<400> SEQUENCE: 35

Gln Val Gln Leu Val Glu Ser Gly Gly Val Val Gln Pro Gly Arg
1               5                   10                  15

Ser Leu Arg Leu Ser Cys Val Gly Ser Gly Phe Ser Leu Ser Asp Tyr
            20                  25                  30

Ala Met Tyr Trp Val Arg Gln Ala Pro Gly Arg Gly Leu Glu Trp Val
        35                  40                  45

Ala Val Ile Ser Tyr Asp Gly Arg Asn Ala Tyr Tyr Ala Glu Ser Val
    50                  55                  60

Lys Gly Arg Phe Ile Ile Ser Arg Asp Asn Ser Lys Asn Thr Leu Tyr
65                  70                  75                  80

Leu Gln Met Thr Ser Leu Arg Ile Glu Asp Thr Ala Val Tyr Tyr Cys
                85                  90                  95

Val Arg Gly Glu Phe Ser Thr Ser Phe Cys Gly Ala Asp Cys Pro Tyr
            100                 105                 110

His Tyr Tyr Gly Met Asp Val Trp Gly Arg Gly Thr Leu Val Thr Val
        115                 120                 125

Ser Ser
    130

<210> SEQ ID NO 36
<211> LENGTH: 109
<212> TYPE: PRT
<213> ORGANISM: Artificial sequence
<220> FEATURE:
<223> OTHER INFORMATION: Synthetic amino acid

<400> SEQUENCE: 36

Gln Ala Val Val Thr Gln Glu Pro Ser Leu Thr Val Ser Pro Gly Gly
1               5                   10                  15
```

```
Thr Val Thr Leu Thr Cys Ala Ser Thr Ala Gly Ala Val Thr Ser Asp
            20                  25                  30

Leu Phe Pro Phe Trp Leu Gln Gln Lys Pro Gly Gln Ala Pro Arg Thr
        35                  40                  45

Leu Ile Tyr Asn Thr Asn Lys Leu Tyr Ser Trp Thr Pro Ala Arg Phe
 50                  55                  60

Ser Gly Ser Leu Phe Gly Gly Lys Ala Ala Leu Thr Leu Ser Gly Ala
 65                  70                  75                  80

Gln Pro Glu Asp Glu Ala Glu Tyr Tyr Cys Leu Leu Ser Tyr Ala Gly
                85                  90                  95

Ala Arg Leu Phe Gly Gly Gly Thr Lys Leu Thr Val Leu
            100                 105
```

<210> SEQ ID NO 37
<211> LENGTH: 127
<212> TYPE: PRT
<213> ORGANISM: Artificial sequence
<220> FEATURE:
<223> OTHER INFORMATION: Synthetic amino acid

<400> SEQUENCE: 37

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Lys Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                85                  90                  95

Ala Lys Val Gly Tyr Tyr Asp Gly Ser Arg Tyr Asp Leu Ile Ala Glu
            100                 105                 110

Tyr Phe Gln Tyr Trp Gly Gln Gly Thr Leu Val Thr Val Ser Ser
        115                 120                 125
```

<210> SEQ ID NO 38
<211> LENGTH: 111
<212> TYPE: PRT
<213> ORGANISM: Artificial sequence
<220> FEATURE:
<223> OTHER INFORMATION: Synthetic amino acid

<400> SEQUENCE: 38

```
Gln Ser Val Leu Thr Gln Pro Pro Ser Val Ser Gly Ala Ala Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
 50                  55                  60

Ser Gly Ser Lys Ser Asp Thr Ser Ala Ser Leu Ala Ile Thr Gly Leu
 65                  70                  75                  80

Arg Pro Glu Asp Glu Leu Asp Tyr Tyr Cys Gln Ser Tyr Asp Asn Arg
                85                  90                  95
```

Leu Ser Ala Tyr Val Phe Gly Thr Gly Thr Lys Val Thr Val Leu
            100                 105                 110

<210> SEQ ID NO 39
<211> LENGTH: 126
<212> TYPE: PRT
<213> ORGANISM: Artificial sequence
<220> FEATURE:
<223> OTHER INFORMATION: Synthetic amino acid

<400> SEQUENCE: 39

Gln Val Gln Leu Val Gln Ser Gly Gly Gly Leu Val Gln Pro Gly Arg
1               5                   10                  15

Ser Leu Arg Leu Cys Cys Ala Ala Ser Gly Phe Ser Phe Asp Asp Phe
            20                  25                  30

Ala Met His Trp Val Arg Gln Ala Pro Gly Lys Gly Leu Glu Trp Val
        35                  40                  45

Ser Gly Ile Asn Trp Asn Ser Gly His Ile Gly Tyr Ala Asp Ser Val
    50                  55                  60

Lys Gly Arg Phe Thr Ile Ser Arg Asp Asn Ala Lys Asn Ser Leu Cys
65                  70                  75                  80

Leu Gln Met Asn Ser Leu Arg Pro Glu Asp Thr Ala Leu Tyr Tyr Cys
                85                  90                  95

Ala Lys Asp Arg Ala Tyr Tyr Phe Gly Ser Gly Thr Ser Gly Gly Ala
            100                 105                 110

Phe Asp Val Trp Gly Gln Gly Thr Leu Val Thr Val Ser Ser
            115                 120                 125

<210> SEQ ID NO 40
<211> LENGTH: 107
<212> TYPE: PRT
<213> ORGANISM: Artificial sequence
<220> FEATURE:
<223> OTHER INFORMATION: Synthetic amino acid

<400> SEQUENCE: 40

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asn Ile Ile Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ser Phe Ser Thr Pro Leu
                85                  90                  95

Thr Phe Gly Gly Gly Thr Lys Val Glu Ile Lys
            100                 105

<210> SEQ ID NO 41
<211> LENGTH: 8
<212> TYPE: PRT
<213> ORGANISM: Artificial sequence
<220> FEATURE:
<223> OTHER INFORMATION: Synthetic amino acid

<400> SEQUENCE: 41

```
Gly Tyr Thr Phe Thr Asn Tyr Phe
1               5

<210> SEQ ID NO 42
<211> LENGTH: 8
<212> TYPE: PRT
<213> ORGANISM: Artificial sequence
<220> FEATURE:
<223> OTHER INFORMATION: Synthetic amino acid

<400> SEQUENCE: 42

Ile Asn Pro Arg Gly Gly Ser Thr
1               5

<210> SEQ ID NO 43
<211> LENGTH: 15
<212> TYPE: PRT
<213> ORGANISM: Artificial sequence
<220> FEATURE:
<223> OTHER INFORMATION: Synthetic amino acid

<400> SEQUENCE: 43

Ala Lys Gly Ile Cys Lys Ile Ser Phe Met Cys Pro Phe Asp Pro
1               5                   10                  15

<210> SEQ ID NO 44
<211> LENGTH: 8
<212> TYPE: PRT
<213> ORGANISM: Artificial sequence
<220> FEATURE:
<223> OTHER INFORMATION: Synthetic amino acid

<400> SEQUENCE: 44

Gly Phe Thr Phe Ser Ser His Ala
1               5

<210> SEQ ID NO 45
<211> LENGTH: 8
<212> TYPE: PRT
<213> ORGANISM: Artificial sequence
<220> FEATURE:
<223> OTHER INFORMATION: Synthetic amino acid

<400> SEQUENCE: 45

Ile Ser Tyr Asp Ile Ile Asn Glu
1               5

<210> SEQ ID NO 46
<211> LENGTH: 17
<212> TYPE: PRT
<213> ORGANISM: Artificial sequence
<220> FEATURE:
<223> OTHER INFORMATION: Synthetic amino acid

<400> SEQUENCE: 46

Ala Arg Asp Gly Tyr Phe Pro Asn Ser Ser Gly Glu Gly Phe Phe Asp
1               5                   10                  15

Tyr

<210> SEQ ID NO 47
<211> LENGTH: 8
<212> TYPE: PRT
<213> ORGANISM: Artificial sequence
<220> FEATURE:
<223> OTHER INFORMATION: Synthetic amino acid

<400> SEQUENCE: 47
```

Gly Phe Ile Phe Glu Asn Tyr Gly
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic amino acid

<400> SEQUENCE: 48

Ile Ser Tyr Asp Gly Asp Asn Lys
1               5

<210> SEQ ID NO 49
<211> LENGTH: 14
<212> TYPE: PRT
<213> ORGANISM: Artificial sequence
<220> FEATURE:
<223> OTHER INFORMATION: Synthetic amino acid

<400> SEQUENCE: 49

Ala Lys Glu Pro Ser Lys Ser Trp Phe Arg Phe Phe Glu Thr
1               5                   10

<210> SEQ ID NO 50
<211> LENGTH: 8
<212> TYPE: PRT
<213> ORGANISM: Artificial sequence
<220> FEATURE:
<223> OTHER INFORMATION: Synthetic amino acid

<400> SEQUENCE: 50

Gly Phe Thr Phe Ser Glu Ser Tyr
1               5

<210> SEQ ID NO 51
<211> LENGTH: 8
<212> TYPE: PRT
<213> ORGANISM: Artificial sequence
<220> FEATURE:
<223> OTHER INFORMATION: Synthetic amino acid

<400> SEQUENCE: 51

Ile Ser Ser Ser Ser Ser Tyr Thr
1               5

<210> SEQ ID NO 52
<211> LENGTH: 16
<212> TYPE: PRT
<213> ORGANISM: Artificial sequence
<220> FEATURE:
<223> OTHER INFORMATION: Synthetic amino acid

<400> SEQUENCE: 52

Val Arg Asp Gly Ile Leu Asn Tyr Tyr Ala Gly Gly Ser Lys Asp Tyr
1               5                   10                  15

<210> SEQ ID NO 53
<211> LENGTH: 10
<212> TYPE: PRT
<213> ORGANISM: Artificial sequence
<220> FEATURE:
<223> OTHER INFORMATION: Synthetic amino acid

<400> SEQUENCE: 53

```
Gly Phe Ser Leu Thr Thr Ser Gly Met Cys
1               5                   10

<210> SEQ ID NO 54
<211> LENGTH: 7
<212> TYPE: PRT
<213> ORGANISM: Artificial sequence
<220> FEATURE:
<223> OTHER INFORMATION: Synthetic amino acid

<400> SEQUENCE: 54

Ile Asp Trp Glu Asp Asp Lys
1               5

<210> SEQ ID NO 55
<211> LENGTH: 14
<212> TYPE: PRT
<213> ORGANISM: Artificial sequence
<220> FEATURE:
<223> OTHER INFORMATION: Synthetic amino acid

<400> SEQUENCE: 55

Ala Arg Gly Thr Gly Arg Asp Lys Ala Met Val Phe Val Tyr
1               5                   10

<210> SEQ ID NO 56
<211> LENGTH: 8
<212> TYPE: PRT
<213> ORGANISM: Artificial sequence
<220> FEATURE:
<223> OTHER INFORMATION: Synthetic amino acid

<400> SEQUENCE: 56

Gly Phe Thr Phe Ser Ser Tyr Ala
1               5

<210> SEQ ID NO 57
<211> LENGTH: 8
<212> TYPE: PRT
<213> ORGANISM: Artificial sequence
<220> FEATURE:
<223> OTHER INFORMATION: Synthetic amino acid

<400> SEQUENCE: 57

Ile Asn Asp Asn Gly Arg Leu Thr
1               5

<210> SEQ ID NO 58
<211> LENGTH: 14
<212> TYPE: PRT
<213> ORGANISM: Artificial sequence
<220> FEATURE:
<223> OTHER INFORMATION: Synthetic amino acid

<400> SEQUENCE: 58

Ala Arg Gly Phe Asp Glu Asn Thr Gly Tyr Tyr Leu Asp Asn
1               5                   10

<210> SEQ ID NO 59
<211> LENGTH: 8
<212> TYPE: PRT
<213> ORGANISM: Artificial sequence
<220> FEATURE:
<223> OTHER INFORMATION: Synthetic amino acid

<400> SEQUENCE: 59

Gly Phe Thr Leu Ser Asp Phe Ala
```

-continued 1               5

<210> SEQ ID NO 60
<211> LENGTH: 8
<212> TYPE: PRT
<213> ORGANISM: Artificial sequence
<220> FEATURE:
<223> OTHER INFORMATION: Synthetic amino acid

<400> SEQUENCE: 60

Ile Ser Tyr Asp Gly Asn Ile Lys
1               5

<210> SEQ ID NO 61
<211> LENGTH: 16
<212> TYPE: PRT
<213> ORGANISM: Artificial sequence
<220> FEATURE:
<223> OTHER INFORMATION: Synthetic amino acid

<400> SEQUENCE: 61

Ala Arg Asp Pro Asp Val Val Glu Thr Ala His Asp Ala Phe Asp Ile
1               5                   10                  15

<210> SEQ ID NO 62
<211> LENGTH: 8
<212> TYPE: PRT
<213> ORGANISM: Artificial sequence
<220> FEATURE:
<223> OTHER INFORMATION: Synthetic amino acid

<400> SEQUENCE: 62

Gly Phe Ser Leu Ser Asp Tyr Ala
1               5

<210> SEQ ID NO 63
<211> LENGTH: 8
<212> TYPE: PRT
<213> ORGANISM: Artificial sequence
<220> FEATURE:
<223> OTHER INFORMATION: Synthetic amino acid

<400> SEQUENCE: 63

Ile Ser Tyr Asp Gly Arg Asn Ala
1               5

<210> SEQ ID NO 64
<211> LENGTH: 23
<212> TYPE: PRT
<213> ORGANISM: Artificial sequence
<220> FEATURE:
<223> OTHER INFORMATION: Synthetic amino acid

<400> SEQUENCE: 64

Val Arg Gly Glu Phe Ser Thr Ser Phe Cys Gly Ala Asp Cys Pro Tyr
1               5                   10                  15

His Tyr Tyr Gly Met Asp Val
            20

<210> SEQ ID NO 65
<211> LENGTH: 8
<212> TYPE: PRT
<213> ORGANISM: Artificial sequence
<220> FEATURE:
<223> OTHER INFORMATION: Synthetic amino acid

<400> SEQUENCE: 65

```
Gly Phe Thr Phe Ser Ser Tyr Gly
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic amino acid

<400> SEQUENCE: 66

Met Ser Tyr Asp Gly Ser Lys Ile
1               5

<210> SEQ ID NO 67
<211> LENGTH: 20
<212> TYPE: PRT
<213> ORGANISM: Artificial sequence
<220> FEATURE:
<223> OTHER INFORMATION: Synthetic amino acid

<400> SEQUENCE: 67

Ala Lys Val Gly Tyr Tyr Asp Gly Ser Arg Tyr Asp Leu Ile Ala Glu
1               5                   10                  15

Tyr Phe Gln Tyr
            20

<210> SEQ ID NO 68
<211> LENGTH: 8
<212> TYPE: PRT
<213> ORGANISM: Artificial sequence
<220> FEATURE:
<223> OTHER INFORMATION: Synthetic amino acid

<400> SEQUENCE: 68

Gly Phe Ser Phe Asp Asp Phe Ala
1               5

<210> SEQ ID NO 69
<211> LENGTH: 8
<212> TYPE: PRT
<213> ORGANISM: Artificial sequence
<220> FEATURE:
<223> OTHER INFORMATION: Synthetic amino acid

<400> SEQUENCE: 69

Ile Asn Trp Asn Ser Gly His Ile
1               5

<210> SEQ ID NO 70
<211> LENGTH: 19
<212> TYPE: PRT
<213> ORGANISM: Artificial sequence
<220> FEATURE:
<223> OTHER INFORMATION: Synthetic amino acid

<400> SEQUENCE: 70

Ala Lys Asp Arg Ala Tyr Tyr Phe Gly Ser Gly Thr Ser Gly Gly Ala
1               5                   10                  15

Phe Asp Val

<210> SEQ ID NO 71
<211> LENGTH: 6
<212> TYPE: PRT
<213> ORGANISM: Artificial sequence
```

```
<220> FEATURE:
<223> OTHER INFORMATION: Synthetic amino acid

<400> SEQUENCE: 71

Gln Ser Ile Asn Asn His
1               5

<210> SEQ ID NO 72
<211> LENGTH: 3
<212> TYPE: PRT
<213> ORGANISM: Artificial sequence
<220> FEATURE:
<223> OTHER INFORMATION: Synthetic amino acid

<400> SEQUENCE: 72

Ser Thr Ser
1

<210> SEQ ID NO 73
<211> LENGTH: 9
<212> TYPE: PRT
<213> ORGANISM: Artificial sequence
<220> FEATURE:
<223> OTHER INFORMATION: Synthetic amino acid

<400> SEQUENCE: 73

Gln Gln Ser Tyr Ser Thr Pro Gly Thr
1               5

<210> SEQ ID NO 74
<211> LENGTH: 6
<212> TYPE: PRT
<213> ORGANISM: Artificial sequence
<220> FEATURE:
<223> OTHER INFORMATION: Synthetic amino acid

<400> SEQUENCE: 74

Gln Ser Leu Ser Asn Asn
1               5

<210> SEQ ID NO 75
<211> LENGTH: 3
<212> TYPE: PRT
<213> ORGANISM: Artificial sequence
<220> FEATURE:
<223> OTHER INFORMATION: Synthetic amino acid

<400> SEQUENCE: 75

Gly Ala Ser
1

<210> SEQ ID NO 76
<211> LENGTH: 9
<212> TYPE: PRT
<213> ORGANISM: Artificial sequence
<220> FEATURE:
<223> OTHER INFORMATION: Synthetic amino acid

<400> SEQUENCE: 76

Gln Gln Phe Asn Asn Trp Pro Trp Thr
1               5

<210> SEQ ID NO 77
<211> LENGTH: 6
<212> TYPE: PRT
<213> ORGANISM: Artificial sequence
<220> FEATURE:
```

<223> OTHER INFORMATION: Synthetic amino acid

<400> SEQUENCE: 77

Gly Thr Gly Ser Lys Gly
1               5

<210> SEQ ID NO 78
<211> LENGTH: 3
<212> TYPE: PRT
<213> ORGANISM: Artificial sequence
<220> FEATURE:
<223> OTHER INFORMATION: Synthetic amino acid

<400> SEQUENCE: 78

Asp Asp Ser
1

<210> SEQ ID NO 79
<211> LENGTH: 10
<212> TYPE: PRT
<213> ORGANISM: Artificial sequence
<220> FEATURE:
<223> OTHER INFORMATION: Synthetic amino acid

<400> SEQUENCE: 79

Gln Val Trp Asp Ser Val Ser Asp Val Val
1               5                   10

<210> SEQ ID NO 80
<211> LENGTH: 9
<212> TYPE: PRT
<213> ORGANISM: Artificial sequence
<220> FEATURE:
<223> OTHER INFORMATION: Synthetic amino acid

<400> SEQUENCE: 80

Ser Ser Asp Ile Gly Thr Tyr Thr Leu
1               5

<210> SEQ ID NO 81
<211> LENGTH: 3
<212> TYPE: PRT
<213> ORGANISM: Artificial sequence
<220> FEATURE:
<223> OTHER INFORMATION: Synthetic amino acid

<400> SEQUENCE: 81

Glu Gly Ser
1

<210> SEQ ID NO 82
<211> LENGTH: 10
<212> TYPE: PRT
<213> ORGANISM: Artificial sequence
<220> FEATURE:
<223> OTHER INFORMATION: Synthetic amino acid

<400> SEQUENCE: 82

Cys Ser Tyr Ala Gly Ser Asn Ile Pro Leu
1               5                   10

<210> SEQ ID NO 83
<211> LENGTH: 12
<212> TYPE: PRT
<213> ORGANISM: Artificial sequence
<220> FEATURE:
<223> OTHER INFORMATION: Synthetic amino acid

<400> SEQUENCE: 83

Gln Ser Val Leu Tyr Arg Ser Asn Asn Lys Asn Phe
1               5                   10

<210> SEQ ID NO 84
<211> LENGTH: 3
<212> TYPE: PRT
<213> ORGANISM: Artificial sequence
<220> FEATURE:
<223> OTHER INFORMATION: Synthetic amino acid

<400> SEQUENCE: 84

Trp Ala Ser
1

<210> SEQ ID NO 85
<211> LENGTH: 8
<212> TYPE: PRT
<213> ORGANISM: Artificial sequence
<220> FEATURE:
<223> OTHER INFORMATION: Synthetic amino acid

<400> SEQUENCE: 85

Gln Gln Tyr Tyr Ser Ala Pro Leu
1               5

<210> SEQ ID NO 86
<211> LENGTH: 8
<212> TYPE: PRT
<213> ORGANISM: Artificial sequence
<220> FEATURE:
<223> OTHER INFORMATION: Synthetic amino acid

<400> SEQUENCE: 86

Ser Ser Asn Ile Gly Asn Asn Tyr
1               5

<210> SEQ ID NO 87
<211> LENGTH: 3
<212> TYPE: PRT
<213> ORGANISM: Artificial sequence
<220> FEATURE:
<223> OTHER INFORMATION: Synthetic amino acid

<400> SEQUENCE: 87

Asp Asn Asn
1

<210> SEQ ID NO 88
<211> LENGTH: 11
<212> TYPE: PRT
<213> ORGANISM: Artificial sequence
<220> FEATURE:
<223> OTHER INFORMATION: Synthetic amino acid

<400> SEQUENCE: 88

Gly Thr Trp Asp Ser Ser Leu Ser Phe Val Val
1               5                   10

<210> SEQ ID NO 89
<211> LENGTH: 6
<212> TYPE: PRT
<213> ORGANISM: Artificial sequence
<220> FEATURE:
<223> OTHER INFORMATION: Synthetic amino acid

```
<400> SEQUENCE: 89

Gln Asn Ile Lys Asn Tyr
1               5

<210> SEQ ID NO 90
<211> LENGTH: 3
<212> TYPE: PRT
<213> ORGANISM: Artificial sequence
<220> FEATURE:
<223> OTHER INFORMATION: Synthetic amino acid

<400> SEQUENCE: 90

Ala Ala Ser
1

<210> SEQ ID NO 91
<211> LENGTH: 9
<212> TYPE: PRT
<213> ORGANISM: Artificial sequence
<220> FEATURE:
<223> OTHER INFORMATION: Synthetic amino acid

<400> SEQUENCE: 91

Gln Gln Ser Tyr Ser Ser Phe Arg Thr
1               5

<210> SEQ ID NO 92
<211> LENGTH: 9
<212> TYPE: PRT
<213> ORGANISM: Artificial sequence
<220> FEATURE:
<223> OTHER INFORMATION: Synthetic amino acid

<400> SEQUENCE: 92

Ala Gly Ala Val Thr Ser Asp Leu Phe
1               5

<210> SEQ ID NO 93
<211> LENGTH: 3
<212> TYPE: PRT
<213> ORGANISM: Artificial sequence
<220> FEATURE:
<223> OTHER INFORMATION: Synthetic amino acid

<400> SEQUENCE: 93

Asn Thr Asn
1

<210> SEQ ID NO 94
<211> LENGTH: 9
<212> TYPE: PRT
<213> ORGANISM: Artificial sequence
<220> FEATURE:
<223> OTHER INFORMATION: Synthetic amino acid

<400> SEQUENCE: 94

Leu Leu Ser Tyr Ala Gly Ala Arg Leu
1               5

<210> SEQ ID NO 95
<211> LENGTH: 9
<212> TYPE: PRT
<213> ORGANISM: Artificial sequence
<220> FEATURE:
<223> OTHER INFORMATION: Synthetic amino acid

<400> SEQUENCE: 95
```

```
Ser Ser Asn Ile Gly Ala Gly Tyr Asp
1               5

<210> SEQ ID NO 96
<211> LENGTH: 3
<212> TYPE: PRT
<213> ORGANISM: Artificial sequence
<220> FEATURE:
<223> OTHER INFORMATION: Synthetic amino acid

<400> SEQUENCE: 96

Gly Asn Asn
1

<210> SEQ ID NO 97
<211> LENGTH: 11
<212> TYPE: PRT
<213> ORGANISM: Artificial sequence
<220> FEATURE:
<223> OTHER INFORMATION: Synthetic amino acid

<400> SEQUENCE: 97

Gln Ser Tyr Asp Asn Arg Leu Ser Ala Tyr Val
1               5                   10

<210> SEQ ID NO 98
<211> LENGTH: 6
<212> TYPE: PRT
<213> ORGANISM: Artificial sequence
<220> FEATURE:
<223> OTHER INFORMATION: Synthetic amino acid

<400> SEQUENCE: 98

Gln Asn Ile Ile Ser Tyr
1               5

<210> SEQ ID NO 99
<211> LENGTH: 3
<212> TYPE: PRT
<213> ORGANISM: Artificial sequence
<220> FEATURE:
<223> OTHER INFORMATION: Synthetic amino acid

<400> SEQUENCE: 99

Asp Ala Ser
1

<210> SEQ ID NO 100
<211> LENGTH: 9
<212> TYPE: PRT
<213> ORGANISM: Artificial sequence
<220> FEATURE:
<223> OTHER INFORMATION: Synthetic amino acid

<400> SEQUENCE: 100

Gln Arg Ser Phe Ser Thr Pro Leu Thr
1               5
```